(12) United States Patent
Palmer et al.

(10) Patent No.: US 6,893,827 B1
(45) Date of Patent: May 17, 2005

(54) RECEPTOR FUNCTION ASSAY FOR G-PROTEIN COUPLED RECEPTORS AND ORPHAN RECEPTORS BY REPORTER ENZYME MUTANT COMPLEMENTATION

(75) Inventors: Michelle A. J. Palmer, Arlington, MA (US); Melissa Gee, Bedford, MA (US); Bonnie Tillotson, Belmont, MA (US); Xiao-Jia Chang, Lincoln, MA (US)

(73) Assignee: Applera Corporation, Bedford, MA (US)

( * ) Notice: Subject to any disclaimer, the term of this patent is extended or adjusted under 35 U.S.C. 154(b) by 0 days.

(21) Appl. No.: 09/654,499

(22) Filed: Sep. 1, 2000

Related U.S. Application Data

(60) Provisional application No. 60/180,669, filed on Feb. 7, 2000.

(51) Int. Cl.[7] .................... C07K 14/705; C07K 19/00; C12N 15/62; G01N 33/567
(52) U.S. Cl. ................... 435/7.1; 435/7.2; 435/7.21; 435/69.7; 536/23.4
(58) Field of Search ................. 435/7.1, 7.2, 69.7; 436/501; 536/23.4

(56) References Cited

U.S. PATENT DOCUMENTS

| 5,891,646 A | 4/1999 | Barak et al. |
| 6,110,693 A | 8/2000 | Barak et al. |
| 6,342,345 B1 * | 1/2002 | Blau et al. |

FOREIGN PATENT DOCUMENTS

| WO | WO 00/35274 | 6/2000 |

OTHER PUBLICATIONS

F. Rossi et al., "Monitoring Protein–Protein Interactions in Intact Eukaryotic Cells by β–galactosidase Complementation", Proc. Natl. Acad. Sci., vol. 94, pp. 8405–8410, (1997).

Barak et al., "A beta–Arrestin/Green Fluorescent Protein Biosensor for Detecting G Protein–coupled Receptor Activation", the Journal of biological Chemistry, vol. 272, No. 44, pp. 27497–27500, Oct. 31, 1997.

Stephanie Angers, et al., "Detection of $β_2$–adrenergic receptor dimerization in living cells using bioluminescence resonance energy transfer (BRET)", Proc. Natl. Acad. Sci. USA, vol. 97, Issue 7, pp. 3684–3689, Mar. 28, 2000.

Vsevolod V. Gurevich, et al., "Arrestin Interactions with G Protein–coupled Receptors. Direct Binding Studies of Wild Type and Mutant Arrestins with Rhodopsin, $β_2$–Adrenergic, and m2 Muscarinic Cholinergic Receptors", J. Biol. Chem., vol. 270, No. 2, pp. 720–731, Jan. 13, 1995.

Vsevolod V. Gurevich, et al., "Mechanism of Phosphorylation–Recognition by Visual Arrestin and the Transition of Arrestin into a High Affinity Binding State", Mol. Pharmacol., vol. 51, pp. 161–169, 1997.

* cited by examiner

*Primary Examiner*—John Ulm
(74) *Attorney, Agent, or Firm*—Piper Rudnick LLP; Steven B. Kelber

(57) ABSTRACT

Methods for detecting G-protein coupled receptor (GPCR) activity; methods of assaying GPCR activity; and methods of screening for GPCR ligands, G-protein-coupled receptor kinase (GRK) activity, and compounds that interact with components of the GPCR regulatory process are described.

47 Claims, 78 Drawing Sheets pICAST ALC

```
  1  CTGCAGCCTG AATATGGGCC AAACAGGATA TCTGTGGTAA GCAGTTCCTG
     GACGTCGGAC TTATACCCGG TTTGTCCTAT AGACACCATT CGTCAAGGAC

51  CCCCGGCTCA GGGCCAAGAA CAGATGGAAC AGCTGAATAT GGGCCAAACA
     GGGGCCGAGT CCCGGTTCTT GTCTACCTTG TCGACTTATA CCCGGTTTGT

101  GGATATCTGT GGTAAGCAGT TCCTGCCCCG GCTCAGGGCC AAGAACAGAT
     CCTATAGACA CCATTCGTCA AGGACGGGGC CGAGTCCCGG TTCTTGTCTA

151  GGTCCCCAGA TGCGGTCCAG CCCTCAGCAG TTTCTAGAGA ACCATCAGAT
     CCAGGGGTCT ACGCCAGGTC GGGAGTCGTC AAAGATCTCT TGGTAGTCTA

201  GTTTCCAGGG TGCCCCAAGG ACCTGAAATG ACCCTGTGCC TTATTTGAAC
     CAAAGGTCCC ACGGGGTTCC TGGACTTTAC TGGGACACGG AATAAACTTG

251  TAACCAATCA GTTCGCTTCT CGCTTCTGTT CGCGCGCTTC TGCTCCCCGA
     ATTGGTTAGT CAAGCGAAGA GCGAAGACAA GCGCGCGAAG ACGAGGGGCT

301  GCTCAATAAA AGAGCCCACA ACCCCTCACT CGGGGCGCCA GTCCTCCGAT
     CGAGTTATTT TCTCGGGTGT TGGGGAGTGA GCCCCGCGGT CAGGAGGCTA

351  TGACTGAGTC GCCCGGGTAC CCGTGTATCC AATAAACCCT CTTGCAGTTG
     ACTGACTCAG CGGGCCCATG GGCACATAGG TTATTTGGGA GAACGTCAAC

401  CATCCGACTT GTGGTCTCGC TGTTCCTTGG GAGGGTCTCC TCTGAGTGAT
     GTAGGCTGAA CACCAGAGCG ACAAGGAACC CTCCCAGAGG AGACTCACTA

451  TGACTACCCG TCAGCGGGGG TCTTTCATTT GGGGGCTCGT CCGGGATCGG
     ACTGATGGGC AGTCGCCCCC AGAAAGTAAA CCCCGAGCA GGCCCTAGCC

501  GAGACCCCTG CCCAGGGACC ACCGACCCAC CACCGGGAGG CAAGCTGGCC
     CTCTGGGGAC GGGTCCCTGG TGGCTGGGTG GTGGCCCTCC GTTCGACCGG

551  AGCAACTTAT CTGTGTCTGT CCGATTGTCT AGTGTCTATG ACTGATTTTA
     TCGTTGAATA GACACAGACA GGCTAACAGA TCACAGATAC TGACTAAAAT

601  TGCGCCTGCG TCGGTACTAG TTAGCTAACT AGCTCTGTAT CTGGCGGACC
     ACGCGGACGC AGCCATGATC AATCGATTGA TCGAGACATA GACCGCCTGG
```

FIG.10B pICAST ALC

```
 651   CGTGGTGGAA CTGACGAGTT CTGAACACCC GGCCGCAACC CTGGGAGACG
       GCACCACCTT GACTGCTCAA GACTTGTGGG CCGGCGTTGG GACCCTCTGC

701   TCCCAGGGAC TTTGGGGGCC GTTTTTGTGG CCCGACCTGA GGAAGGGAGT
       AGGGTCCCTG AAACCCCCGG CAAAAACACC GGGCTGGACT CCTTCCCTCA

751   CGATGTGGAA TCCGACCCCG TCAGGATATG TGGTTCTGGT AGGAGACGAG
       GCTACACCTT AGGCTGGGGC AGTCCTATAC ACCAAGACCA TCCTCTGCTC

801   AACCTAAAAC AGTTCCCGCC TCCGTCTGAA TTTTTGCTTT CGGTTTGGAA
       TTGGATTTTG TCAAGGGCGG AGGCAGACTT AAAAACGAAA GCCAAACCTT

851   CCGAAGCCGC GCGTCTTGTC TGCTGCAGCA TCGTTCTGTG TTGTCTCTGT
       GGCTTCGGCG CGCAGAACAG ACGACGTCGT AGCAAGACAC AACAGAGACA

901   CTGACTGTGT TTCTGTATTT GTCTGAAAAT TAGGGCCAGA CTGTTACCAC
       GACTGACACA AAGACATAAA CAGACTTTTA ATCCCGGTCT GACAATGGTG

951   TCCCTTAAGT TTGACCTTAG GTAACTGGAA AGATGTCGAG CGGCTCGCTC
       AGGGAATTCA AACTGGAATC CATTGACCTT TCTACAGCTC GCCGAGCGAG

1001   ACAACCAGTC GGTAGATGTC AAGAAGAGAC GTTGGGTTAC CTTCTGCTCT
       TGTTGGTCAG CCATCTACAG TTCTTCTCTG CAACCCAATG GAAGACGAGA

1051   GCAGAATGGC CAACCTTTAA CGTCGGATGG CCGCGAGACG GCACCTTTAA
       CGTCTTACCG GTTGGAAATT GCAGCCTACC GGCGCTCTGC CGTGGAAATT

1101   CCGAGACCTC ATCACCCAGG TTAAGATCAA GGTCTTTTCA CCTGGCCCGC
       GGCTCTGGAG TAGTGGGTCC AATTCTAGTT CCAGAAAAGT GGACCGGGCG

1151   ATGGACACCC AGACCAGGTC CCCTACATCG TGACCTGGGA AGCCTTGGCT
       TACCTGTGGG TCTGGTCCAG GGGATGTAGC ACTGGACCCT TCGGAACCGA

1201   TTTGACCCCC CTCCCTGGGT CAAGCCCTTT GTACACCCTA AGCCTCCGCC
       AAACTGGGGG GAGGGACCCA GTTCGGGAAA CATGTGGGAT TCGGAGGCGG

1251   TCCTCTTCCT CCATCCGCCC CGTCTCTCCC CCTTGAACCT CCTCGTTCGA
       AGGAGAAGGA GGTAGGCGGG GCAGAGAGGG GGAACTTGGA GGAGCAAGCT
```

FIG.10C pICAST ALC

```
1301    CCCCGCCTCG ATCCTCCCTT TATCCAGCCC TCACTCCTTC TCTAGGCGCC
        GGGGCGGAGC TAGGAGGGAA ATAGGTCGGG AGTGAGGAAG AGATCCGCGG

1351    GGCCGCTCTA GCCCATTAAT ACGACTCACT ATAGGGCGAT TCGAATCAGG
        CCGGCGAGAT CGGGTAATTA TGCTGAGTGA TATCCCGCTA AGCTTAGTCC

1401    CCTTGGCGCG CCGGATCCTT AATTAAGCGC AATTGGGAGG TGGCGGTAGC
        GGAACCGCGC GGCCTAGGAA TTAATTCGCG TTAACCCTCC ACCGCCATCG
```

```
+2             M   G   V   I   T   D   S   L   A   V   V   A   R   T   D
        ]--------------------------------------------------------------
1451    CTCGAGATGG GCGTGATTAC GGATTCACTG GCCGTCGTGG CCCGCACCGA
        GAGCTCTACC CGCACTAATG CCTAAGTGAC CGGCAGCACC GGGCGTGGCT

+2        R   P   S   Q   Q   L   R   S   L   N   G   E   W   R   F   A
        ------------------------------------------------------------
1501    TCGCCCTTCC CAACAGTTAC GCAGCCTGAA TGGCGAATGG CGCTTTGCCT
        AGCGGGAAGG GTTGTCAATG CGTCGGACTT ACCGCTTACC GCGAAACGGA

+2      W   F   P   A   P   E   A   V   P   E   S   W   L   E   C   D   L
        ------------------------------------------------------------
1551    GGTTTCCGGC ACCAGAAGCG GTGCCGGAAA GCTGGCTGGA GTGCGATCTT
        CCAAAGGCCG TGGTCTTCGC CACGGCCTTT CGACCGACCT CACGCTAGAA

+2        P   E   A   D   T   V   V   P   S   N   W   Q   M   H   G   Y
        ------------------------------------------------------------
1601    CCTGAGGCCG ATACTGTCGT CGTCCCCTCA AACTGGCAGA TGCACGGTTA
        GGACTCCGGC TATGACAGCA GCAGGGGAGT TTGACCGTCT ACGTGCCAAT

+2        D   A   P   I   Y   T   N   V   T   Y   P   I   T   V   N   P
        ------------------------------------------------------------
1651    CGATGCGCCC ATCTACACCA ACGTGACCTA TCCCATTACG GTCAATCCGC
        GCTACGCGGG TAGATGTGGT TGCACTGGAT AGGGTAATGC CAGTTAGGCG

+2        P   F   V   P   T   E   N   P   T   G   C   Y   S   L   T   F   N
        ------------------------------------------------------------
1701    CGTTTGTTCC CACGGAGAAT CCGACGGGTT GTTACTCGCT CACATTTAAT
        GCAAACAAGG GTGCCTCTTA GGCTGCCCAA CAATGAGCGA GTGTAAATTA
```

FIG.10D pICAST ALC

```
+2      V  D  E  S  W  L  Q  E  G  Q  T  R  I  I  F  D  G
        .................................................
1751    GTTGATGAAA GCTGGCTACA GGAAGGCCAG ACGCGAATTA TTTTTGATGG
        CAACTACTTT CGACCGATGT CCTTCCGGTC TGCGCTTAAT AAAAACTACC

+2      V  N  S  A  F  H  L  W  C  N  G  R  W  V  G  Y
        .................................................
1801    CGTTAACTCG GCGTTTCATC TGTGGTGCAA CGGGCGCTGG GTCGGTTACG
        GCAATTGAGC CGCAAAGTAG ACACCACGTT GCCCGCGACC CAGCCAATGC

+2      G  Q  D  S  R  L  P  S  E  F  D  L  S  A  F  L  R
        .................................................
1851    GCCAGGACAG TCGTTTGCCG TCTGAATTTG ACCTGAGCGC ATTTTTACGC
        CGGTCCTGTC AGCAAACGGC AGACTTAAAC TGGACTCGCG TAAAAATGCG

+2      A  G  E  N  R  L  A  V  M  V  L  R  W  S  D  G  S
        .................................................
1901    GCCGGAGAAA ACCGCCTCGC GGTGATGGTG CTGCGCTGGA GTGACGGCAG
        CGGCCTCTTT TGGCGGAGCG CCACTACCAC GACGCGACCT CACTGCCGTC

+2      Y  L  E  D  Q  D  M  W  R  M  S  G  I  F  R  D
        .................................................
1951    TTATCTGGAA GATCAGGATA TGTGGCGGAT GAGCGGCATT TTCCGTGACG
        AATAGACCTT CTAGTCCTAT ACACCGCCTA CTCGCCGTAA AAGGCACTGC

+2      V  S  L  L  H  K  P  T  T  Q  I  S  D  F  H  V  A
        .................................................
2001    TCTCGTTGCT GCATAAACCG ACTACACAAA TCAGCGATTT CCATGTTGCC
        AGAGCAACGA CGTATTTGGC TGATGTGTTT AGTCGCTAAA GGTACAACGG

+2      T  R  F  N  D  D  F  S  R  A  V  L  E  A  E  V  Q
        .................................................
2051    ACTCGCTTTA ATGATGATTT CAGCCGCGCT GTACTGGAGG CTGAAGTTCA
        TGAGCGAAAT TACTACTAAA GTCGGCGCGA CATGACCTCC GACTTCAAGT
```

FIG. 10E pICAST ALC

| +2 | M C G E L R D Y L R V T V S L W |
|---|---|
| 2101 | GATGTGCGGC GAGTTGCGTG ACTACCTACG GGTAACAGTT TCTTTATGGC<br>CTACACGCCG CTCAACGCAC TGATGGATGC CCATTGTCAA AGAAATACCG |

| +2 | Q G E T Q V A S G T A P F G E I |
|---|---|
| 2151 | AGGGTGAAAC GCAGGTCGCC AGCGGCACCG CGCCTTTCGG CGGTGAAATT<br>TCCCACTTTG CGTCCAGCGG TCGCCGTGGC GCGGAAAGCC GCCACTTTAA |

| +2 | I D E R G G Y A D R V T L R L N V |
|---|---|
| 2201 | ATCGATGAGC GTGGTGGTTA TGCCGATCGC GTCACACTAC GTCTGAACGT<br>TAGCTACTCG CACCACCAAT ACGGCTAGCG CAGTGTGATG CAGACTTGCA |

| +2 | E N P K L W S A E I P N L Y R A |
|---|---|
| 2251 | CGAAAACCCG AAACTGTGGA GCGCCGAAAT CCCGAATCTC TATCGTGCGG<br>GCTTTTGGGC TTTGACACCT CGCGGCTTTA GGGCTTAGAG ATAGCACGCC |

| +2 | V V E L H T A D G T L I E A E A C |
|---|---|
| 2301 | TGGTTGAACT GCACACCGCC GACGGCACGC TGATTGAAGC AGAAGCCTGC<br>ACCAACTTGA CGTGTGGCGG CTGCCGTGCG ACTAACTTCG TCTTCGGACG |

| +2 | D V G F R E V R I E N G L L L N |
|---|---|
| 2351 | GATGTCGGTT TCCGCGAGGT GCGGATTGAA AATGGTCTGC TGCTGCTGAA<br>CTACAGCCAA AGGCGCTCCA CGCCTAACTT TTACCAGACG ACGACGACTT |

| +2 | G K P L L I R G V N R H E H H P |
|---|---|
| 2401 | CGGCAAGCCG TTGCTGATTC GAGGCGTTAA CCGTCACGAG CATCATCCTC<br>GCCGTTCGGC AACGACTAAG CTCCGCAATT GGCAGTGCTC GTAGTAGGAG |

FIG. 10F pICAST ALC

```
+2       L   H   G   Q   V   M   D   E   Q   T   M   V   Q   D   I   L   L
         ............................................................
2451     TGCATGGTCA GGTCATGGAT GAGCAGACGA TGGTGCAGGA TATCCTGCTG
         ACGTACCAGT CCAGTACCTA CTCGTCTGCT ACCACGTCCT ATAGGACGAC

+2         M   K   Q   N   N   F   N   A   V   R   C   S   H   Y   P   N   H
         ............................................................
2501     ATGAAGCAGA ACAACTTTAA CGCCGTGCGC TGTTCGCATT ATCCGAACCA
         TACTTCGTCT TGTTGAAATT GCGGCACGCG ACAAGCGTAA TAGGCTTGGT

+2          P   L   W   Y   T   L   C   D   R   Y   G   L   Y   V   V   D
         ............................................................
2551     TCCGCTGTGG TACACGCTGT GCGACCGCTA CGGCCTGTAT GTGGTGGATG
         AGGCGACACC ATGTGCGACA CGCTGGCGAT GCCGGACATA CACCACCTAC

+2         E   A   N   I   E   T   H   G   M   V   P   M   N   R   L   T   D
         ............................................................
2601     AAGCCAATAT TGAAACCCAC GGCATGGTGC CAATGAATCG TCTGACCGAT
         TTCGGTTATA ACTTTGGGTG CCGTACCACG GTTACTTAGC AGACTGGCTA

+2          D   P   R   W   L   P   A   M   S   E   R   V   T   R   M   V   Q
         ............................................................
2651     GATCCGCGCT GGCTACCGGC GATGAGCGAA CGCGTAACGC GAATGGTGCA
         CTAGGCGCGA CCGATGGCCG CTACTCGCTT GCGCATTGCG CTTACCACGT

+2          R   D   R   N   H   P   S   V   I   I   W   S   L   G   N   E
         ............................................................
2701     GCGCGATCGT AATCACCCGA GTGTGATCAT CTGGTCGCTG GGGAATGAAT
         CGCGCTAGCA TTAGTGGGCT CACACTAGTA GACCAGCGAC CCCTTACTTA

+2          S   G   H   G   A   N   H   D   A   L   Y   R   W   I   K   S   V
         ............................................................
2751     CAGGCCACGG CGCTAATCAC GACGCGCTGT ATCGCTGGAT CAAATCTGTC
         GTCCGGTGCC GCGATTAGTG CTGCGCGACA TAGCGACCTA GTTTAGACAG
```

FIG.10G pICAST ALC

```
+2      D   P   S   R   P   V   Q   Y   E   G   G   G   A   D   T   T   A
        ...................................................................
2801    GATCCTTCCC GCCCGGTGCA GTATGAAGGC GGCGGAGCCG ACACCACGGC
        CTAGGAAGGG CGGGCCACGT CATACTTCCG CCGCCTCGGC TGTGGTGCCG

+2        T   D   I   I   C   P   M   Y   A   R   V   D   E   D   Q   P
        ...................................................................
2851    CACCGATATT ATTTGCCCGA TGTACGCGCG CGTGGATGAA GACCAGCCCT
        GTGGCTATAA TAAACGGGCT ACATGCGCGC GCACCTACTT CTGGTCGGGA

+2        F   P   A   V   P   K   W   S   I   K   K   W   L   S   L   P   G
        ...................................................................
2901    TCCCGGCTGT GCCGAAATGG TCCATCAAAA AATGGCTTTC GCTACCTGGA
        AGGGCCGACA CGGCTTTACC AGGTAGTTTT TTACCGAAAG CGATGGACCT

+2        E   T   R   P   L   I   L   C   E   Y   A   H   A   M   G   N   S
        ...................................................................
2951    GAGACGCGCC CGCTGATCCT TTGCGAATAC GCCCACGCGA TGGGTAACAG
        CTCTGCGCGG GCGACTAGGA AACGCTTATG CGGGTGCGCT ACCCATTGTC

+2        L   G   G   F   A   K   Y   W   Q   A   F   R   Q   Y   P   R
        ...................................................................
3001    TCTTGGCGGT TTCGCTAAAT ACTGGCAGGC GTTTCGTCAG TATCCCCGTT
        AGAACCGCCA AAGCGATTTA TGACCGTCCG CAAAGCAGTC ATAGGGGCAA

+2        L   Q   G   G   F   V   W   D   W   V   D   Q   S   L   I   K   Y
        ...................................................................
3051    TACAGGGCGG CTTCGTCTGG GACTGGGTGG ATCAGTCGCT GATTAAATAT
        ATGTCCCGCC GAAGCAGACC CTGACCCACC TAGTCAGCGA CTAATTTATA

+2        D   E   N   G   N   P   W   S   A   Y   G   G   D   F   G   D   T
        ...................................................................
3101    GATGAAAACG GCAACCCGTG GTCGGCTTAC GGCGGTGATT TTGGCGATAC
        CTACTTTTGC CGTTGGGCAC CAGCCGAATG CCGCCACTAA AACCGCTATG
```

FIG. 10H pICAST ALC

```
+2       P   N   D   R   Q   F   C   M   N   G   L   V   F   A   D   R
         .............................................................
3151     GCCGAACGAT CGCCAGTTCT GTATGAACGG TCTGGTCTTT GCCGACCGCA
         CGGCTTGCTA GCGGTCAAGA CATACTTGCC AGACCAGAAA CGGCTGGCGT

+2       T   P   H   P   A   L   T   E   A   K   H   Q   Q   Q   F   F   Q
         .............................................................
3201     CGCCGCATCC AGCGCTGACG GAAGCAAAAC ACCAGCAGCA GTTTTTCCAG
         GCGGCGTAGG TCGCGACTGC CTTCGTTTTG TGGTCGTCGT CAAAAAGGTC

+2         F   R   L   S   G   Q   T   I   E   V   T   S   E   Y   L   F   R
         .............................................................
3251     TTCCGTTTAT CCGGGCAAAC CATCGAAGTG ACCAGCGAAT ACCTGTTCCG
         AAGGCAAATA GGCCCGTTTG GTAGCTTCAC TGGTCGCTTA TGGACAAGGC

+2           H   S   D   N   E   L   L   H   W   M   V   A   L   D   G   K
         .............................................................
3301     TCATAGCGAT AACGAGCTCC TGCACTGGAT GGTGGCGCTG GATGGTAAGC
         AGTATCGCTA TTGCTCGAGG ACGTGACCTA CCACCGCGAC CTACCATTCG

+2         P   L   A   S   G   E   V   P   L   D   V   A   P   Q   G   K   Q
         .............................................................
3351     CGCTGGCAAG CGGTGAAGTG CCTCTGGATG TCGCTCCACA AGGTAAACAG
         GCGACCGTTC GCCACTTCAC GGAGACCTAC AGCGAGGTGT TCCATTTGTC

+2         L   I   E   L   P   E   L   P   Q   P   E   S   A   G   Q   L   W
         .............................................................
3401     TTGATTGAAC TGCCTGAACT ACCGCAGCCG GAGAGCGCCG GCAACTCTG
         AACTAACTTG ACGGACTTGA TGGCGTCGGC CTCTCGCGGC CCGTTGAGAC

+2         L   T   V   R   V   V   Q   P   N   A   T   A   W   S   E   A
         .............................................................
3451     GCTCACAGTA CGCGTAGTGC AACCGAACGC GACCGCATGG TCAGAAGCCG
         CGAGTGTCAT GCGCATCACG TTGGCTTGCG CTGGCGTACC AGTCTTCGGC
```

FIG. 10I pICAST ALC

```
+2      G  H  I  S   A  W  Q   Q  W  R   L   A  E  N   L  S  V
        ..................................................................

3501    GGCACATCAG CGCCTGGCAG CAGTGGCGTC TGGCGGAAAA CCTCAGTGTG
        CCGTGTAGTC GCGGACCGTC GTCACCGCAG ACCGCCTTTT GGAGTCACAC

+2         T  L  P  A   A  S  H   A  I  P   H  L  T   T  S  E  M
        ..................................................................

3551    ACGCTCCCCG CCGCGTCCCA CGCCATCCCG CATCTGACCA CCAGCGAAAT
        TGCGAGGGGC GGCGCAGGGT GCGGTAGGGC GTAGACTGGT GGTCGCTTTA

+2         D  F  C   I  E  L  G   N  K  R   W  Q  F   N  R  Q
        ..................................................................

3601    GGATTTTTGC ATCGAGCTGG GTAATAAGCG TTGGCAATTT AACCGCCAGT
        CCTAAAAACG TAGCTCGACC CATTATTCGC AACCGTTAAA TTGGCGGTCA

+2          S  G  F   L  S  Q  M   W  I  G   D  K  K   Q  L  L  T
        ..................................................................

3651    CAGGCTTTCT TTCACAGATG TGGATTGGCG ATAAAAAACA ACTGCTGACG
        GTCCGAAAGA AAGTGTCTAC ACCTAACCGC TATTTTTTGT TGACGACTGC

+2          P  L  R   D  Q  F   T  R  A  P   L  D  N   D  I  G  V
        ..................................................................

3701    CCGCTGCGCG ATCAGTTCAC CCGTGCACCG CTGGATAACG ACATTGGCGT
        GGCGACGCGC TAGTCAAGTG GGCACGTGGC GACCTATTGC TGTAACCGCA

+2          S  E  A   T  R  I   D  P  N   A  W  V  E   R  W  K
        ..................................................................

3751    AAGTGAAGCG ACCCGCATTG ACCCTAACGC CTGGGTCGAA CGCTGGAAGG
        TTCACTTCGC TGGGCGTAAC TGGGATTGCG GACCCAGCTT GCGACCTTCC

+2          A  A  G  H   Y  Q  A   E  A  A  L   L  Q  C   T  A  D
        ..................................................................

3801    CGGCGGGCCA TTACCAGGCC GAAGCAGCGT TGTTGCAGTG CACGGCAGAT
        GCCGCCCGGT AATGGTCCGG CTTCGTCGCA ACAACGTCAC GTGCCGTCTA
```

FIG. 10J pICAST ALC

```
+2       T  L  A  D  A  V  L  I  T  T  A  H  A  W  Q  H  Q
         ---------------------------------------------------
3851    ACACTTGCTG ATGCGGTGCT GATTACGACC GCTCACGCGT GGCAGCATCA
        TGTGAACGAC TACGCCACGA CTAATGCTGG CGAGTGCGCA CCGTCGTAGT

+2        G  K  T  L  F  I  S  R  K  T  Y  R  I  D  G  S
         ---------------------------------------------------
3901    GGGGAAAACC TTATTTATCA GCCGGAAAAC CTACCGGATT GATGGTAGTG
        CCCCTTTTGG AATAAATAGT CGGCCTTTTG GATGGCCTAA CTACCATCAC

+2        G  Q  M  A  I  T  V  D  V  E  V  A  S  D  T  P  H
         ---------------------------------------------------
3951    GTCAAATGGC GATTACCGTT GATGTTGAAG TGGCGAGCGA TACACCGCAT
        CAGTTTACCG CTAATGGCAA CTACAACTTC ACCGCTCGCT ATGTGGCGTA

+2        P  A  R  I  G  L  N  C  Q  L  A  Q  V  A  E  R  V
         ---------------------------------------------------
4001    CCGGCGCGGA TTGGCCTGAA CTGCCAGCTG GCGCAGGTAG CAGAGCGGGT
        GGCCGCGCCT AACCGGACTT GACGGTCGAC CGCGTCCATC GTCTCGCCCA

+2        N  W  L  G  L  G  P  Q  E  N  Y  P  D  R  L  T
         ---------------------------------------------------
4051    AAACTGGCTC GGATTAGGGC CGCAAGAAAA CTATCCCGAC CGCCTTACTG
        TTTGACCGAG CCTAATCCCG GCGTTCTTTT GATAGGGCTG GCGGAATGAC

+2        A  A  C  F  D  R  W  D  L  P  L  S  D  M  Y  T  P
         ---------------------------------------------------
4101    CCGCCTGTTT TGACCGCTGG GATCTGCCAT TGTCAGACAT GTATACCCCG
        GGCGGACAAA ACTGGCGACC CTAGACGGTA ACAGTCTGTA CATATGGGGC

+2        T  V  F  P  S  E  N  G  L  R  C  G  T  R  E  L  N
         ---------------------------------------------------
4151    TACGTCTTCC CGAGCGAAAA CGGTCTGCGC TGCGGGACGC GCGAATTGAA
        ATGCAGAAGG GCTCGCTTTT GCCAGACGCG ACGCCCTGCG CGCTTAACTT
```

FIG.10K pICAST ALC

```
+2         Y  G  P  H  Q  W  R  G  D  F  Q  F  N  I  S  R
           ....................................................
4201       TTATGGCCCA CACCAGTGGC GCGGCGACTT CCAGTTCAAC ATCAGCCGCT
           AATACCGGGT GTGGTCACCG CGCCGCTGAA GGTCAAGTTG TAGTCGGCGA

+2         Y  S  Q  Q  Q  L  M  E  T  S  H  R  H  L  L  H  A
           ....................................................
4251       ACAGTCAACA GCAACTGATG GAAACCAGCC ATCGCCATCT GCTGCACGCG
           TGTCAGTTGT CGTTGACTAC CTTTGGTCGG TAGCGGTAGA CGACGTGCGC

+2           E  E  G  T  W  L  N  I  D  G  F  H  M  G  I  G  G
           ....................................................
4301       GAAGAAGGCA CATGGCTGAA TATCGACGGT TTCCATATGG GGATTGGTGG
           CTTCTTCCGT GTACCGACTT ATAGCTGGCA AAGGTATACC CCTAACCACC

+2            D  D  S  W  S  P  S  V  S  A  E  F  Q  L  S  A
           ....................................................
4351       CGACGACTCC TGGAGCCCGT CAGTATCGGC GGAATTCCAG CTGAGCGCCG
           GCTGCTGAGG ACCTCGGGCA GTCATAGCCG CCTTAAGGTC GACTCGCGGC

+2         G  R  Y  H  Y  Q  L  V  W  C  Q  K  R  S  D  Y  K
           ....................................................
4401       GTCGCTACCA TTACCAGTTG GTCTGGTGTC AAAAAAGATC TGACTATAAA
           CAGCGATGGT AATGGTCAAC CAGACCACAG TTTTTTCTAG ACTGATATTT

+2         D  E  D  L  D  H  H  H  H  H  R
           -------------------------------->
4451       GATGAGGACC TCGACCATCA TCATCATCAT CACCGGTAAT AATAGGTAGA
           CTACTCCTGG AGCTGGTAGT AGTAGTAGTA GTGGCCATTA TTATCCATCT

4501       TAAGTGACTG ATTAGATGCA TTGATCCCTC GACCAATTCC GGTTATTTTC
           ATTCACTGAC TAATCTACGT AACTAGGGAG CTGGTTAAGG CCAATAAAAG

4551       CACCATATTG CCGTCTTTTG GCAATGTGAG GGCCCGGAAA CCTGGCCCTG
           GTGGTATAAC GGCAGAAAAC CGTTACACTC CCGGGCCTTT GGACCGGGAC
```

FIG. 10L pICAST ALC

```
4601  TCTTCTTGAC GAGCATTCCT AGGGGTCTTT CCCCTCTCGC CAAAGGAATG
      AGAAGAACTG CTCGTAAGGA TCCCCAGAAA GGGGAGAGCG GTTTCCTTAC

4651  CAAGGTCTGT TGAATGTCGT GAAGGAAGCA GTTCCTCTGG AAGCTTCTTG
      GTTCCAGACA ACTTACAGCA CTTCCTTCGT CAAGGAGACC TTCGAAGAAC

4701  AAGACAAACA ACGTCTGTAG CGACCCTTTG CAGGCAGCGG AACCCCCAC
      TTCTGTTTGT TGCAGACATC GCTGGGAAAC GTCCGTCGCC TTGGGGGGTG

4751  CTGGCGACAG GTGCCTCTGC GGCCAAAAGC CACGTGTATA AGATACACCT
      GACCGCTGTC CACGGAGACG CCGGTTTTCG GTGCACATAT TCTATGTGGA

4801  GCAAAGGCGG CACAACCCCA GTGCCACGTT GTGAGTTGGA TAGTTGTGGA
      CGTTTCCGCC GTGTTGGGGT CACGGTGCAA CACTCAACCT ATCAACACCT

4851  AAGAGTCAAA TGGCTCTCCT CAAGCGTATT CAACAAGGGG CTGAAGGATG
      TTCTCAGTTT ACCGAGAGGA GTTCGCATAA GTTGTTCCCC GACTTCCTAC

4901  CCCAGAAGGT ACCCCATTGT ATGGGATCTG ATCTGGGGCC TCGGTGCACA
      GGGTCTTCCA TGGGGTAACA TACCCTAGAC TAGACCCCGG AGCCACGTGT

4951  TGCTTTACAT GTGTTTAGTC GAGGTTAAAA AACGTCTAGG CCCCCCGAAC
      ACGAAATGTA CACAAATCAG CTCCAATTTT TTGCAGATCC GGGGGGCTTG

5001  CACGGGGACG TGGTTTTCCT TTGAAAAACA CGATGATAAT ACCATGATTG
      GTGCCCCTGC ACCAAAAGGA AACTTTTTGT GCTACTATTA TGGTACTAAC

5051  AACAAGATGG ATTGCACGCA GGTTCTCCGG CCGCTTGGGT GGAGAGGCTA
      TTGTTCTACC TAACGTGCGT CCAAGAGGCC GGCGAACCCA CCTCTCCGAT

5101  TTCGGCTATG ACTGGGCACA ACAGACAATC GGCTGCTCTG ATGCCGCCGT
      AAGCCGATAC TGACCCGTGT TGTCTGTTAG CCGACGAGAC TACGGCGGCA

5151  GTTCCGGCTG TCAGCGCAGG GGCGCCCGGT TCTTTTTGTC AAGACCGACC
      CAAGGCCGAC AGTCGCGTCC CCGCGGGCCA AGAAAAACAG TTCTGGCTGG
```

FIG. 10M pICAST ALC

```
5201   TGTCCGGTGC CCTGAATGAA CTGCAGGACG AGGCAGCGCG GCTATCGTGG
       ACAGGCCACG GGACTTACTT GACGTCCTGC TCCGTCGCGC CGATAGCACC

5251   CTGGCCACGA CGGGCGTTCC TTGCGCAGCT GTGCTCGACG TTGTCACTGA
       GACCGGTGCT GCCCGCAAGG AACGCGTCGA CACGAGCTGC AACAGTGACT

5301   AGCGGGAAGG GACTGGCTGC TATTGGGCGA AGTGCCGGGG CAGGATCTCC
       TCGCCCTTCC CTGACCGACG ATAACCCGCT TCACGGCCCC GTCCTAGAGG

5351   TGTCATCTCA CCTTGCTCCT GCCGAGAAAG TATCCATCAT GGCTGATGCA
       ACAGTAGAGT GGAACGAGGA CGGCTCTTTC ATAGGTAGTA CCGACTACGT

5401   ATGCGGCGGC TGCATACGCT TGATCCGGCT ACCTGCCCAT TCGACCACCA
       TACGCCGCCG ACGTATGCGA ACTAGGCCGA TGGACGGGTA AGCTGGTGGT

5451   AGCGAAACAT CGCATCGAGC GAGCACGTAC TCGGATGGAA GCCGGTCTTG
       TCGCTTTGTA GCGTAGCTCG CTCGTGCATG AGCCTACCTT CGGCCAGAAC

5501   TCGATCAGGA TGATCTGGAC GAAGAGCATC AGGGGCTCGC GCCAGCCGAA
       AGCTAGTCCT ACTAGACCTG CTTCTCGTAG TCCCCGAGCG CGGTCGGCTT

5551   CTGTTCGCCA GGCTCAAGGC GCGCATGCCC GACGGCGAGG ATCTCGTCGT
       GACAAGCGGT CCGAGTTCCG CGCGTACGGG CTGCCGCTCC TAGAGCAGCA

5601   GACCCATGGC GATGCCTGCT TGCCGAATAT CATGGTGGAA AATGGCCGCT
       CTGGGTACCG CTACGGACGA ACGGCTTATA GTACCACCTT TTACCGGCGA

5651   TTTCTGGATT CATCGACTGT GGCCGGCTGG GTGTGGCGGA CCGCTATCAG
       AAAGACCTAA GTAGCTGACA CCGGCCGACC CACACCGCCT GGCGATAGTC

5701   GACATAGCGT TGGCTACCCG TGATATTGCT GAAGAGCTTG GCGGCGAATG
       CTGTATCGCA ACCGATGGGC ACTATAACGA CTTCTCGAAC CGCCGCTTAC

5751   GGCTGACCGC TTCCTCGTGC TTTACGGTAT CGCCGCTCCC GATTCGCAGC
       CCGACTGGCG AAGGAGCACG AAATGCCATA GCGGCGAGGG CTAAGCGTCG
```

FIG.10N pICAST ALC

```
5801  GCATCGCCTT CTATCGCCTT CTTGACGAGT TCTTCTGAGC GGGACTCTGG
      CGTAGCGGAA GATAGCGGAA GAACTGCTCA AGAAGACTCG CCCTGAGACC

5851  GGTTCGCATC GATAAAATAA AAGATTTTAT TTAGTCTCCA GAAAAAGGGG
      CCAAGCGTAG CTATTTTATT TTCTAAAATA AATCAGAGGT CTTTTTCCCC

5901  GGAATGAAAG ACCCCACCTG TAGGTTTGGC AAGCTAGCTT AAGTAACGCC
      CCTTACTTTC TGGGGTGGAC ATCCAAACCG TTCGATCGAA TTCATTGCGG

5951  ATTTTGCAAG GCATGGAAAA ATACATAACT GAGAATAGAG AAGTTCAGAT
      TAAAACGTTC CGTACCTTTT TATGTATTGA CTCTTATCTC TTCAAGTCTA

6001  CAAGGTCAGG AACAGATGGA ACAGCTGAAT ATGGGCCAAA CAGGATATCT
      GTTCCAGTCC TTGTCTACCT TGTCGACTTA TACCCGGTTT GTCCTATAGA

6051  GTGGTAAGCA GTTCCTGCCC CGGCTCAGGG CCAAGAACAG ATGGAACAGC
      CACCATTCGT CAAGGACGGG GCCGAGTCCC GGTTCTTGTC TACCTTGTCG

6101  TGAATATGGG CCAAACAGGA TATCTGTGGT AAGCAGTTCC TGCCCCGGCT
      ACTTATACCC GGTTTGTCCT ATAGACACCA TTCGTCAAGG ACGGGGCCGA

6151  CAGGGCCAAG AACAGATGGT CCCCAGATGC GGTCCAGCCC TCAGCAGTTT
      GTCCCGGTTC TTGTCTACCA GGGGTCTACG CCAGGTCGGG AGTCGTCAAA

6201  CTAGAGAACC ATCAGATGTT TCCAGGGTGC CCCAAGGACC TGAAATGACC
      GATCTCTTGG TAGTCTACAA AGGTCCCACG GGGTTCCTGG ACTTTACTGG

6251  CTGTGCCTTA TTTGAACTAA CCAATCAGTT CGCTTCTCGC TTCTGTTCGC
      GACACGGAAT AAACTTGATT GGTTAGTCAA GCGAAGAGCG AAGACAAGCG

6301  GCGCTTCTGC TCCCCGAGCT CAATAAAAGA GCCCACAACC CCTCACTCGG
      CGCGAAGACG AGGGGCTCGA GTTATTTTCT CGGGTGTTGG GGAGTGAGCC

6351  GGCGCCAGTC CTCCGATTGA CTGAGTCGCC CGGGTACCCG TGTATCCAAT
      CCGCGGTCAG GAGGCTAACT GACTCAGCGG GCCCATGGGC ACATAGGTTA
```

FIG. 100 pICAST ALC

6401 AAACCCTCTT GCAGTTGCAT CCGACTTGTG GTCTCGCTGT TCCTTGGGAG
     TTTGGGAGAA CGTCAACGTA GGCTGAACAC CAGAGCGACA AGGAACCCTC

6451 GGTCTCCTCT GAGTGATTGA CTACCCGTCA GCGGGGGTCT TTCATTCATG
     CCAGAGGAGA CTCACTAACT GATGGGCAGT CGCCCCCAGA AAGTAAGTAC

6501 CAGCATGTAT CAAAATTAAT TTGGTTTTTT TTCTTAAGTA TTTACATTAA
     GTCGTACATA GTTTTAATTA AACCAAAAAA AAGAATTCAT AAATGTAATT

6551 ATGGCCATAG TTGCATTAAT GAATCGGCCA ACGCGCGGGG AGAGGCGGTT
     TACCGGTATC AACGTAATTA CTTAGCCGGT TGCGCGCCCC TCTCCGCCAA

6601 TGCGTATTGG CGCTCTTCCG CTTCCTCGCT CACTGACTCG CTGCGCTCGG
     ACGCATAACC GCGAGAAGGC GAAGGAGCGA GTGACTGAGC GACGCGAGCC

6651 TCGTTCGGCT GCGGCGAGCG GTATCAGCTC ACTCAAAGGC GGTAATACGG
     AGCAAGCCGA CGCCGCTCGC CATAGTCGAG TGAGTTTCCG CCATTATGCC

FIG.1OP pICAST ALN

```
CTGCAGCCTG AATATGGGCC AAACAGGATA TCTGTGGTAA GCAGTTCCTG CCCCGGCTCA    60
GACGTCGGAC TTATACCCGG TTTGTCCTAT AGACACCATT CGTCAAGGAC GGGGCCGAGT    60

GGGCCAAGAA CAGATGGAAC AGCTGAATAT GGGCCAAACA GGATATCTGT GGTAAGCAGT   120
CCCGGTTCTT GTCTACCTTG TCGACTTATA CCCGGTTTGT CCTATAGACA CCATTCGTCA   120

TCCTGCCCCG GCTCAGGGCC AAGAACAGAT GGTCCCCAGA TGCGGTCCAG CCCTCAGCAG   180
AGGACGGGGC CGAGTCCCGG TTCTTGTCTA CCAGGGGTCT ACGCCAGGTC GGGAGTCGTC   180

TTTCTAGAGA ACCATCAGAT GTTTCCAGGG TGCCCCAAGG ACCTGAAATG ACCCTGTGCC   240
AAAGATCTCT TGGTAGTCTA CAAAGGTCCC ACGGGGTTCC TGGACTTTAC TGGGACACGG   240

TTATTTGAAC TAACCAATCA GTTCGCTTCT CGCTTCTGTT CGCGCGCTTC TGCTCCCCGA   300
AATAAACTTG ATTGGTTAGT CAAGCGAAGA GCGAAGACAA GCGCGCGAAG ACGAGGGGCT   300

GCTCAATAAA AGAGCCCACA ACCCGTCACT CGGGGCGCCA GTCCTCCGAT TGACTGAGTC   360
CGAGTTATTT TCTCGGGTGT TGGGGAGTGA GCCCGCGGT CAGGAGGCTA ACTGACTCAG    360

GCCCGGGTAC CCGTGTATCC AATAAACCCT CTTGCAGTTG CATCCGACTT GTGGTCTCGC   420
CGGGCCCATG GGCACATAGG TTATTTGGGA GAACGTCAAC GTAGGCTGAA CACCAGAGCG   420

TGTTCCTTGG GAGGGTCTCC TCTGAGTGAT TGACTACCCG TCAGCGGGGG TCTTTCATTT   480
ACAAGGAACC CTCCCAGAGG AGACTCACTA ACTGATGGGC AGTCGCCCCC AGAAAGTAAA   480

GGGGGCTCGT CCGGGATCGG GAGACCCCTG CCCAGGGACC ACCGACCCAC CACCGGGAGG   540
CCCCCGAGCA GGCCCTAGCC CTCTGGGGAC GGGTCCCTGG TGGCTGGGTG GTGGCCCTCC   540

CAAGCTGGCC AGCAACTTAT CTGTGTCTGT CCGATTGTCT AGTGTCTATG ACTGATTTTA   600
GTTCGACCGG TCGTTGAATA GACACAGACA GGCTAACAGA TCACAGATAC TGACTAAAAT   600

TGCGCCTGCG TCGGTACTAG TTAGCTAACT AGCTCTGTAT CTGGCGGACC CGTGGTGGAA   660
ACGCGGACGC AGCCATGATC AATCGATTGA TCGAGACATA GACCGCCTGG GCACCACCTT   660

CTGACGAGTT CTGAACACCC GGCCGCAACC CTGGGAGACG TCCCAGGGAC TTTGGGGGCC   720
GACTGCTCAA GACTTGTGGG CCGGCGTTGG GACCCTCTGC AGGGTCCCTG AAACCCCCGG   720

GTTTTTGTGG CCCGACCTGA GGAAGGGAGT CGATGTGGAA TCCGACCCCG TCAGGATATG   780
CAAAAACACC GGGCTGGACT CCTTCCCTCA GCTACACCTT AGGCTGGGGC AGTCCTATAC   780
```

FIG.11B pICAST ALN

```
TGGTTCTGGT AGGAGACGAG AACCTAAAAC AGTTCCCGCC TCCGTCTGAA TTTTTGCTTT   840
ACCAAGACCA TCCTCTGCTC TTGGATTTTG TCAAGGGCGG AGGCAGACTT AAAAACGAAA   840

CGGTTTGGAA CCGAAGCCGC GCGTCTTGTC TGCTGCAGCA TCGTTCTGTG TTGTCTCTGT   900
GCCAAACCTT GGCTTCGGCG CGCAGAACAG ACGACGTCGT AGCAAGACAC AACAGAGACA   900

CTGACTGTGT TTCTGTATTT GTCTGAAAAT TAGGGCCAGA CTGTTACCAC TCCCTTAAGT   960
GACTGACACA AAGACATAAA CAGACTTTTA ATCCCGGTCT GACAATGGTG AGGGAATTCA   960

TTGACCTTAG GTAACTGGAA AGATGTCGAG CGGCTCGCTC ACAACCAGTC GGTAGATGTC  1020
AACTGGAATC CATTGACCTT TCTACAGCTC GCCGAGCGAG TGTTGGTCAG CCATCTACAG  1020

AAGAAGAGAC GTTGGGTTAC CTTCTGCTCT GCAGAATGGC CAACCTTTAA CGTCGGATGG  1080
TTCTTCTCTG CAACCCAATG GAAGACGAGA CGTCTTACCG GTTGGAAATT GCAGCCTACC  1080

CCGCGAGACG GCACCTTTAA CCGAGACCTC ATCACCCAGG TTAAGATCAA GGTCTTTTCA  1140
GGCGCTCTGC CGTGGAAATT GGCTCTGGAG TAGTGGGTCC AATTCTAGTT CCAGAAAAGT  1140

CCTGGCCCGC ATGGACACCC AGACCAGGTC CCCTACATCG TGACCTGGGA AGCCTTGGCT  1200
GGACCGGGCG TACCTGTGGG TCTGGTCCAG GGGATGTAGC ACTGGACCCT TCGGAACCGA  1200

TTTGACCCCC CTCCCTGGGT CAAGCCCTTT GTACACCCTA AGCCTCCGCC TCCTCTTCCT  1260
AAACTGGGGG GAGGGACCCA GTTCGGGAAA CATGTGGGAT TCGGAGGCGG AGGAGAAGGA  1260

CCATCCGCCC CGTCTCTCCC CCTTGAACCT CCTCGTTCGA CCCCGCCTCG ATCCTCCCTT  1320
GGTAGGCGGG GCAGAGAGGG GGAACTTGGA GGAGCAAGCT GGGGCGGAGC TAGGAGGGAA  1320

TATCCAGCCC TCACTCCTTC TCTAGGCGCC GGCCGCTCTA GCCCATTAAT ACGACTCACT  1380
ATAGGTCGGG AGTGAGGAAG AGATCCGCGG CCGGCGAGAT CGGGTAATTA TGCTGAGTGA  1380

ATAGGGCGAT TCGAACACCA TGCACCATCA TCATCATCAC GTCGACTATA AAGATGAGGA  1440
TATCCCGCTA AGCTTGTGGT ACGTGGTAGT AGTAGTAGTG CAGCTGATAT TTCTACTCCT  1440

CCTCGAGATG GGCGTGATTA CGGATTCACT GGCCGTCGTG GCCCGCACCG ATCGCCCTTC  1500
GGAGCTCTAC CCGCACTAAT GCCTAAGTGA CCGGCAGCAC CGGGCGTGGC TAGCGGGAAG  1500

CCAACAGTTA CGCAGCCTGA ATGGCGAATG GCGCTTTGCC TGGTTTCCGG CACCAGAAGC  1560
GGTTGTCAAT GCGTCGGACT TACCGCTTAC CGCGAAACGG ACCAAAGGCC GTGGTCTTCG  1560
```

FIG. 11C pICAST ALN

```
GGTGCCGGAA AGCTGGCTGG AGTGCGATCT TCCTGAGGCC GATACTGTCG TCGTCCCCTC  1620
CCACGGCCTT TCGACCGACC TCACGCTAGA AGGACTCCGG CTATGACAGC AGCAGGGGAG  1620

AAACTGGCAG ATGCACGGTT ACGATGCGCC CATCTACACC AACGTGACCT ATCCCATTAC  1680
TTTGACCGTC TACGTGCCAA TGCTACGCGG GTAGATGTGG TTGCACTGGA TAGGGTAATG  1680

GGTCAATCCG CCGTTTGTTC CCACGGAGAA TCCGACGGGT TGTTACTCGC TCACATTTAA  1740
CCAGTTAGGC GGCAAACAAG GGTGCCTCTT AGGCTGCCCA ACAATGAGCG AGTGTAAATT  1740

TGTTGATGAA AGCTGGCTAC AGGAAGGCCA GACGCGAATT ATTTTTGATG GCGTTAACTC  1800
ACAACTACTT TCGACCGATG TCCTTCCGGT CTGCGCTTAA TAAAAACTAC CGCAATTGAG  1800

GGCGTTTCAT CTGTGGTGCA ACGGGCGCTG GGTCGGTTAC GGCCAGGACA GTCGTTTGCC  1860
CCGCAAAGTA GACACCACGT TGCCCGCGAC CCAGCCAATG CCGGTCCTGT CAGCAAACGG  1860

GTCTGAATTT GACCTGAGCG CATTTTTACG CGCCGGAGAA AACCGCCTCG CGGTGATGGT  1920
CAGACTTAAA CTGGACTCGC GTAAAAATGC GCGGCCTCTT TTGGCGGAGC GCCACTACCA  1920

GCTGGGCTGG AGTGACGGCA GTTATCTGGA AGATCAGGAT ATGTGGCGGA TGAGCGGCAT  1980
CGACGCGACC TCACTGCCGT CAATAGACCT TCTAGTCCTA TACACCGCCT ACTCGCCGTA  1980

TTTCCGTGAC GTCTCGTTGC TGCATAAACC GACTACACAA ATCAGCGATT TCCATGTTGC  2040
AAAGGCACTG CAGAGCAACG ACGTATTTGG CTGATGTGTT TAGTCGCTAA AGGTACAACG  2040

CACTCGCTTT AATGATGATT RCAGCCGCGC TGTACTGGAG GCTGAAGTTC AGATGTGCGG  2100
GTGAGCGAAA TTACTACTAA AGTCGGCGCG ACATGACCTC CGACTTCAAG TCTACACGCC  2100

CGAGTTGCGT GACTACCTAC GGGTAACAGT TTCTTTATGG CAGGGTGAAA CGCAGGTCGC  2160
GCTCAACGCA CTGATGGATG CCCATTGTCA AAGAAATACC GTCCCACTTT GCGTCCAGCG  2160

CAGCGGCACC GCGCCTTTCG GCGGTGAAAT TATCGATGAG CGTGGTGGTT ATGCCGATCG  2220
GTCGCCGTGG CGCGGAAAGC CGCCACTTTA ATAGCTACTC GCACCACCAA TACGGCTAGC  2220

CGTCACACTA CGTCTGAACG TCGAAAACCC GAAACTGTGG AGCGCCGAAA TCCCGAATCT  2280
GCAGTGTGAT GCAGACTTGC AGCTTTTGGG CTTTGACACC TCGCGGCTTT AGGGCTTAGA  2280

CTATCGTGCG GTGGTTGAAC TGCACACCGC CGACGGCACG CTGATTGAAG CAGAAGCCTG  2340
GATAGCACGC CACCAACTTG ACGTGTGGCG GCTGCCGTGC GACTAACTTC GTCTTCGGAC  2340
```

FIG.11D pICAST ALN

```
CGATGTCGGT TTCCGCGAGG TGCGGATTGA AAATGGTCTG CTGCTGCTGA ACGGCAAGCC    2400
GCTACAGCCA AAGGCGCTCC ACGCCTAACT TTTACCAGAC GACGACGACT TGCCGTTCGG    2400

GTTGCTGATT CGAGGCGTTA ACCGTCACGA GCATCATCCT CTGCATGGTC AGGTCATGGA    2460
CAACGACTAA GCTCCGCAAT TGGCAGTGCT CGTAGTAGGA GACGTACCAG TCCAGTACCT    2460

TGAGCAGACG ATGGTGCAGG ATATCCTGCT GATGAAGCAG AACAACTTTA ACGCCGTGCG    2520
ACTCGTCTGC TACCACGTCC TATAGGACGA CTACTTCGTC TTGTTGAAAT TGCGGCACGC    2520

CTGTTCGCAT TATCCGAACC ATCCGCTGTG GTACACGCTG TGCGACCGCT ACGGCCTGTA    2580
GACAAGCGTA ATAGGCTTGG TAGGCGACAC CATGTGCGAC ACGCTGGCGA TGCCGGACAT    2580

TGTGGTGGAT GAAGCCAATA TTGAAACCCA CGGCATGGTG CCAATGAATC GTCTGACCGA    2640
ACACCACCTA CTTCGGTTAT AACTTTGGGT GCCGTACCAC GGTTACTTAG CAGACTGGCT    2640

TGATCCGCGC TGGCTACCGG CGATGAGCGA ACGCGTAACG CGAATGGTGC AGCGCGATCG    2700
ACTAGGCGCG ACCGATGGCC GCTACTCGCT TGCGCATTGC GCTTACCACG TCGCGCTAGC    2700

TAATCACCCG AGTGTGATCA TCTGGTCGCT GGGGAATGAA TCAGGCCACG GCGCTAATCA    2760
ATTAGTGGGC TCACACTAGT AGACCAGCGA CCCCTTACTT AGTCCGGTGC CGCGATTAGT    2760

CGACGCGCTG TATCGCTGGA TCAAATCTGT CGATCCTTCC CGCCCGGTGC AGTATGAAGG    2820
GCTGCGCGAC ATAGCGACCT AGTTTAGACA GCTAGGAAGG GCGGGCCACG TCATACTTCC    2820

CGGCGGAGCC GACACCACGG CCACCGATAT TATTTGCCCG ATGTACGCGC GCGTGGATGA    2880
GCCGCCTCGG CTGTGGTGCC GGTGGCTATA ATAAACGGGC TACATGCGCG CGCACCTACT    2880

AGACCAGCCC TTCCCGGCTG TGCCGAAATG GTCCATCAAA AAATGGCTTT CGCTACCTGG    2940
TCTGGTCGGG AAGGGCCGAC ACGGCTTTAC CAGGTAGTTT TTTACCGAAA GCGATGGACC    2940

AGAGACGCGC CCGCTGATCC TTTGCGAATA CGCCCACGCG ATGGGTAACA GTCTTGGCGG    3000
TCTCTGCGCG GGCGACTAGG AAACGCTTAT GCGGGTGCGC TACCCATTGT CAGAACCGCC    3000

TTTCGCTAAA TACTGGCAGG CGTTTCGTCA GTATCCCCGT TTACAGGGCG GCTTCGTCTG    3060
AAAGCGATTT ATGACCGTCC GCAAAGCAGT CATAGGGGCA AATGTCCCGC CGAAGCAGAC    3060

GGACTGGGTG GATCAGTCGC TGATTAAATA TGATGAAAAC GGCAACCCGT GGTCGGCTTA    3120
CCTGACCCAC CTAGTCAGCG ACTAATTTAT ACTACTTTTG CCGTTGGGCA CCAGCCGAAT    3120
```

FIG.11E pICAST ALN

```
CGGCGGTGAT TTTGGCGATA CGCCGAACGA TCGCCAGTTC TGTATGAACG GTCTGGTCTT    3180
GCCGCCACTA AAACCGCTAT GCGGCTTGCT AGCGGTCAAG ACATACTTGC CAGACCAGAA    3180

TGCCGACCGC ACGCCGCATC CAGCGCTGAC GGAAGCAAAA CACCAGCAGC AGTTTTTCCA    3240
ACGGCTGGCG TGCGGCGTAG GTCGCGACTG CCTTCGTTTT GTGGTCGTCG TCAAAAAGGT    3240

GTTCCGTTTA TCCGGGCAAA CCATCGAAGT GACCAGCGAA TACCTGTTCC GTCATAGCGA    3300
CAAGGCAAAT AGGCCCGTTT GGTAGCTTCA CTGGTCGCTT ATGGACAAGG CAGTATCGCT    3300

TAACGAGCTC CTGCACTGGA TGGTGGCGCT GGATGGTAAG CCGCTGGCAA GCGGTGAAGT    3360
ATTGCTCGAG GACGTGACCT ACCACCGCGA CCTACCATTC GGCGACCGTT CGCCACTTCA    3360

GCCTCTGGAT GTCGCTCCAC AAGGTAAACA GTTGATTGAA CTGCCTGAAC TACCGCAGCC    3420
CGGAGACCTA CAGCGAGGTG TTCCATTTGT CAACTAACTT GACGGACTTG ATGGCGTCGG    3420

GGAGAGCGCC GGGCAACTCT GGCTCACAGT ACGCGTAGTG CAACCGAACG CGACCGCATG    3480
CCTCTCGCGG CCCGTTGAGA CCGAGTGTCA TGCGCATCAC GTTGGCTTGC GCTGGCGTAC    3480

GTCAGAAGCC GGGCACATCA GCGCCTGGCA GCAGTGGCGT CTGGCGGAAA ACCTCAGTGT    3540
CAGTCTTCGG CCCGTGTAGT CGCGGACCGT CGTCACCGCA GACCGCCTTT TGGAGTCACA    3540

GACGCTCCCC GCCGCGTCCC ACGCCATCCC GCATCTGACC ACCAGCGAAA TGGATTTTTG    3600
CTGCGAGGGG CGGCGCAGGG TGCGGTAGGG CGTAGACTGG TGGTCGCTTT ACCTAAAAAC    3600

CATCGAGCTG GGTAATAAGC GTTGGCAATT TAACCGCCAG TCAGGCTTTC TTTCACAGAT    3660
GTAGCTCGAC CCATTATTCG CAACCGTTAA ATTGGCGGTC AGTCCGAAAG AAAGTGTCTA    3660

GTGGATTGGC GATAAAAAAC AACTGCTGAC GCCGCTGCGC GATCAGTTCA CCCGTGCACC    3720
CACCTAACCG CTATTTTTTG TTGACGACTG CGGCGACGCG CTAGTCAAGT GGGCACGTGG    3720

GCTGGATAAC GACATTGGCG TAAGTGAAGC GACCCGCATT GACCCTAACG CCTGGGTCGA    3780
CGACCTATTG CTGTAACCGC ATTCACTTCG CTGGGCGTAA CTGGGATTGC GGACCCAGCT    3780

ACGCTGGAAG GCGGCGGGCC ATTACCAGGC CGAAGCAGCG TTGTTGCAGT GCACGGCAGA    3840
TGCGACCTTC CGCCGCCCGG TAATGGTCCG GCTTCGTCGC AACAACGTCA CGTGCCGTCT    3840

TACACTTGCT GATGCGGTGC TGATTACGAC CGCTCACGCG TGGCAGCATC AGGGGAAAAC    3900
ATGTGAACGA CTACGCCACG ACTAATGCTG GCGAGTGCGC ACCGTCGTAG TCCCCTTTTG    3900
```

FIG.11F pICAST ALN

```
CTTATTTATC AGCCGGAAAA CCTACCGGAT TGATGGTAGT GGTCAAATGG CGATTACCGT    3960
GAATAAATAG TCGGCCTTTT GGATGGCCTA ACTACCATCA CCAGTTTACC GCTAATGGCA    3960

TGATGTTGAA GTGGCGAGCG ATACACCGCA TCCGGCGCGG ATTGGCCTGA ACTGCCAGCT    4020
ACTACAACTT CACCGCTCGC TATGTGGCGT AGGCCGCGCC TAACCGGACT TGACGGTCGA    4020

GGCGCAGGTA GCAGAGCGGG TAAACTGGCT CGGATTAGGG CCGCAAGAAA ACTATCCCGA    4080
CCGCGTCCAT CGTCTCGCCC ATTTGACCGA GCCTAATCCC GGCGTTCTTT TGATAGGGCT    4080

CCGCCTTACT GCCGCCTGTT TTGACCGCTG GGATCTGCCA TTGTCAGACA TGTATACCCC    4140
GGCGGAATGA CGGCGGACAA AACTGGCGAC CCTAGACGGT AACAGTCTGT ACATATGGGG    4140

GTACGTCTTC CCGAGCGAAA ACGGTCTGCG CTGCGGGACG CGCGAATTGA ATTATGGCCC    4200
CATGCAGAAG GGCTCGCTTT TGCCAGACGC GACGCCCTGC GCGCTTAACT TAATACCGGG    4200

ACACCAGTGG CGCGGCGACT TCCAGTTCAA CATCAGCCGC TACAGTCAAC AGCAACTGAT    4260
TGTGGTCACC GCGCCGCTGA AGGTCAAGTT GTAGTCGGCG ATGTCAGTTG TCGTTGACTA    4260

GGAAACCAGC CATCGCCATC TGCTGCACGC GGAAGAAGGC ACATGGCTGA ATATCGACGG    4320
CCTTTGGTCG GTAGCGGTAG ACGACGTGCG CCTTCTTCCG TGTACCGACT TATAGCTGCC    4320

TTTCCATATG GGGATTGGTG GCGACGACTC CTGGAGCCCG TCAGTATCGG CGGAATTCCA    4380
AAAGGTATAC CCCTAACCAC CGCTGCTGAG GACCTCGGGC AGTCATAGCC GCCTTAAGGT    4380

GCTGAGCGCC GGTCGCTACC ATTACCAGTT GGTCTGGTGT CAAAAAAGAT CTGGAGGTGG    4440
CGACTCGCGG CCAGCGATGG TAATGGTCAA CCAGACCACA GTTTTTTCTA GACCTCCACC    4440

TGGCAGCAGG CCTTGGCGCG CCGGATCCTT AATTAACAAT TGACCGGTAA TAATAGGTAG    4500
ACCGTCGTCC GGAACCGCGC GGCCTAGGAA TTAATTGTTA ACTGGCCATT ATTATCCATC    4500

ATAAGTGACT GATTAGATGC ATTGATCCCT CGACCAATTC CGGTTATTTT CCACCATATT    4560
TATTCACTGA CTAATCTACG TAACTAGGGA GCTGGTTAAG GCCAATAAAA GGTGGTATAA    4560

GCCGTCTTTT GGCAATGTGA GGGCCCGGAA ACCTGGCCCT GTCTTCTTGA CGAGCATTCC    4620
CGGCAGAAAA CCGTTACACT CCCGGGCCTT TGGACCGGGA CAGAAGAACT GCTCGTAAGG    4620

TAGGGGTCTT TCCCCTCTCG CCAAAGGAAT GCAAGGTCTG TTGAATGTCG TGAAGGAAGC    4680
ATCCCCAGAA AGGGGAGAGC GGTTTCCTTA CGTTCCAGAC AACTTACAGC ACTTCCTTCG    4680
```

FIG. 11G pICAST ALN

```
AGTTCCTCTG GAAGCTTCTT GAAGACAAAC AACGTCTGTA GCGACCCTTT GCAGGCAGCG   4740
TCAAGGAGAC CTTCGAAGAA CTTCTGTTTG TTGCAGACAT CGCTGGGAAA CGTCCGTCGC   4740

GAACCCCCCA CCTGGCGACA GGTGCCTCTG CGGCCAAAAG CCACGTGTAT AAGATACACC   4800
CTTGGGGGGT GGACCGCTGT CCACGGAGAC GCCGGTTTTC GGTGCACATA TTCTATGTGG   4800

TGCAAAGGCG GCACAACCCC AGTGCCACGT TGTGAGTTGG ATAGTTGTGG AAAGAGTCAA   4860
ACGTTTCCGC CGTGTTGGGG TCACGGTGCA ACACTCAACC TATCAACACC TTTCTCAGTT   4860

ATGGCTCTCC TCAAGCGTAT TCAACAAGGG GCTGAAGGAT GCCCAGAAGG TACCCCATTG   4920
TACCGAGAGG AGTTCGCATA AGTTGTTCCC CGACTTCCTA CGGGTCTTCC ATGGGGTAAC   4920

TATGGGATCT GATCTGGGGC CTCGGTGCAC ATGCTTTACA TGTGTTTAGT CGAGGTTAAA   4980
ATACCCTAGA CTAGACCCCG GAGCCACGTG TACGAAATGT ACACAAATCA GCTCCAATTT   4980

AAACGTCTAG GCCCCCCGAA CCACGGGGAC GTGGTTTTCC TTTGAAAAAC ACGATGATAA   5040
TTTGCAGATC CGGGGGGCTT GGTGCCCCTG CACCAAAAGG AAACTTTTTG TGCTACTATT   5040

TACCATGATT GAACAAGATG GATTGCACGC AGGTTCTCCG GCCGCTTGGG TGGAGAGGCT   5100
ATGGTACTAA CTTGTTCTAC CTAACGTGCG TCCAAGAGGC CGGCGAACCC ACCTCTCCGA   5100

ATTCGGCTAT GACTGGGCAC AACAGACAAT CGGCTGCTCT GATGCCGCCG TGTTCCGGCT   5160
TAAGCCGATA CTGACCCGTG TTGTCTGTTA GCCGACGAGA CTACGGCGGC ACAAGGCCGA   5160

GTCAGCGCAG GGGCGCCCGG TTCTTTTTGT CAAGACCGAC CTGTCCGGTG CCCTGAATGA   5220
CAGTCGCGTC CCCGCGGGCC AAGAAAAACA GTTCTGGCTG GACAGGCCAC GGGACTTACT   5220

ACTGCAGGAC GAGGCAGCGC GGCTATCGTG GCTGGCCACG ACGGGCGTTC CTTGCGCAGC   5280
TGACGTCCTG CTCCGTCGCG CCGATAGCAC CGACCGGTGC TGCCCGCAAG GAACGCGTCG   5280

TGTGCTCGAC GTTGTCACTG AAGCGGGAAG GGACTGGCTG CTATTGGGCG AAGTGCCGGG   5340
ACACGAGCTG CAACAGTGAC TTCGCCCTTC CCTGACCGAC GATAACCCGC TTCACGGCCC   5340

GCAGGATCTC CTGTCATCTC ACCTTGCTCC TGCCGAGAAA GTATCCATCA TGGCTGATGC   5400
CGTCCTAGAG GACAGTAGAG TGGAACGAGG ACGGCTCTTT CATAGGTAGT ACCGACTACG   5400

AATGCGGCGG CTGCATACGC TTGATCCGGC TACCTGCCCA TTCGACCACC AAGCGAAACA   5460
TTACGCCGCC GACGTATGCG AACTAGGCCG ATGGACGGGT AAGCTGGTGG TTCGCTTTGT   5460
```

FIG. 11H pICAST ALN

```
TCGCATCGAG CGAGCACGTA CTCGGATGGA AGCCGGTCTT GTCGATCAGG ATGATCTGGA    5520
AGCGTAGCTC GCTCGTGCAT GAGCCTACCT TCGGCCAGAA CAGCTAGTCC TACTAGACCT    5520

CGAAGAGCAT CAGGGGCTCG CGCCAGCCGA ACTGTTCGCC AGGCTCAAGG CGCGCATGCC    5580
GCTTCTCGTA GTCCCCGAGC GCGGTCGGCT TGACAAGCGG TCCGAGTTCC GCGCGTACGG    5580

CGACGGCGAG GATCTCGTCG TGACCCATGG CGATGCCTGC TTGCCGAATA TCATGGTGGA    5640
GCTGCCGCTC CTAGAGCAGC ACTGGGTACC GCTACGGACG AACGGCTTAT AGTACCACCT    5640

AAATGGCCGC TTTTCTGGAT TCATCGACTG TGGCCGGCTG GGTGTGGCGG ACCGCTATCA    5700
TTTACCGGCG AAAAGACCTA AGTAGCTGAC ACCGGCCGAC CCACACCGCC TGGCGATAGT    5700

GGACATAGCG TTGGCTACCC GTGATATTGC TGAAGAGCTT GGCGGCGAAT GGGCTGACCG    5760
CCTGTATCGC AACCGATGGG CACTATAACG ACTTCTCGAA CCGCCGCTTA CCCGACTGGC    5760

CTTCCTCGTG CTTTACGGTA TCGCCGCTCC CGATTCGCAG CGCATCGCCT TCTATCGCCT    5820
GAAGGAGCAC GAAATGCCAT AGCGGCGAGG GCTAAGCGTC GCGTAGCGGA AGATAGCGGA    5820

TCTTGACGAG TTCTTCTGAG CGGGACTCTG GGGTTCGCAT CGATAAAATA AAAGATTTTA    5880
AGAACTGCTC AAGAAGACTC GCCCTGAGAC CCCAAGCGTA GCTATTTTAT TTTCTAAAAT    5880

TTTAGTCTCC AGAAAAAGGG GGGAATGAAA GACCCCACCT GTAGGTTTGG CAAGCTAGCT    5940
AAATCAGAGG TCTTTTTCCC CCCTTACTTT CTGGGGTGGA CATCCAAACC GTTCGATCGA    5940

TAAGTAACGC CATTTTGCAA GGCATGGAAA AATACATAAC TGAGAATAGA GAAGTTCAGA    6000
ATTCATTGCG GTAAAACGTT CCGTACCTTT TTATGTATTG ACTCTTATCT CTTCAAGTCT    6000

TCAAGGTCAG GAACAGATGG AACAGCTGAA TATGGGCCAA ACAGGATATC TGTGGTAAGC    6060
AGTTCCAGTC CTTGTCTACC TTGTCGACTT ATACCCGGTT TGTCCTATAG ACACCATTCG    6060

AGTTCCTGCC CCGGCTCAGG GCCAAGAACA GATGGAACAG CTGAATATGG GCCAAACAGG    6120
TCAAGGACGG GGCCGAGTCC CGGTTCTTGT CTACCTTGTC GACTTATACC CGGTTTGTCC    6120

ATATCTGTGG TAAGCAGTTC CTGCCCCGGC TCAGGGCCAA GAACAGATGG TCCCCAGATG    6180
TATAGACACC ATTCGTCAAG GACGGGGCCG AGTCCCGGTT CTTGTCTACC AGGGGTCTAC    6180

CGGTCCAGCC CTCAGCAGTT TCTAGAGAAC CATCAGATGT TTCCAGGGTG CCCCAAGGAC    6240
GCCAGGTCGG GAGTCGTCAA AGATCTCTTG GTAGTCTACA AAGGTCCCAC GGGGTTCCTG    6240
```

FIG.11I pICAST ALN

```
CTGAAATGAC CCTGTGCCTT ATTTGAACTA ACCAATCAGT TCGCTTCTCG CTTCTGTTCG   6300
GACTTTACTG GGACACGGAA TAAACTTGAT TGGTTAGTCA AGCGAAGAGC GAAGACAAGC   6300

CGCGCTTCTG CTCCCCGAGC TCAATAAAAG AGCCCACAAC CCCTCACTCG GGGCGCCAGT   6360
GCGCGAAGAC GAGGGGCTCG AGTTATTTTC TCGGGTGTTG GGGAGTGAGC CCCGCGGTCA   6360

CCTCCGATTG ACTGAGTCGC CCGGGTACCC GTGTATCCAA TAAACCCTCT TGCAGTTGCA   6420
GGAGGCTAAC TGACTCAGCG GGCCCATGGG CACATAGGTT ATTTGGGAGA ACGTCAACGT   6420

TCCGACTTGT GGTCTCGCTG TTCCTTGGGA GGGTCTCCTC TGAGTGATTG ACTACCCGTC   6480
AGGCTGAACA CCAGAGCGAC AAGGAACCCT CCCAGAGGAG ACTCACTAAC TGATGGGCAG   6480

AGCGGGGGTC TTTCATTCAT GCAGCATGTA TCAAAATTAA TTTGGTTTTT TTTCTTAAGT   6540
TCGCCCCCAG AAAGTAAGTA CGTCGTACAT AGTTTTAATT AAACCAAAAA AAAGAATTCA   6540

ATTTACATTA AATGGCCATA GTTGCATTAA TGAATCGGCC AACGCGCGGG GAGAGGCGGT   6600
TAAATGTAAT TTACCGGTAT CAACGTAATT ACTTAGCCGG TTGCGCGCCC CTCTCCGCCA   6600

AACGCATAAC CGCGAGAAGG CGAAGGAGCG AGTGACTGAG CGACGCGAGC CAGCAAGCCG   6660
TTGCGTATTG GCGCTCTTCC GCTTCCTCGC TCACTGACTC GCTGCGCTCG GTCGTTCGGC   6660

TGCGGCGAGC GGTATCAGCT CACTCAAAGG CGGTAATACG GTTATCCACA GAATCAGGGG   6720
ACGCCGCTCG CCATAGTCGA GTGAGTTTCC GCCATTATGC CAATAGGTGT CTTAGTCCCC   6720

ATAACGCAGG AAAGAACATG TGAGCAAAAG GCCAGCAAAA GGCCAGGAAC CGTAAAAAGG   6780
TATTGCGTCC TTTCTTGTAC ACTCGTTTTC CGGTCGTTTT CCGGTCCTTG GCATTTTTCC   6780

CCGCGTTGCT GGCGTTTTTC CATAGGCTCC GCCCCCCTGA CGAGCATCAC AAAAATCGAC   6840
GGCGCAACGA CCGCAAAAAG GTATCCGAGG CGGGGGGACT GCTCGTAGTG TTTTTAGCTG   6840

GCTCAAGTCA GAGGTGGCGA AACCCGACAG GACTATAAAG ATACCAGGCG TTTCCCCCTG   6900
CGAGTTCAGT CTCCACCGCT TTGGGCTGTC CTGATATTTC TATGGTCCGC AAAGGGGGAC   6900

GAAGCTCCCT CGTGCGCTCT CCTGTTCCGA CCCTGCCGCT TACCGGATAC CTGTCCGCCT   6960
CTTCGAGGGA GCACGCGAGA GGACAAGGCT GGGACGGCGA ATGGCCTATG GACAGGCGGA   6960

TTCTCCCTTC GGGAAGCGTG GCGCTTTCTC ATAGCTCACG CTGTAGGTAT CTCAGTTCGG   7020
AAGAGGGAAG CCCTTCGCAC CGCGAAAGAG TATCGAGTGC GACATCCATA GAGTCAAGCC   7020
```

FIG.11J pICAST ALN

```
TGTAGGTCGT TCGCTCCAAG CTGGGCTGTG TGCACGAACC CCCCGTTCAG CCCGACCGCT   7080
ACATCCAGCA AGCGAGGTTC GACCCGACAC ACGTGCTTGG GGGGCAAGTC GGGCTGGCGA   7080

GCGCCTTATC CGGTAACTAT CGTCTTGAGT CCAACCCGGT AAGACACGAC TTATCGCCAC   7140
CGCGGAATAG GCCATTGATA GCAGAACTCA GGTTGGGCCA TTCTGTGCTG AATAGCGGTG   7140

TGGCAGCAGC CACTGGTAAC AGGATTAGCA GAGCGAGGTA TGTAGGCGGT GCTACAGAGT   7200
ACCGTCGTCG GTGACCATTG TCCTAATCGT CTCGCTCCAT ACATCCGCCA CGATGTCTCA   7200

TCTTGAAGTG GTGGCCTAAC TACGGCTACA CTAGAAGAAC AGTATTTGGT ATCTGCGCTC   7260
AGAACTTCAC CACCGGATTG ATGCCGATGT GATCTTCTTG TCATAAACCA TAGACGCGAG   7260

TGCTGAAGCC AGTTACCTTC GGAAAAAGAG TTGGTAGCTC TTGATCCGGC AAACAAACCA   7320
ACGACTTCGG TCAATGGAAG CCTTTTTCTC AACCATCGAG AACTAGGCCG TTTGTTTGGT   7320

CCGCTGGTAG CGGTGGTTTT TTTGTTTGCA AGCAGCAGAT TACGCGCAGA AAAAAAGGAT   7380
GGCGACCATC GCCACCAAAA AAACAAACGT TCGTCGTCTA ATGCGCGTCT TTTTTTCCTA   7380

CTCAAGAAGA TCCTTTGATC TTTTCTACGG GGTCTGACGC TCAGTGGAAC GAAAACTCAC   7440
GAGTTCTTCT AGGAAACTAG AAAAGATGCC CCAGACTGCG AGTCACCTTG CTTTTGAGTG   7440

GTTAAGGGAT TTTGGTCATG AGATTATCAA AAAGGATCTT CACCTAGATC CTTTTGCGGC   7500
CAATTCCCTA AAACCAGTAC TCTAATAGTT TTTCCTAGAA GTGGATCTAG GAAAACGCCG   7500

CGCAAATCAA TCTAAAGTAT ATATGAGTAA ACTTGGTCTG ACAGTTACCA ATGCTTAATC   7560
GCGTTTAGTT AGATTTCATA TATACTCATT TGAACCAGAC TGTCAATGGT TACGAATTAG   7560

AGTGAGGCAC CTATCTCAGC GATCTGTCTA TTTCGTTCAT CCATAGTTGC CTGACTCCCC   7620
TCACTCCGTG GATAGAGTCG CTAGACAGAT AAAGCAAGTA GGTATCAACG GACTGAGGGG   7620

GTCGTGTAGA TAACTACGAT ACGGGAGGGC TTACCATCTG GCCCCAGTGC TGCAATGATA   7680
CAGCACATCT ATTGATGCTA TGCCCTCCCG AATGGTAGAC CGGGGTCACG ACGTTACTAT   7680

CCGCGAGACC CACGCTCACC GGCTCCAGAT TTATCAGCAA TAAACCAGCC AGCCGGAAGG   7740
GGCGCTCTGG GTGCGAGTGG CCGAGGTCTA AATAGTCGTT ATTTGGTCGG TCGGCCTTCC   7740

GCCGAGCGCA GAAGTGGTCC TGCAACTTTA TCCGCCTCCA TCCAGTCTAT TAATTGTTGC   7800
CGGCTCGCGT CTTCACCAGG ACGTTGAAAT AGGCGGAGGT AGGTCAGATA ATTAACAACG   7800
```

FIG. 11K pICAST ALN

```
CGGGAAGCTA GAGTAAGTAG TTCGCCAGTT AATAGTTTGC GCAACGTTGT TGCCATTGCT   7860
GCCCTTCGAT CTCATTCATC AAGCGGTCAA TTATCAAACG CGTTGCAACA ACGGTAACGA   7860

ACAGGCATCG TGGTGTCACG CTCGTCGTTT GGTATGGCTT CATTCAGCTC CGGTTCCCAA   7920
TGTCCGTAGC ACCACAGTGC GAGCAGCAAA CCATACCGAA GTAAGTCGAG GCCAAGGGTT   7920

CGATCAAGGC GAGTTACATG ATCCCCCATG TTGTGCAAAA AAGCGGTTAG CTCCTTCGGT   7980
GCTAGTTCCG CTCAATGTAC TAGGGGGTAC AACACGTTTT TTCGCCAATC GAGGAAGCCA   7980

CCTCCGATCG TTGTCAGAAG TAAGTTGGCC GCAGTGTTAT CACTCATGGT TATGGCAGCA   8040
GGAGGCTAGC AACAGTCTTC ATTCAACCGG CGTCACAATA GTGAGTACCA ATACCGTCGT   8040

CTGCATAATT CTCTTACTGT CATGCCATCC GTAAGATGCT TTTCTGTGAC TGGTGAGTAC   8100
GACGTATTAA GAGAATGACA GTACGGTAGG CATTCTACGA AAAGACACTG ACCACTCATG   8100

TCAACCAAGT CATTCTGAGA ATAGTGTATG CGGCGACCGA GTTGCTCTTG CCCGGCGTCA   8160
AGTTGGTTCA GTAAGACTCT TATCACATAC GCCGCTGGCT CAACGAGAAC GGGCCGCAGT   8160

ATACGGGATA ATACCGCGCC ACATAGCAGA ACTTTAAAAG TGCTCATCAT TGGAAAACGT   8220
TATGCCCTAT TATGGCGCGG TGTATCGTCT TGAAATTTTC ACGAGTAGTA ACCTTTTGCA   8220

TCTTCGGGGC GAAAACTCTC AAGGATCTTA CCGCTGTTGA GATCCAGTTC GATGTAACCC   8280
AGAAGCCCCG CTTTTGAGAG TTCCTAGAAT GGCGACAACT CTAGGTCAAG CTACATTGGG   8280

ACTCGTGCAC CCAACTGATC TTCAGCATCT TTTACTTTCA CCAGCGTTTC TGGGTGAGCA   8340
TGAGCACGTG GGTTGACTAG AAGTCGTAGA AAATGAAAGT GGTCGCAAAG ACCCACTCGT   8340

AAAACAGGAA GGCAAAATGC CGCAAAAAAG GGAATAAGGG CGACACGGAA ATGTTGAATA   8400
TTTTGTCCTT CCGTTTTACG GCGTTTTTTC CCTTATTCCC GCTGTGCCTT TACAACTTAT   8400

CTCATACTCT TCCTTTTTCA ATATTATTGA AGCATTTATC AGGGTTATTG TCTCATGAGC   8460
GAGTATGAGA AGGAAAAAGT TATAATAACT TCGTAAATAG TCCCAATAAC AGAGTACTCG   8460

GGATACATAT TTGAATGTAT TTAGAAAAAT AAACAAATAG GGGTTCCGCG CACATTTC    8518
CCTATGTATA AACTTACATA AATCTTTTTA TTTGTTTATC CCCAAGGCGC GTGTAAAG    8518
```

FIG.11L pICAST OMC

```
CTGCAGCCTG AATATGGGCC AAACAGGATA TCTGTGGTAA GCAGTTCCTG CCCCGGCTCA   60
GACGTCGGAC TTATACCCGG TTTGTCCTAT AGACACCATT CGTCAAGGAC GGGGCCGAGT   60

GGGCCAAGAA CAGATGGAAC AGCTGAATAT GGGCCAAACA GGATATCTGT GGTAAGCAGT  120
CCCGGTTCTT GTCTACCTTG TCGACTTATA CCCGGTTTGT CCTATAGACA CCATTCGTCA  120

TCCTGCCCCG GCTCAGGGCC AAGAACAGAT GGTCCCCAGA TGCGGTCCAG CCCTCAGCAG  180
AGGACGGGGC CGAGTCCCGG TTCTTGTCTA CCAGGGGTCT ACGCCAGGTC GGGAGTCGTC  180

TTTCTAGAGA ACCATCAGAT GTTTCCAGGG TGCCCCAAGG ACCTGAAATG ACCCTGTGCC  240
AAAGATCTCT TGGTAGTCTA CAAAGGTCCC ACGGGGTTCC TGGACTTTAC TGGGACACGG  240

TTATTTGAAC TAACCAATCA GTTCGCTTCT CGCTTCTGTT CGCGCGCTTC TGCTCCCCGA  300
AATAAACTTG ATTGGTTAGT CAAGCGAAGA GCGAAGACAA GCGCGCGAAG ACGAGGGGCT  300

GCTCAATAAA AGAGCCCACA ACCCCTCACT CGGGGCGCCA GTCCTCCGAT TGACTGAGTC  360
CGAGTTATTT TCTCGGGTGT TGGGGAGTGA GCCCCGCGGT CAGGAGGCTA ACTGACTCAG  360

GCCCGGGTAC CCGTGTATCC AATAAACCCT CTTGCAGTTG CATCCGACTT GTGGTCTCGC  420
CGGGCCCATG GGCACATAGG TTATTTGGGA GAACGTCAAC GTAGGCTGAA CACCAGAGCG  420

TGTTCCTTGG GAGGYTCTCC TCTGAGTGAT TGACTACCCG TCAGCGGGGG TCTTTCATTT  480
ACAAGGAACC CTCCCAGAGG AGACTCACTA ACTGATGGGC AGTCGCCCCC AGAAAGTAAA  480

GGGGGCTCGT CCGGGATCGG GAGACCCCTG CCCAGGGACC ACCGACCCAC CACCGGGAGG  540
CCCCCGAGCA GGCCCTAGCC CTCTGGGGAC GGGTCCCTGG TGGCTGGGTG GTGGCCCTCC  540

CAAGCTGGCC AGCAACTTAT CTGTGTCTGT CCGATTGTCT AGTGTCTATG ACTGATTTTA  600
GTTCGACCGG TCGTTGAATA GACACAGACA GGCTAACAGA TCACAGATAC TGACTAAAAT  600

TGCGCCTGCG TCGGTACTAG TTAGCTAACT AGCTCTGTAT CTGGCGGACC CGTGGTGGAA  660
ACGCGGACGC AGCCATGATC AATCGATTGA TCGAGACATA GACCGCCTGG GCACCACCTT  660

CTGACGAGTT CTGAACACCC GGCCGCAACC CTGGGAGACG TCCCAGGGAC TTTGGGGGCC  720
GACTGCTCAA GACTTGTGGG CCGGCGTTGG GACCCTCTGC AGGGTCCCTG AAACCCCCGG  720

GTTTTTGTGG CCCGACCTGA GGAAGGGAGT CGATGTGGAA TCCGACCCCG TCAGGATATG  780
CAAAAACACC GGGCTGGACT CCTTCCCTCA GCTACACCTT AGGCTGGGGC AGTCCTATAC  780
```

FIG.12B pICAST OMC

```
TGGTTCTGGT AGGAGACGAG AACCTAAAAC AGTTCCCGCC TCCGTCTGAA TTTTTGCTTT  840
ACCAAGACCA TCCTCTGCTC TTGGATTTTG TCAAGGGCGG AGGCAGACTT AAAAACGAAA  840

CGGTTTGGAA CCGAAGCCGC GCGTCTTGTC TGCTGCAGCA TCGTTCTGTG TTGTCTCTGT  900
GCCAAACCTT GGCTTCGGCG CGCAGAACAG ACGACGTCGT AGCAAGACAC AACAGAGACA  900

CTGACTGTGT TTCTGTATTT GTCTGAAAAT TAGGGCCAGA CTGTTACCAC TCCCTTAAGT  960
GACTGACACA AAGACATAAA CAGACTTTTA ATCCCGGTCT GACAATGGTG AGGGAATTCA  960

TTGACCTTAG GTAACTGGAA AGATGTCGAG CGGCTCGCTC ACAACCAGTC GGTAGATGTC  1020
AACTGGAATC CATTGACCTT TCTACAGCTC GCCGAGCGAG TGTTGGTCAG CCATCTACAG  1020

AAGAAGAGAC GTTGGGTTAC CTTCTGCTCT GCAGAATGGC CAACCTTTAA CGTCGGATGG  1080
TTCTTCTCTG CAACCCAATG GAAGACGAGA CGTCTTACCG GTTGGAAATT GCAGCCTACC  1080

CCGCGAGACG GCACCTTTAA CCGAGACCTC ATCACCCAGG TTAAGATCAA GGTCTTTTCA  1140
GGCGCTCTGC CGTGGAAATT GGCTCTGGAG TAGTGGGTCC AATTCTAGTT CCAGAAAAGT  1140

CCTGGCCCGC ATGGACACCC AGACCAGGTC CCCTACATCG TGACCTGGGA AGCCTTGGCT  1200
GGACCGGGCG TACCTGTGGG TCTGGTCCAG GGGATGTAGC ACTGGACCCT TCGGAACCGA  1200

TTTGACCCCC CTCCCTGGGT CAAGCCCTTT GTACACCCTA AGCCTCCGCC TCCTCTTCCT  1260
AAACTGGGGG GAGGGACCCA GTTCGGGAAA CATGTGGGAT TCGGAGGCGG AGGAGAAGGA  1260

CCATCCGCCC CGTCTCTCCC CCTTGAACCT CCTCGTTCGA CCCCGCCTCG ATCCTCCCTT  1320
GGTAGGCGGG GCAGAGAGGG GGAACTTGGA GGAGCAAGCT GGGGCGGAGC TAGGAGGGAA  1320

TATCCAGCCC TCACTCCTTC TCTAGGCGCC GGCCGCTCTA GCCCATTAAT ACGACTCACT  1380
ATAGGTCGGG AGTGAGGAAG AGATCCGCGG CCGGCGAGAT CGGGTAATTA TGCTGAGTGA  1380

ATAGGGCGAT TCGAATCAGG CCTTGGCGCG CCGGATCCTT AATTAAGCGC AATTGGGAGG  1440
TATCCCGCTA AGCTTAGTCC GGAACCGCGC GGCCTAGGAA TTAATTCGCG TTAACCCTCC  1440

TGGCGGTAGC CTCGAGATGG GCGTGATTAC GGATTCACTG GCCGTCGTTT TACAACGTCG  1500
ACCGCCATCG GAGCTCTACC CGCACTAATG CCTAAGTGAC CGGCAGCAAA ATGTTGCAGC  1500

TGACTGGGAA AACCCTGGCG TTACCCAACT TAATCGCCTT GCAGCACATC CCCCTTTCGC  1560
ACTGACCCTT TTGGGACCGC AATGGGTTGA ATTAGCGGAA CGTCGTGTAG GGGGAAAGCG  1560
```

FIG. 12C pICAST OMC

```
CAGCTGGCGT AATAGCGAAG AGGCCCGCAC CGATCGCCCT TCCCAACAGT TACGCAGCCT    1620
GTCGACCGCA TTATCGCTTC TCCGGGCGTG GCTAGCGGGA AGGGTTGTCA ATGCGTCGGA    1620

GAATGGCGAA TGGCGCTTTG CCTGGTTTCC GGCACCAGAA GCGGTGCCGG AAAGCTGGCT    1680
CTTACCGCTT ACCGCGAAAC GGACCAAAGG CCGTGGTCTT CGCCACGGCC TTTCGACCGA    1680

GGAGTGCGAT CTTCCTGAGG CCGATACTGT CGTCGTCCCC TCAAACTGGC AGATGCACGG    1740
CCTCACGCTA GAAGGACTCC GGCTATGACA GCAGCAGGGG AGTTTGACCG TCTACGTGCC    1740

TTACGATGCG CCCATCTACA CCAACGTGAC CTATCCCATT ACGGTCAATC CGCCGTTTGT    1800
AATGCTACGC GGGTAGATGT GGTTGCACTG GATAGGGTAA TGCCAGTTAG GCGGCAAACA    1800

TCCCACGGAG AATCCGACGG GTTGTTACTC GCTCACATTT AATGTTGATG AAAGCTGGCT    1860
AGGGTGCCTC TTAGGCTGCC CAACAATGAG CGAGTGTAAA TTACAACTAC TTTCGACCGA    1860

ACAGGAAGGC CAGACGCGAA TTATTTTTGA TGGCGTTAAC TCGGCGTTTC ATCTGTGGTG    1920
TGTCCTTCCG GTCTGCGCTT AATAAAAACT ACCGCAATTG AGCCGCAAAG TAGACACCAC    1920

CAACGGGCGC TGGGTCGGTT ACGGCCAGGA CAGTCGTTTG CCGTCTGAAT TTGACCTGAG    1980
GTTGCCCGCG ACCCAGCCAA TGCCGGTCCT GTCAGCAAAC GGCAGACTTA AACTGGACTC    1980

CGCATTTTTA CGCGCCGGAG AAAACCGCCT CGCGGTGATG GTGCTGCGCT GGAGTGACGG    2040
GCGTAAAAAT GCGCGGCCTC TTTTGGCGGA GCGCCACTAC CACGACGCGA CCTCACTGCC    2040

CAGTTATCTG GAAGATCAGG ATATGTGGCG GATGAGCGGC ATTTTCCGTG ACGTCTCGTT    2100
GTCAATAGAC CTTCTAGTCC TATACACCGC CTACTCGCCG TAAAAGGCAC TGCAGAGCAA    2100

GCTGCATAAA CCGACTACAC AAATCAGCGA TTTCCATGTT GCCACTCGCT TTAATGATGA    2160
CGACGTATTT GGCTGATGTG TTTAGTCGCT AAAGGTACAA CGGTGAGCGA AATTACTACT    2160

TTTCAGCCGC GCTGTACTGG AGGCTGAAGT TCAGATGTGC GGCGAGTTGC GTGACTACCT    2220
AAAGTCGGCG CGACATGACC TCCGACTTCA AGTCTACACG CCGCTCAACG CACTGATGGA    2220

ACGGGTAACA GTTTCTTTAT GGCAGGGTGA AACGCAGGTC GCCAGCGGCA CCGCGCCTTT    2280
TGCCCATTGT CAAAGAAATA CCGTCCCACT TTGCGTCCAG CGGTCGCCGT GGCGCGGAAA    2280

CGGCGGTGAA ATTATCGATG AGCGTGGTGG TTATGCCGAT CGCGTCACAC TACGTCTGAA    2340
GCCGCCACTT TAATAGCTAC TCGCACCACC AATACGGCTA GCGCAGTGTG ATGCAGACTT    2340
```

FIG.12D pICAST OMC

```
CGTCGAAAAC CCGAAACTGT GGAGCGCCGA AATCCCGAAT CTCTATCGTG CGGTGGTTGA  2400
GCAGCTTTTG GGCTTTGACA CCTCGCGGCT TTAGGGCTTA GAGATAGCAC GCCACCAACT  2400

ACTGCACACC GCCGACGGCA CGCTGATTGA AGCAGAAGCC TGCGATGTCG GTTTCCGCGA  2460
TGACGTGTGG CGGCTGCCGT GCGACTAACT TCGTCTTCGG ACGCTACAGC CAAAGGCGCT  2460

GGTGCGGATT GAAAATGGTC TGCTGCTGCT GAACGGCAAG CCGTTGCTGA TTCGAGGCGT  2520
CCACGCCTAA CTTTTACCAG ACGACGACGA CTTGCCGTTC GGCAACGACT AAGCTCCGCA  2520

TAACCGTCAC GAGCATCATC CTCTGCATGG TCAGGTCATG GATGAGCAGA CGATGGTGCA  2580
ATTGGCAGTG CTCGTAGTAG GAGACGTACC AGTCCAGTAC CTACTCGTCT GCTACCACGT  2580

GGATATCCTG CTGATGAAGC AGAACAACTT TAACGCCGTG CGCTGTTCGC ATTATCCGAA  2640
CCTATAGGAC GACTACTTCG TCTTGTTGAA ATTGCGGCAC GCGACAAGCG TAATAGGCTT  2640

CCATCCGCTG TGGTACACGC TGTGCGACCG CTACGGCCTG TATGTGGTGG ATGAAGCCAA  2700
GGTAGGCGAC ACCATGTGCG ACACGCTGGC GATGCCGGAC ATACACCACC TACTTCGGTT  2700

TATTGAAACC CACGGCATGG TGCCAATGAA TCGTCTGACC GATGATCCGC GCTGGCTACC  2760
ATAACTTTGG GTGCCGTACC ACGGTTACTT AGCAGACTGG CTACTAGGCG CGACCGATGG  2760

GGCGATGAGC GAACGCGTAA CGCGAATGGT GCAGCGCGAT CGTAATCACC CGAGTGTGAT  2820
CCGCTACTCG CTTGCGCATT GCGCTTACCA CGTCGCGCTA GCATTAGTGG GCTCACACTA  2820

CATCTGGTCG CTGGGGAATG AATCAGGCCA CGGCGCTAAT CACGACGCGC TGTATCGCTG  2880
GTAGACCAGC GACCCCTTAC TTAGTCCGGT GCCGCGATTA GTGCTGCGCG ACATAGCGAC  2880

GATCAAATCT GTCGATCCTT CCCGCCCGGT GCAGTATGAA GGCGGCGGAG CCGACACCAC  2940
CTAGTTTAGA CAGCTAGGAA GGGCGGGCCA CGTCATACTT CCGCCGCCTC GGCTGTGGTG  2940

GGCCACCGAT ATTATTTGCC CGATGTACGC GCGCGTGGAT GAAGACCAGC CCTTCCCGGC  3000
CCGGTGGCTA TAATAAACGG GCTACATGCG CGCGCACCTA CTTCTGGTCG GGAAGGGCCG  3000

TGTGCCGAAA TGGTCCATCA AAAAATGGCT TTCGCTACCT GGAGAGACGC GCCCGCTGAT  3060
ACACGGCTTT ACCAGGTAGT TTTTTACCGA AAGCGATGGA CCTCTCTGCG CGGGCGACTA  3060

CCTTTGCGAA TACGCCCACG CGATGGGTAA CAGTCTTGGC GGTTTCGCTA AATACTGGCA  3120
GGAAACGCTT ATGCGGGTGC GCTACCCATT GTCAGAACCG CCAAAGCGAT TTATGACCGT  3120
```

FIG.12E pICAST OMC

```
GGCGTTTCGT CAGTATCCCC GTTTACAGGG CGGCTTCGTC TGGGACTGGG TGGATCAGTC    3180
CCGCAAAGCA GTCATAGGGG CAAATGTCCC GCCGAAGCAG ACCCTGACCC ACCTAGTCAG    3180

GCTGATTAAA TATGATGAAA ACGGCAACCC GTGGTCGGCT TACGGCGGTG ATTTTGGCGA    3240
CGACTAATTT ATACTACTTT TGCCGTTGGG CACCAGCCGA ATGCCGCCAC TAAAACCGCT    3240

TACGCCGAAC GATCGCCAGT TCTGTATGAA CGGTCTGGTC TTTGCCGACC GCACGCCGCA    3300
ATGCGGCTTG CTAGCGGTCA AGACATACTT GCCAGACCAG AAACGGCTGG CGTGCGGCGT    3300

TCCAGCGCTG ACGAAGCAA AACACCAGCA GCAGTTTTTC CAGTTCCGTT TATCCGGGCA     3360
AGGTCGCGAC TGCCTTCGTT TTGTGGTCGT CGTCAAAAAG GTCAAGGCAA ATAGGCCCGT    3360

AACCATCGAA GTGACCAGCG AATACCTGTT CCGTCATAGC GATAACGAGC TCCTGCACTG    3420
TTGGTAGCTT CACTGGTCGC TTATGGACAA GGCAGTATCG CTATTGCTCG AGGACGTGAC    3420

GATGGTGGCG CTGGATGGTA AGCCGCTGGC AAGCGGTGAA GTGCCTCTGG ATGTCGCTCC    3480
CTACCACCGC GACCTACCAT TCGGCGACCG TTCGCCACTT CACGGAGACC TACAGCGAGG    3480

ACAAGGTAAA CAGTTGATTG AACTGCCTGA ACTACCGCAG CCGGAGAGCG CCGGGCAACT    3540
TGTTCCATTT GTCAACTAAC TTGACGGACT TGATGGCGTC GGCCTCTCGC GGCCCGTTGA    3540

CTGGCTCACA GTACGCGTAG TGCAACCGAA CGCGACCGCA TGGTCAGAAG CCGGGCACAT    3600
GACCGAGTGT CATGCGCATC ACGTTGGCTT GCGCTGGCGT ACCAGTCTTC GGCCCGTGTA    3600

CAGCGCCTGG CAGCAGTGGC GTCTGGCGGA AAACCTCAGT GTGACGCTCC CCGCCGCGTC    3660
GTCGCGGACC GTCGTCACCG CAGACCGCCT TTTGGAGTCA CACTGCGAGG GGCGGCGCAG    3660

CCACGCCATC CCGCATCTGA CCACCAGCGA AATGGATTTT TGCATCGAGC TGGGTAATAA    3720
GGTGCGGTAG GGCGTAGACT GGTGGTCGCT TTACCTAAAA ACGTAGCTCG ACCCATTATT    3720

GCGTTGGCAA TTTAACCGCC AGTCAGGCTT TCTTTCACAG ATGTGGATTG GCGATAAAAA    3780
CGCAACCGTT AAATTGGCGG TCAGTCCGAA AGAAAGTGTC TACACCTAAC CGCTATTTTT    3780

ACAACTGCTG ACGCCGCTGC GCGATCAGTT CACCCGTGTC GATAGATCTG AACAGAAACT    3840
TGTTGACGAC TGCGGCGACG CGCTAGTCAA GTGGGCACAG CTATCTAGAC TTGTCTTTGA    3840

CATTTCCGAA GAAGACCTAG TCGACCATCA TCATCATCAT CACCGGTAAT AATAGGTAGA    3900
GTAAAGGCTT CTTCTGGATC AGCTGGTAGT AGTAGTAGTA GTGGCCATTA TTATCCATCT    3900
```

FIG. 12F pICAST OMC

```
TAAGTGACTG ATTAGATGCA TTTCGACTAG ATCCCTCGAC CAATTCCGGT TATTTTCCAC   3960
ATTCACTGAC TAATCTACGT AAAGCTGATC TAGGGAGCTG GTTAAGGCCA ATAAAAGGTG   3960

CATATTGCCG TCTTTTGGCA ATGTGAGGGC CCGGAAACCT GGCCCTGTCT TCTTGACGAG   4020
GTATAACGGC AGAAAACCGT TACACTCCCG GGCCTTTGGA CCGGGACAGA AGAACTGCTC   4020

CATTCCTAGG GGTCTTTCCC CTCTCGCCAA AGGAATGCAA GGTCTGTTGA ATGTCGTGAA   4080
GTAAGGATCC CCAGAAAGGG GAGAGCGGTT TCCTTACGTT CCAGACAACT TACAGCACTT   4080

GGAAGCAGTT CCTCTGGAAG CTTCTTGAAG ACAAACAACG TCTGTAGCGA CCCTTTGCAG   4140
CCTTCGTCAA GGAGACCTTC GAAGAACTTC TGTTTGTTGC AGACATCGCT GGGAAACGTC   4140

GCAGCGGAAC CCCCCACCTG GCGACAGGTG CCTCTGCGGC CAAAAGCCAC GTGTATAAGA   4200
CGTCGCCTTG GGGGGTGGAC CGCTGTCCAC GGAGACGCCG GTTTTCGGTG CACATATTCT   4200

TACACCTGCA AAGGCGGCAC AACCCCAGTG CCACGTTGTG AGTTGGATAG TTGTGGAAAG   4260
ATGTGGACGT TTCCGCCGTG TTGGGGTCAC GGTGCAACAC TCAACCTATC AACACCTTTC   4260

AGTCAAATGG CTCTCCTCAA GCGTATTCAA CAAGGGGCTG AAGGATGCCC AGAAGGTACC   4320
TCAGTTTACC GAGAGGAGTT CGCATAAGTT GTTCCCCGAC TTCCTACGGG TCTTCCATGG   4320

CCATTGTATG GGATCTGATC TGGGGCCTCG GTGCACATGC TTTACATGTG TTTAGTCGAG   4380
GGTAACATAC CCTAGACTAG ACCCCGGAGC CACGTGTACG AAATGTACAC AAATCAGCTC   4380

GTTAAAAAAC GTCTAGGCCC CCCGAACCAC GGGGACGTGG TTTTCCTTTG AAAAACACGA   4440
CAATTTTTTG CAGATCCGGG GGGCTTGGTG CCCCTGCACC AAAAGGAAAC TTTTTGTGCT   4440

TGATAATACC ATGAAAAAGC CTGAACTCAC CGCGACGTCT GTCGAGAAGT TTCTGATCGA   4500
ACTATTATGG TACTTTTTCG GACTTGAGTG GCGCTGCAGA CAGCTCTTCA AAGACTAGCT   4500

AAAGTTCGAC AGCGTCTCCG ACCTGATGCA GCTCTCGGAG GGCGAAGAAT CTCGTGCTTT   4560
TTTCAAGCTG TCGCAGAGGC TGGACTACGT CGAGAGCCTC CCGCTTCTTA GAGCACGAAA   4560

CAGCTTCGAT GTAGGAGGGC GTGGATATGT CCTGCGGGTA AATAGCTGCG CCGATGGTTT   4620
GTCGAAGCTA CATCCTCCCG CACCTATACA GGACGCCCAT TTATCGACGC GGCTACCAAA   4620

CTACAAAGAT CGTTATGTTT ATCGGCACTT TGCATCGGCC GCGCTCCCGA TTCCGGAAGT   4680
GATGTTTCTA GCAATACAAA TAGCCGTGAA ACGTAGCCGG CGCGAGGGCT AAGGCCTTCA   4680
```

FIG. 12G pICAST OMC

```
GCTTGACATT GGGGAATTTA GCGAGAGCCT GACCTATTGC ATCTCCCGCC GTGCACAGGG    4740
CGAACTGTAA CCCCTTAAAT CGCRCTCGGA CTGGATAACG TAGAGGGCGG CACGTGTCCC    4740

TGTCACGTTG CAAGACCTGC CTGAAACCGA ACTGCCCGCT GTTCTGCAGC CGGTCGCGGA    4800
ACAGTGCAAC GTTCTGGACG GACTTTGGCT TGACGGGCGA CAAGACGTCG GCCAGCGCCT    4800

GGCCATGGAT GCGATCGCTG CGGCCGATCT TAGCCAGACG AGCGGGTTCG GCCCATTCGG    4860
CCGGTACCTA CGCTAGCGAC GCCGGCTAGA ATCGGTCTGC TCGCCCAAGC CGGGTAAGCC    4860

ACCGCAAGGA ATCGGTCAAT ACACTACATG GCGTGATTTC ATATGCGCGA TTGCTGATCC    4920
TGGCGTTCCT TAGCCAGTTA TGTGATGTAC CGCACTAAAG TATACGCGCT AACGACTAGG    4920

CCATGTGTAT CACTGGCAAA CTGTGATGGA CGACACCGTC AGTGCGTCCG TCGCGCAGGC    4980
GGTACACATA GTGACCGTTT GACACTACCT GCTGTGGCAG TCACGCAGGC AGCGCGTCCG    4980

TCTCGATGAG CTGATGCTTT GGGCCGAGGA CTGCCCCGAA GTCCGGCACC TCGTGCACGC    5040
AGAGCTACTC GACTACGAAA CCCGGCTCCT GACGGGGCTT CAGGCCGTGG AGCACGTGCG    5040

GGATTTCGGC TCCAACAATG TCCTGACGGA CAATGGCCGC ATAACAGCGG TCATTGACTG    5100
CCTAAAGCCG AGGTTGTTAC AGGACTGCCT GTTACCGGCG TATTGTCGCC AGTAACTGAC    5100

GAGCGAGGCG ATGTTCGGGG ATTCCCAATA CGAGGTCGCC AACATCTTCT TCTGGAGGCC    5160
CTCGCTCCGC TACAAGCCCC TAAGGGTTAT GCTCCAGCGG TTGTAGAAGA AGACCTCCGG    5160

GTGGTTGGCT TGTATGGAGC AGCAGACGCG CTACTTCGAG CGGAGGCATC CGGAGCTTGC    5220
CACCAACCGA ACATACCTCG TCGTCTGCGC GATGAAGCTC GCCTCCGTAG GCCTCGAACG    5220

AGGATCGCCG CGGCTCCGGG CGTATATGCT CCGCATTGGT CTTGACCAAC TCTATCAGAG    5280
TCCTAGCGGC GCCGAGGCCC GCATATACGA GGCGTAACCA GAACTGCTTG AGATAGTCTC    5280

CTTGGTTGAC GGCAATTTCG ATGATGCAGC TTGGGCGCAG GGTCGATGCG ACGCAATCGT    5340
GAACCAACTG CCGTTAAAGC TACTACGTCG AACCCGCGTC CCAGCTACGC TGCGTTAGCA    5340

CCGATCCGGA GCCGGGACTG TCGGGCGTAC ACAAATCGCC CGCAGAAGCG CGGCCGTCTG    5400
GGCTAGGCCT CGGCCCTGAC AGCCCGCATG TGTTTAGCGG GCGTCTTCGC GCCGGCAGAC    5400

GACCGATGGC TGTGTAGAAG TACTCGCCGA TAGTGGAAAC CGACGCCCCA GCACTCGTCC    5460
CTGGCTACCG ACACATCTTC ATGAGCGGCT ATCACCTTTG GCTGCGGGGT CGTGAGCAGG    5460
```

FIG. 12H pICAST OMC

```
GAGGGCAAAG GAATAGAGTA GATGCCGACC GGGATCTATC GATAAAATAA AAGATTTTAT    5520
CTCCCGTTTC CTTATCTCAT CTACGGCTGG CCCTAGATAG CTATTTTATT TTCTAAAATA    5520

TTAGTCTCCA GAAAAAGGGG GGAATGAAAG ACCCCACCTG TAGGTTTGGC AAGCTAGCTT    5580
AATCAGAGGT CTTTTTCCCC CCTTACTTTC TGGGGTGGAC ATCCAAACCG TTCGATCGAA    5580

AAGTAACGCC ATTTTGCAAG GCATGGAAAA ATACATAACT GAGAATAGAG AAGTTCAGAT    5640
TTCATTGCGG TAAAACGTTC CGTACCTTTT TATGTATTGA CTCTTATCTC TTCAAGTCTA    5640

CAAGGTCAGG AACAGATGGA ACAGCTGAAT ATGGGCCAAA CAGGATATCT GTGGTAAGCA    5700
GTTCCAGTCC TTGTCTACCT TGTCGACTTA TACCCGGTTT GTCCTATAGA CACCATTCGT    5700

GTTCCTGCCC CGGCTCAGGG CCAAGAACAG ATGGAACAGC TGAATATGGG CCAAACAGGA    5760
CAAGGACGGG GCCGAGTCCC GGTTCTTGTC TACCTTGTCG ACTTATACCC GGTTTGTCCT    5760

TATCTGTGGT AAGCAGTTCC TGCCCCGGCT CAGGGCCAAG AACAGATGGT CCCCAGATGC    5820
ATAGACACCA TTCGTCAAGG ACGGGGCCGA GTCCCGGTTC TTGTCTACCA GGGGTCTACG    5820

GGTCCAGCCC TCAGCAGTTT CTAGAGAACC ATCAGATGTT TCCAGGGTGC CCCAAGGACC    5880
CCAGGTCGGG AGTCGTCAAA GATCTCTTGG TAGTCTACAA AGGTCCCACG GGGTTCCTGG    5880

TGAAATGACC CTGTGCCTTA TTTGAACTAA CCAATCAGTT CGCTTCTCGC TTCTGTTCGC    5940
ACTTTACTGG GACACGGAAT AAACTTGATT GGTTAGTCAA GCGAAGAGCG AAGACAAGCG    5940

GCGCTTCTGC TCCCCGAGCT CAATAAAAGA GCCCACAACC CCTCACTCGG GGCGCCAGTC    6000
CGCGAAGACG AGGGGCTCGA GTTATTTTCT CGGGTGTTGG GGAGTGAGCC CCGCGGTCAG    6000

CTCCGATTGA CTGAGTCGCC CGGGTACCCG TGTATCCAAT AAACCCTCTT GCAGTTGCAT    6060
GAGGCTAACT GACTCAGCGG GCCCATGGGC ACATAGGTTA TTTGGGAGAA CGTCAACGTA    6060

CCGACTTGTG GTCTCGCTGT TCCTTGGGAG GGTCTCCTCT GAGTGATTGA CTACCCGTCA    6120
GGCTGAACAC CAGAGCGACA AGGAACCCTC CCAGAGGAGA CTCACTAACT GATGGGCAGT    6120

GCGGGGGTCT TTCATTCATG CAGCATGTAT CAAAATTAAT TTGGTTTTTT TTCTTAAGTA    6180
CGCCCCCAGA AAGTAAGTAC GTCGTACATA GTTTTAATTA AACCAAAAAA AAGAATTCAT    6180

TTTACATTAA ATGGCCATAG TTGCATTAAT GAATCGGCCA ACGCGCGGGG AGAGGCGGTT    6240
AAATGTAATT TACCGGTATC AACGTAATTA CTTAGCCGGT TGCGCGCCCC TCTCCGCCAA    6240
```

FIG. 121 pICAST OMC

```
TGCGTATTGG CGCTCTTCCG CTTCCTCGCT CACTGACTCG CTGCGCTCGG TCGTTCGGCT    6300
ACGCATAACC GCGAGAAGGC GAAGGAGCGA GTGACTGAGC GACGCGAGCC AGCAAGCCGA    6300

GCGGCGAGCG GTATCAGCTC ACTCAAAGGC GGTAATACGG TTATCCACAG AATCAGGGGA    6360
CGCCGCTCGC CATAGTCGAG TGAGTTTCCG CCATTATGCC AATAGGTGTC TTAGTCCCCT    6360

TAACGCAGGA AAGAACATGT GAGCAAAAGG CCAGCAAAAG GCCAGGAACC GTAAAAAGGC    6420
ATTGCGTCCT TTCTTGTACA CTCGTTTTCC GGTCGTTTTC CGGTCCTTGG CATTTTTCCG    6420

CGCGTTGCTG GCGTTTTTCC ATAGGCTCCG CCCCCCTGAC GAGCATCACA AAAATCGACG    6480
GCGCAACGAC CGCAAAAAGG TATCCGAGGC GGGGGGACTG CTCGTAGTGT TTTTAGCTGC    6480

CTCAAGTCAG AGGTGGCGAA ACCCGACAGG ACTATAAAGA TACCAGGCGT TTCCCCCTGG    6540
GAGTTCAGTC TCCACCGCTT TGGGCTGTCC TGATATTTCT ATGGTCCGCA AAGGGGGACC    6540

AAGCTCCCTC GTGCGCTCTC CTGTTCCGAC CCTGCCGCTT ACCGGATACC TGTCCGCCTT    6600
TTCGAGGGAG CACGCGAGAG GACAAGGCTG GGACGGCGAA TGGCCTATGG ACAGGCGGAA    6600

TCTCCCTTCG GGAAGCGTGG CGCTTTCTCA TAGCTCACGC TGTAGGTATC TCAGTTCGGT    6660
AGAGGGAAGC CCTTCGCACC GCGAAAGAGT ATCGAGTGCG ACATCCATAG AGTCAAGCCA    6660

GTAGGTCGTT CGCTCCAAGC TGGGCTGTGT GCACGAACCC CCCGTTCAGC CCGACCGCTG    6720
CATCCAGCAA GCGAGGTTCG ACCCGACACA CGTGCTTGGG GGGCAAGTCG GGCTGGCGAC    6720

CGCCTTATCC GGTAACTATC GTCTTGAGTC CAACCCGGTA AGACACGACT TATCGCCACT    6780
GCGGAATAGG CCATTGATAG CAGAACTCAG GTTGGGCCAT TCTGTGCTGA ATAGCGGTGA    6780

GGCAGCAGCC ACTGGTAACA GGATTAGCAG AGCGAGGTAT GTAGGCGGTG CTACAGAGTT    6840
CCGTCGTCGG TGACCATTGT CCTAATCGTC TCGCTCCATA CATCCGCCAC GATGTCTCAA    6840

CTTGAAGTGG TGGCCTAACT ACGGCTACAC TAGAAGAACA GTATTTGGTA TCTGCGCTCT    6900
GAACTTCACC ACCGGATTGA TGCCGATGTG ATCTTCTTGT CATAAACCAT AGACGCGAGA    6900

GCTGAAGCCA GTTACCTTCG GAAAAAGAGT TGGTAGCTCT TGATCCGGCA AACAAACCAC    6960
CGACTTCGGT CAATGGAAGC CTTTTTCTCA ACCATCGAGA ACTAGGCCGT TTGTTTGGTG    6960

CGCTGGTAGC GGTGGTTTTT TTGTTTGCAA GCAGCAGATT ACGCGCAGAA AAAAGGATC    7020
GCGACCATCG CCACCAAAAA AACAAACGTT CGTCGTCTAA TGCGCGTCTT TTTTTCCTAG    7020
```

FIG.12J pICAST OMC

```
TCAAGAAGAT CCTTTGATCT TTTCTACGGG GTCTGACGCT CAGTGGAACG AAAACTCACG   7080
AGTTCTTCTA GGAAACTAGA AAAGATGCCC CAGACTGCGA GTCACCTTGC TTTTGAGTGC   7080

TTAAGGGATT TTGGTCATGA GATTATCAAA AAGGATCTTC ACCTAGATCC TTTTAAATTA   7140
AATTCCCTAA AACCAGTACT CTAATAGTTT TTCCTAGAAG TGGATCTAGG AAAATTTAAT   7140

AAAATGAAGT TTGCGGCCGC AAATCAATCT AAAGTATATA TGAGTAAACT TGGTCTGACA   7200
TTTTACTTCA AACGCCGGCG TTTAGTTAGA TTTCATATAT ACTCATTTGA ACCAGACTGT   7200

GTTACCAATG CTTAATCAGT GAGGCACCTA TCTCAGCGAT CTGTCTATTT CGTTCATCCA   7260
CAATGGTTAC GAATTAGTCA CTCCGTGGAT AGAGTCGCTA GACAGATAAA GCAAGTAGGT   7260

TAGTTGCCTG ACTCCCCGTC GTGTAGATAA CTACGATACG GGAGGGCTTA CCATCTGGCC   7320
ATCAACGGAC TGAGGGGCAG CACATCTATT GATGCTATGC CCTCCCGAAT GGTAGACCGG   7320

CCAGTGCTGC AATGATACCG CGAGACCCAC GCTCACCGGC TCCAGATTTA TCAGCAATAA   7380
GGTCACGACG TTACTATGGC GCTCTGGGTG CGAGTGGCCG AGGTCTAAAT AGTCGTTATT   7380

ACCAGCCAGC CGGAAGGGCC GAGCGCAGAA GTGGTCCTGC AACTTTATCC GCCTCCATCC   7440
TGGTCGGTCG GCCTTCCCGG CTCGCGTCTT CACCAGGACG TTGAAATAGG CGGAGGTAGG   7440

AGTCTATTAA TTGTTGCCGG GAAGCTAGAG TAAGTAGTTC GCCAGTTAAT AGTTTGCGCA   7500
TCAGATAATT AACAACGGCC CTTCGATCTC ATTCATCAAG CGGTCAATTA TCAAACGCGT   7500

ACGTTGTTGC CATTGCTACA GGCATCGTGG TGTCACGCTC GTCGTTTGGT ATGGCTTCAT   7560
TGCAACAACG GTAACGATGT CCGTAGCACC ACAGTGCGAG CAGCAAACCA TACCGAAGTA   7560

TCAGCTCCGG TTCCCAACGA TCAAGGCGAG TTACATGATC CCCCATGTTG TGCAAAAAAG   7620
AGTCGAGGCC AAGGGTTGCT AGTTCCGCTC AATGTACTAG GGGGTACAAC ACGTTTTTTC   7620

CGGTTAGCTC CTTCGGTCCT CCGATCGTTG TCAGAAGTAA GTTGGCCGCA GTGTTATCAC   7680
GCCAATCGAG GAAGCCAGGA GGCTAGCAAC AGTCTTCATT CAACCGGCGT CACAATAGTG   7680

TCATGGTTAT GGCAGCACTG CATAATTCTC TTACTGTCAT GCCATCCGTA AGATGCTTTT   7740
AGTACCAATA CCGTCGTGAC GTATTAAGAG AATGACAGTA CGGTAGGCAT TCTACGAAAA   7740

CTGTGACTGG TGAGTACTCA ACCAAGTCAT TCTGAGAATA GTGTATGCGG CGACCGAGTT   7800
GACACTGACC ACTCATGAGT TGGTTCAGTA AGACTCTTAT CACATACGCC GCTGGCTCAA   7800
```

FIG.12K pICAST OMC

```
GCTCTTGCCC GGCGTCAATA CGGGATAATA CCGCGCCACA TAGCAGAACT TTAAAAGTGC   7860
CGAGAACGGG CCGCAGTTAT GCCCTATTAT GGCGCGGTGT ATCGTCTTGA AATTTTCACG   7860

TCATCATTGG AAAACGTTCT TCGGGGCGAA AACTCTCAAG GATCTTACCG CTGTTGAGAT   7920
AGTAGTAACC TTTTGCAAGA AGCCCCGCTT TTGAGAGTTC CTAGAATGGC GACAACTCTA   7920

CCAGTTCGAT GTAACCCACT CGTGCACCCA ACTGATCTTC AGCATCTTTT ACTTTCACCA   7980
GGTCAAGCTA CATTGGGTGA GCACGTGGGT TGACTAGAAG TCGTAGAAAA TGAAAGTGGT   7980

GCGTTTCTGG GTGAGCAAAA ACAGGAAGGC AAAATGCCGC AAAAAAGGGA ATAAGGGCGA   8040
CGCAAAGACC CACTCGTTTT TGTCCTTCCG TTTTACGGCG TTTTTTCCCT TATTCCCGCT   8040

CACGGAAATG TTGAATACTC ATACTCTTCC TTTTTCAATA TTATTGAAGC ATTTATCAGG   8100
GTGCCTTTAC AACTTATGAG TATGAGAAGG AAAAAGTTAT AATAACTTCG TAAATAGTCC   8100

GTTATTGTCT CATGAGCGGA TACATATTTG AATGTATTTA GAAAAATAAA CAAATAGGGG   8160
CAATAACAGA GTACTCGCCT ATGTATAAAC TTACATAAAT CTTTTTATTT GTTTATCCCC   8160

TTCCGCGCAC ATTTC                                                  8175
AAGGCGCGTG TAAAG                                                  8175
```

FIG. 12L pICAST OMN

```
CTGCAGCCTG AATATGGGCC AAACAGGATA TCTGTGGTAA GCAGTTCCTG CCCCGGCTCA    60
GACGTCGGAC TTATACCCGG TTTGTCCTAT AGACACCATT CGTCAAGGAC GGGGCCGAGT    60

GGGCCAAGAA CAGATGGAAC AGCTGAATAT GGGCCAAACA GGATATCTGT GGTAAGCAGT   120
CCCGGTTCTT GTCTACCTTG TCGACTTATA CCCGGTTTGT CCTATAGACA CCATTCGTCA   120

TCCTGCCCCG GCTCAGGGCC AAGAACAGAT GGTCCCCAGA TGCGGTCCAG CCCTCAGCAG   180
AGGACGGGGC CGAGTCCCGG TTCTTGTCTA CCAGGGGTCT ACGCCAGGTC GGGAGTCGTC   180

TTTCTAGAGA ACCATCAGAT GTTTCCAGGG TGCCCCAAGG ACCTGAAATG ACCCTGTGCC   240
AAAGATCTCT TGGTAGTCTA CAAAGGTCCC ACGGGGTTCC TGGACTTTAC TGGGACACGG   240

TTATTTGAAC TAACCAATCA GTTCGCTTCT CGCTTCTGTT CGCGCGCTTC TGCTCCCCGA   300
AATAAACTTG ATTGGTTAGT CAAGCGAAGA GCGAAGACAA GCGCGCGAAG ACGAGGGGCT   300

GCTCAATAAA AGAGCCCACA ACCCCTCACT CGGGGCGCCA GTCCTCCGAT TGACTGAGTC   360
CGAGTTATTT TCTCGGGTGT TGGGGAGTGA GCCCCGCGGT CAGGAGGCTA ACTGACTCAG   360

GCCCGGGTAC CCGTGTATCC AATAAACCCT CTTGCAGTTG CATCCGACTT GTGGTCTCGC   420
CGGGCCCATG GGCACATAGG TTATTTGGGA GAACGTCAAC GTAGGCTGAA CACCAGAGCG   420

TGTTCCTTGG GAGGGTCTCC TCTGAGTGAT TGACTACCCG TCAGCGGGGG TCTTTCATTT   480
ACAAGGAACC CTCCCAGAGG AGACTCACTA ACTGATGGGC AGTCGCCCCC AGAAAGTAAA   480

GGGGGCTCGT CCGGGATCGG GAGACCCCTG CCCAGGGACC ACCGACCCAC CACCGGGAGG   540
CCCCCGAGCA GGCCCTAGCC CTCTGGGGAC GGGTCCCTGG TGGCTGGGTG GTGGCCCTCC   540

CAAGCTGGCC AGCAACTTAT CTGTGTCTGT CCGATTGTCT AGTGTCTATG ACTGATTTTA   600
GTTCGACCGG TCGTTGAATA GACACAGACA GGCTAACAGA TCACAGATAC TGACTAAAAT   600

TGCGCCTGCG TCGGTACTAG TTAGCTAACT AGCTCTGTAT CTGGCGGACC CGTGGTGGAA   660
ACGCGGACGC AGCCATGATC AATCGATTGA TCGAGACATA GACCGCCTGG GCACCACCTT   660

CTGACGAGTT CTGAACACCC GGCCGCAACC CTGGGAGACG TCCCAGGGAC TTTGGGGGCC   720
GACTGCTCAA GACTTGTGGG CCGGCGTTGG GACCCTCTGC AGGGTCCCTG AAACCCCCGG   720

GTTTTTGTGG CCCGACCTGA GGAAGGGAGT CGATGTGGAA TCCGACCCCG TCAGGATATG   780
CAAAAACACC GGGCTGGACT CCTTCCCTCA GCTACACCTT AGGCTGGGGC AGTCCTATAC   780
```

FIG. 13B pICAST OMN

```
TGGTTCTGGT AGGAGACGAG AACCTAAAAC AGTTCCCGCC TCCGTCTGAA TTTTTGCTTT   840
ACCAAGACCA TCCTCTGCTC TTGGATTTTG TCAAGGGCGG AGGCAGACTT AAAAACGAAA   840

CGGTTTGGAA CCGAAGCCGC GCGTCTTGTC TGCTGCAGCA TCGTTCTGTG TTGTCTCTGT   900
GCCAAACCTT GGCTTCGGCG CGCAGAACAG ACGACGTCGT AGCAAGACAC AACAGAGACA   900

CTGACTGTGT TTCTGTATTT GTCTGAAAAT TAGGGCCAGA CTGTTACCAC TCCCTTAAGT   960
GACTGACACA AAGACATAAA CAGACTTTTA ATCCCGGTCT GACAATGGTG AGGGAATTCA   960

TTGACCTTAG GTAACTGGAA AGATGTCGAG CGGCTCGCTC ACAACCAGTC GGTAGATGTC  1020
AACTGGAATC CATTGACCTT TCTACAGCTC GCCGAGCGAG TGTTGGTCAG CCATCTACAG  1020

AAGAAGAGAC GTTGGGTTAC CTTCTGCTCT GCAGAATGGC CAACCTTTAA CGTCGGATGG  1080
TTCTTCTCTG CAACCCAATG GAAGACGAGA CGTCTTACCG GTTGGAAATT GCAGCCTACC  1080

CCGCGAGACG GCACCTTTAA CCGAGACCTC ATCACCCAGG TTAAGATCAA GGTCTTTTCA  1140
GGCGCTCTGC CGTGGAAATT GGCTCTGGAG TAGTGGGTCC AATTCTAGTT CCAGAAAAGT  1140

CCTGGCCCGC ATGGACACCC AGACCAGGTC CCCTACATCG TGACCTGGGA AGCCTTGGCT  1200
GGACCGGGCG TACCTGTGGG TCTGGTCCAG GGGATGTAGC ACTGGACCCT TCGGAACCGA  1200

TTTGACCCCC CTCCCTGGGT CAAGCCCTTT GTACACCCTA AGCCTCCGCC TCCTCTTCCT  1260
AAACTGGGGG GAGGGACCCA GTTCGGGAAA CATGTGGGAT TCGGAGGCGG AGGAGAAGGA  1260

CCATCCGCCC CGTCTCTCCC CCTTGAACCT CCTCGTTCGA CCCCGCCTCG ATCCTCCCTT  1320
GGTAGGCGGG GCAGAGAGGG GGAACTTGGA GGAGCAAGCT GGGGCGGAGC TAGGAGGGAA  1320

TATCCAGCCC TCACTCCTTC TCTAGGCGCC GGCCGCTCTA GCCCATTAAT ACGACTCACT  1380
ATAGGTCGGG AGTGAGGAAG AGATCCGCGG CCGGCGAGAT CGGGTAATTA TGCTGAGTGA  1380

ATAGGGCGAT TCGAACACCA TGCACCATCA TCATCATCAC GTCGACGAAC AGAAACTCAT  1440
TATCCCGCTA AGCTTGTGGT ACGTGGTAGT AGTAGTAGTG CAGCTGCTTG TCTTTGAGTA  1440

TTCCGAAGAA GACCTACTCG AGATGGGCGT GATTACGGAT TCACTGGCCG TCGTTTTACA  1500
AAGGCTTCTT CTGGATGAGC TCTACCCGCA CTAATGCCTA AGTGACCGGC AGCAAAATGT  1500

ACGTCGTGAC TGGGAAAACC CTGGCGTTAC CCAACTTAAT CGCCTTGCAG CACATCCCCC  1560
TGCAGCACTG ACCCTTTTGG GACCGCAATG GGTTGAATTA GCGGAACGTC GTGTAGGGGG  1560
```

FIG.13C pICAST OMN

```
TTTCGCCAGC TGGCGTAATA GCGAAGAGGC CCGCACCGAT CGCCCTTCCC AACAGTTACG  1620
AAAGCGGTCG ACCGCATTAT CGCTTCTCCG GGCGTGGCTA GCGGGAAGGG TTGTCAATGC  1620

CAGCCTGAAT GGCGAATGGC GCTTTGCCTG GTTTCCGGCA CCAGAAGCGG TGCCGGAAAG  1680
GTCGGACTTA CCGCTTACCG CGAAACGGAC CAAAGGCCGT GGTCTTCGCC ACGGCCTTTC  1680

CTGGCTGGAG TGCGATCTTC CTGAGGCCGA TACTGTCGTC GTCCCCTCAA ACTGGCAGAT  1740
GACCGACCTC ACGCTAGAAG GACTCCGGCT ATGACAGCAG CAGGGGAGTT TGACCGTCTA  1740

GCACGGTTAC GATGCGCCCA TCTACACCAA CGTGACCTAT CCCATTACGG TCAATCCGCC  1800
CGTGCCAATG CTACGCGGGT AGATGTGGTT GCACTGGATA GGGTAATGCC AGTTAGGCGG  1800

GTTTGTTCCC ACGGAGAATC CGACGGGTTG TTACTCGCTC ACATTTAATG TTGATGAAAG  1860
CAAACAAGGG TGCCTCTTAG GCTGCCCAAC AATGAGCGAG TGTAAATTAC AACTACTTTC  1860

CTGGCTACAG GAAGGCCAGA CGCGAATTAT TTTTGATGGC GTTAACTCGG CGTTTCATCT  1920
GACCGATGTC CTTCCGGTCT GCGCTTAATA AAAACTACCG CAATTGAGCC GCAAAGTAGA  1920

GTGGTGCAAC GGGCGCTGGG TCGGTTACGG CCAGGACAGT CGTTTGCCGT CTGAATTTGA  1980
CACCACGTTG CCCGCGACCC AGCCAATGCC GGTCCTGTCA GCAAACGGCA GACTTAAACT  1980

CCTGAGCGCA TTTTTACGCG CCGGAGAAAA CCGCCTCGCG GTGATGGTGC TGCGCTGGAG  2040
GGACTCGCGT AAAAATGCGC GGCCTCTTTT GGCGGAGCGC CACTACCACG ACGCGACCTC  2040

TGACGGCAGT TATCTGGAAG ATCAGGATAT GTGGCGGATG AGCGGCATTT TCCGTGACGT  2100
ACTGCCGTCA ATAGACCTTC TAGTCCTATA CACCGCCTAC TCGCCGTAAA AGGCACTGCA  2100

CTCGTTGCTG CATAAACCGA CTACACAAAT CAGCGATTTC CATGTTGCCA CTCGCTTTAA  2160
GAGCAACGAC GTATTTGGCT GATGTGTTTA GTCGCTAAAG GTACAACGGT GAGCGAAATT  2160

TGATGATTTC AGCCGCGCTG TACTGGAGGC TGAAGTTCAG ATGTGCGGCG AGTTGCGTGA  2220
ACTACTAAAG TCGGCGCGAC ATGACCTCCG ACTTCAAGTC TACACGCCGC TCAACGCACT  2220

CTACCTACGG GTAACAGTTT CTTTATGGCA GGGTGAAACG CAGGTCGCCA GCGGCACCGC  2280
GATGGATGCC CATTGTCAAA GAAATACCGT CCCACTTTGC GTCCAGCGGT CGCCGTGGCG  2280

GCCTTTCGGC GGTGAAATTA TCGATGAGCG TGGTGGTTAT GCCGATCGCG TCACACTACG  2340
CGGAAAGCCG CCACTTTAAT AGCTACTCGC ACCACCAATA CGGCTAGCGC AGTGTGATGC  2340
```

FIG.13D pICAST OMN

```
TCTGAACGTC GAAAACCCGA AACTGTGGAG CGCCGAAATC CCGAATCTCT ATCGTGCGGT  2400
AGACTTGCAG CTTTTGGGCT TTGACACCTC GCGGCTTTAG GGCTTAGAGA TAGCACGCCA  2400

GGTTGAACTG CACACCGCCG ACGGCACGCT GATTGAAGCA GAAGCCTGCG ATGTCGGTTT  2460
CCAACTTGAC GTGTGGCGGC TGCCGTGCGA CTAACTTCGT CTTCGGACGC TACAGCCAAA  2460

CCGCGAGGTG CGGATTGAAA ATGGTCTGCT GCTGCTGAAC GGCAAGCCGT TGCTGATTCG  2520
GGCGCTCCAC GCCTAACTTT TACCAGACGA CGACGACTTG CCGTTCGGCA ACGACTAAGC  2520

AGGCGTTAAC CGTCACGAGC ATCATCCTCT GCATGGTCAG GTCATGGATG AGCAGACGAT  2580
TCCGCAATTG GCAGTGCTCG TAGTAGGAGA CGTACCAGTC CAGTACCTAC TCGTCTGCTA  2580

GGTGCAGGAT ATCCTGCTGA TGAAGCAGAA CAACTTTAAC GCCGTGCGCT GTTCGCATTA  2640
CCACGTCCTA TAGGACGACT ACTTCGTCTT GTTGAAATTG CGGCACGCGA CAAGCGTAAT  2640

TCCGAACCAT CCGCTGTGGT ACACGCTGTG CGACCGCTAC GGCCTGTATG TGGTGGATGA  2700
AGGCTTGGTA GGCGACACCA TGTGCGACAC GCTGGCGATG CCGGACATAC ACCACCTACT  2700

AGCCAATATT GAAACCCACG GCATGGTGCC AATGAATCGT CTGACCGATG ATCCGCGCTG  2760
TCGGTTATAA CTTTGGGTGC CGTACCACGG TTACTTAGCA GACTGGCTAC TAGGCGCGAC  2760

GCTACCGGCG ATGAGCGAAC GCGTAACGCG AATGGTGCAG CGCGATCGTA ATCACCCGAG  2820
CGATGGCCGC TACTCGCTTG CGCATTGCGC TTACCACGTC GCGCTAGCAT TAGTGGGCTC  2820

TGTGATCATC TGGTCGCTGG GGAATGAATC AGGCCACGGC GCTAATCACG ACGCGCTGTA  2880
ACACTAGTAG ACCAGCGACC CCTTACTTAG TCCGGTGCCG CGATTAGTGC TGCGCGACAT  2880

TCGCTGGATC AAATCTGTCG ATCCTTCCCG CCCGGTGCAG TATGAAGGCG GCGGAGCCGA  2940
AGCGACCTAG TTTAGACAGC TAGGAAGGGC GGGCCACGTC ATACTTCCGC CGCCTCGGCT  2940

CACCACGGCC ACCGATATTA TTTGCCCGAT GTACGCGCGC GTGGATGAAG ACCAGCCCTT  3000
GTGGTGCCGG TGGCTATAAT AAACGGGCTA CATGCGCGCG CACCTACTTC TGGTCGGGAA  3000

CCCGGCTGTG CCGAAATGGT CCATCAAAAA ATGGCTTTCG CTACCTGGAG AGACGCGCCC  3060
GGGCCGACAC GGCTTTACCA GGTAGTTTTT TACCGAAAGC GATGGACCTC TCTGCGCGGG  3060

GCTGATCCTT TGCGAATACG CCCACGCGAT GGGTAACAGT CTTGGCGGTT TCGCTAAATA  3120
CGACTAGGAA ACGCTTATGC GGGTGCGCTA CCCATTGTCA GAACCGCCAA AGCGATTTAT  3120
```

FIG. 13E pICAST OMN

```
CTGGCAGGCG TTTCGTCAGT ATCCCCGTTT ACAGGGCGGC TTCGTCTGGG ACTGGGTGGA    3180
GACCGTCCGC AAAGCAGTCA TAGGGGCAAA TGTCCCGCCG AAGCAGACCC TGACCCACCT    3180

TCAGTCGCTG ATTAAATATG ATGAAAACGG CAACCCGTGG TCGGCTTACG GCGGTGATTT    3240
AGTCAGCGAC TAATTTATAC TACTTTTGCC GTTGGGCACC AGCCGAATGC CGCCACTAAA    3240

TGGCGATACG CCGAACGATC GCCAGTTCTG TATGAACGGT CTGGTCTTTG CCGACCGCAC    3300
ACCGCTATGC GGCTTGCTAG CGGTCAAGAC ATACTTGCCA GACCAGAAAC GGCTGGCGTG    3300

GCCGCATCCA GCGCTGACGG AAGCAAAACA CCAGCAGCAG TTTTTCCAGT TCCGTTTATC    3360
CGGCGTAGGT CGCGACTGCC TTCGTTTTGT GGTCGTCGTC AAAAAGGTCA AGGCAAATAG    3360

CGGGCAAACC ATCGAAGTGA CCAGCGAATA CCTGTTCCGT CATAGCGATA ACGAGCTCCT    3420
GCCCGTTTGG TAGCTTCACT GGTCGCTTAT GGACAAGGCA GTATCGCTAT TGCTCGAGGA    3420

GCACTGGATG GTGGCGCTGG ATGGTAAGCC GCTGGCAAGC GGTGAAGTGC CTCTGGATGT    3480
CGTGACCTAC CACCGCGACC TACCATTCGG CGACCGTTCG CCACTTCACG GAGACCTACA    3480

CGCTCCACAA GGTAAACAGT TGATTGAACT GCCTGAACTA CCGCAGCCGG AGAGCGCCGG    3540
GCGAGGTGTT CCATTTGTCA ACTAACTTGA CGGACTTGAT GGCGTCGGCC TCTCGCGGCC    3540

GCAACTCTGG CTCACAGTAC GCGTAGTGCA ACCGAACGCG ACCGCATGGT CAGAAGCCGG    3600
CGTTGAGACC GAGTGTCATG CGCATCACGT TGGCTTGCGC TGGCGTACCA GTCTTCGGCC    3600

GCACATCAGC GCCTGGCAGC AGTGGCGTCT GGCGGAAAAC CTCAGTGTGA CGCTCCCCGC    3660
CGTGTAGTCG CGGACCGTCG TCACCGCAGA CCGCCTTTTG GAGTCACACT GCGAGGGGCG    3660

CGCGTCCCAC GCCATCCCGC ATCTGACCAC CAGCGAAATG GATTTTTGCA TCGAGCTGGG    3720
GCGCAGGGTG CGGTAGGGCG TAGACTGGTG GTCGCTTTAC CTAAAAACGT AGCTCGACCC    3720

TAATAAGCGT TGGCAATTTA ACCGCCAGTC AGGCTTTCTT TCACAGATGT GGATTGGCGA    3780
ATTATTCGCA ACCGTTAAAT TGGCGGTCAG TCCGAAAGAA AGTGTCTACA CCTAACCGCT    3780

TAAAAAACAA CTGCTGACGC CGCTGCGCGA TCAGTTCACC CGTGTCGATA GATCTGGAGG    3840
ATTTTTTGTT GACGACTGCG GCGACGCGCT AGTCAAGTGG GCACAGCTAT CTAGACCTCC    3840

TGGTGGCAGC AGGCCTTGGC GCGCCGGATC CTTAATTAAC AATTGACCGG TAATAATAGG    3900
ACCACCGTCG TCCGGAACCG CGCGGCCTAG GAATTAATTG TTAACTGGCC ATTATTATCC    3900
```

FIG.13F pICAST OMN

```
TAGATAAGTG ACTGATTAGA TGCATTTCGA CTAGATCCCT CGACCAATTC CGGTTATTTT    3960
ATCTATTCAC TGACTAATCT ACGTAAAGCT GATCTAGGGA GCTGGTTAAG GCCAATAAAA    3960

CCACCATATT GCCGTCTTTT GGCAATGTGA GGGCCCGGAA ACCTGGCCCT GTCTTCTTGA    4020
GGTGGTATAA CGGCAGAAAA CCGTTACACT CCCGGGCCTT TGGACCGGGA CAGAAGAACT    4020

CGAGCATTCC TAGGGGTCTT TCCCCTCTCG CCAAAGGAAT GCAAGGTCTG TTGAATGTCG    4080
GCTCGTAAGG ATCCCCAGAA AGGGGAGAGC GGTTTCCTTA CGTTCCAGAC AACTTACAGC    4080

TGAAGGAAGC AGTTCCTCTG GAAGCTTCTT GAAGACAAAC AACGTCTGTA GCGACCCTTT    4140
ACTTCCTTCG TCAAGGAGAC CTTCGAAGAA CTTCTGTTTG TTGCAGACAT CGCTGGGAAA    4140

GCAGGCAGCG GAACCCCCCA CCTGGCGACA GGTGCCTCTG CGGCCAAAAG CCACGTGTAT    4200
CGTCCGTCGC CTTGGGGGGT GGACCGCTGT CCACGGAGAC GCCGGTTTTC GGTGCACATA    4200

AAGATACACC TGCAAAGGCG GCACAACCCC AGTGCCACGT TGTGAGTTGG ATAGTTGTGG    4260
TTCTATGTGG ACGTTTCCGC CGTGTTGGGG TCACGGTGCA ACACTCAACC TATCAACACC    4260

AAAGAGTCAA ATGGCTCTCC TCAAGCGTAT TCAACAAGGG GCTGAAGGAT GCCCAGAAGG    4320
TTTCTCAGTT TACCGAGAGG AGTTCGCATA AGTTGTTCCC CGACTTCCTA CGGGTCTTCC    4320

TACCCCATTG TATGGGATCT GATCTGGGGC CTCGGTGCAC ATGCTTTACA TGTGTTTAGT    4380
ATGGGGTAAC ATACCCTAGA CTAGACCCCG GAGCCACGTG TACGAAATGT ACACAAATCA    4380

CGAGGTTAAA AAACGTCTAG GCCCCCCGAA CCACGGGGAC GTGGTTTTCC TTTGAAAAAC    4440
GCTCCAATTT TTTGCAGATC CGGGGGGCTT GGTGCCCCTG CACCAAAAGG AAACTTTTTG    4440

ACGATGATAA TACCATGAAA AAGCCTGAAC TCACCGCGAC GTCTGTCGAG AAGTTTCTGA    4500
TGCTACTATT ATGGTACTTT TTCGGACTTG AGTGGCGCTG CAGACAGCTC TTCAAAGACT    4500

TCGAAAAGTT CGACAGCGTC TCCGACCTGA TGCAGCTCTC GGAGGGCGAA GAATCTCGTG    4560
AGCTTTTCAA GCTGTCGCAG AGGCTGGACT ACGTCGAGAG CCTCCCGCTT CTTAGAGCAC    4560

CTTTCAGCTT CGATGTAGGA GGGCGTGGAT ATGTCCTGCG GGTAAATAGC TGCGCCGATG    4620
GAAAGTCGAA GCTACATCCT CCCGCACCTA TACAGGACGC CCATTTATCG ACGCGGCTAC    4620

GTTTCTACAA AGATCGTTAT GTTTATCGGC ACTTTGCATC GGCCGCGCTC CCGATTCCGG    4680
CAAAGATGTT TCTAGCAATA CAAATAGCCG TGAAACGTAG CCGGCGCGAG GGCTAAGGCC    4680
```

FIG.13G pICAST OMN

```
AAGTGCTTGA CATTGGGGAA TTTAGCGAGA GCCTGACCTA TTGCATCTCC CGCCGTGCAC    4740
TTCACGAACT GTAACCCCTT AAATCGCTCT CGGACTGGAT AACGTAGAGG GCGGCACGTG    4740

AGGGTGTCAC GTTGCAAGAC CTGCCTGAAA CCGAACTGCC CGCTGTTCTG CAGCCGGTCG    4800
TCCCACAGTG CAACGTTCTG GACGGACTTT GGCTTGACGG GCGACAAGAC GTCGGCCAGC    4800

CGGAGGCCAT GGATGCGATC GCTGCGGCCG ATCTTAGCCA GACGAGCGGG TTCGGCCCAT    4860
GCCTCCGGTA CCTACGCTAG CGACGCCGGC TAGAATCGGT CTGCTCGCCC AAGCCGGGTA    4860

TCGGACCGCA AGGAATCGGT CAATACACTA CATGGCGTGA TTTCATATGC GCGATTGCTG    4920
AGCCTGGCGT TCCTTAGCCA GTTATGTGAT GTACCGCACT AAAGTATACG CGCTAACGAC    4920

ATCCCCATGT GTATCACTGG CAAACTGTGA TGGACGACAC CGTCAGTGCG TCCGTCGCGC    4980
TAGGGGTACA CATAGTGACC GTTTGACACT ACCTGCTGTG GCAGTCACGC AGGCAGCGCG    4980

AGGCTCTCGA TGAGCTGATG CTTTGGGCCG AGGACTGCCC CGAAGTCCGG CACCTCGTGC    5040
TCCGAGAGCT ACTCGACTAC GAAACCCGGC TCCTGACGGG GCTTCAGGCC GTGGAGCACG    5040

ACGCGGATTT CGGCTCCAAC AATGTCCTGA CGGACAATGG CCGCATAACA GCGGTCATTG    5100
TGCGCCTAAA GCCGAGGTTG TTACAGGACT GCCTGTTACC GGCGTATTGT CGCCAGTAAC    5100

ACTGGAGCGA GGCGATGTTC GGGGATTCCC AATACGAGGT CGCCAACATC TTCTTCTGGA    5160
TGACCTCGCT CCGCTACAAG CCCCTAAGGG TTATGCTCCA GCGGTTGTAG AAGAAGACCT    5160

GGCCGTGGTT GGCTTGTATG GAGCAGCAGA CGCGCTACTT CGAGCGGAGG CATCCGGAGC    5220
CCGGCACCAA CCGAACATAC CTCGTCGTCT GCGCGATGAA GCTCGCCTCC GTAGGCCTCG    5220

TTGCAGGATC GCCGCGGCTC CGGGCGTATA TGCTCCGCAT TGGTCTTGAC CAACTCTATC    5280
AACGTCCTAG CGGCGCCGAG GCCCGCATAT ACGAGGCGTA ACCAGAACTG GTTGAGATAG    5280

AGAGCTTGGT TGACGGCAAT TTCGATGATG CAGCTTGGGC GCAGGGTCGA TGCGACGCAA    5340
TCTCGAACCA ACTGCCGTTA AAGCTACTAC GTCGAACCCG CGTCCCAGCT ACGCTGCGTT    5340

TCGTCCGATC CGGAGCCGGG ACTGTCGGGC GTACACAAAT CGCCCGCAGA AGCGCGGCCG    5400
AGCAGGCTAG GCCTCGGCCC TGACAGCCCG CATGTGTTTA GCGGGCGTCT TCGCGCCGGC    5400

TCTGGACCGA TGGCTGTGTA GAAGTACTCG CCGATAGTGG AAACCGACGC CCCAGCACTC    5460
AGACCTGGCT ACCGACACAT CTTCATGAGC GGCTATCACC TTTGGCTGCG GGGTCGTGAG    5460
```

FIG.13H pICAST OMN

```
GTCCGAGGGC AAAGGAATAG AGTAGATGCC GACCGGGATC TATCGATAAA ATAAAAGATT   5520
CAGGCTCCCG TTTCCTTATC TCATCTACGG CTGGCCCTAG ATAGCTATTT TATTTTCTAA   5520

TTATTTAGTC TCCAGAAAAA GGGGGGAATG AAGACCCCAA CCTGTAGGTT TGGCAAGCTA   5580
AATAAATCAG AGGTCTTTTT CCCCCCTTAC TTTCTGGGGT GGACATCCAA ACCGTTCGAT   5580

GCTTAAGTAA CGCCATTTTG CAAGGCATGG AAAAATACAT AACTGAGAAT AGAGAAGTTC   5640
CGAATTCATT GCGGTAAAAC GTTCCGTACC TTTTTATGTA TTGACTCTTA TCTCTTCAAG   5640

AGATCAAGGT CAGGAACAGA TGGAACAGCT GAATATGGGC CAAACAGGAT ATCTGTGGTA   5700
TCTAGTTCCA GTCCTTGTCT ACCTTGTCGA CTTATACCCG GTTTGTCCTA TAGACACCAT   5700

AGCAGTTCCT GCCCCGGCTC AGGGCCAAGA ACAGATGGAA CAGCTGAATA TGGGCCAAAC   5760
TCGTCAAGGA CGGGGCCGAG TCCCGGTTCT TGTCTACCTT GTCGACTTAT ACCCGGTTTG   5760

AGGATATCTG TGGTAAGCAG TTCCTGCCCC GGCTCAGGGC CAAGAACAGA TGGTCCCCAG   5820
TCCTATAGAC ACCATTCGTC AAGGACGGGG CCGAGTCCCG GTTCTTGTCT ACCAGGGGTC   5820

ATGCGGTCCA GCCCTCAGCA GTTTCTAGAG AACCATCAGA TGTTTCCAGG GTGCCCCAAG   5880
TACGCCAGGT CGGGAGTCGT CAAAGATCTC TTGGTAGTCT ACAAAGGTCC CACGGGGTTC   5880

GACCTGAAAT GACCCTGTGC CTTATTTGAA CTAACCAATC AGTTCGCTTC TCGCTTCTGT   5940
CTGGACTTTA CTGGGACACG GAATAAACTT GATTGGTTAG TCAAGCGAAG AGCGAAGACA   5940

TCGCGCGCTT CTGCTCCCCG AGCTCAATAA AAGAGCCCAC AACCCCTCAC TCGGGGCGCC   6000
AGCGCGCGAA GACGAGGGGC TCGAGTTATT TTCTCGGGTG TTGGGGAGTG AGCCCCGCGG   6000

AGTCCTCCGA TTGACTGAGT CGCCCGGGTA CCCGTGTATC CAATAAACCC TCTTGCAGTT   6060
TCAGGAGGCT AACTGACTCA GCGGGCCCAT GGGCACATAG GTTATTTGGG AGAACGTCAA   6060

GCATCCGACT TGTGGTCTCG CTGTTCCTTG GGAGGGTCTC CTCTGAGTGA TTGACTACCC   6120
CGTAGGCTGA ACACCAGAGC GACAAGGAAC CCTCCCAGAG GAGACTCACT AACTGATGGG   6120

GTCAGCGGGG GTCTTTCATT CATGCAGCAT GTATCAAAAT TAATTTGGTT TTTTTTCTTA   6180
CAGTCGCCCC CAGAAAGTAA GTACGTCGTA CATAGTTTTA ATTAAACCAA AAAAAAGAAT   6180

AGTATTTACA TTAAATGGCC ATAGTTGCAT TAATGAATCG GCCAACGCGC GGGGAGAGGC   6240
TCATAAATGT AATTTACCGG TATCAACGTA ATTACTTAGC CGGTTGCGCG CCCCTCTCCG   6240
```

FIG. 131 pICAST OMN

```
GGTTTGCGTA TTGGCGCTCT TCCGCTTCCT CGCTCACTGA CTCGCTGCGC TCGGTCGTTC  6300
CCAAACGCAT AACCGCGAGA AGGCGAAGGA GCGAGTGACT GAGCGACGCG AGCCAGCAAG  6300

GGCTGCGGCG AGCGGTATCA GCTCACTCAA AGGCGGTAAT ACGGTTATCC ACAGAATCAG  6360
CCGACGCCGC TCGCCATAGT CGAGTGAGTT TCCGCCATTA TGCCAATAGG TGTCTTAGTC  6360

GGGATAACGC AGGAAAGAAC ATGTGAGCAA AAGGCCAGCA AAAGGCCAGG AACCGTAAAA  6420
CCCTATTGCG TCCTTTCTTG TACACTCGTT TTCCGGTCGT TTTCCGGTCC TTGGCATTTT  6420

AGGCCGCGTT GCTGGCGTTT TTCCATAGGC TCCGCCCCCC TGACGAGCAT CACAAAAATC  6480
TCCGGCGCAA CGACCGCAAA AAGGTATCCG AGGCGGGGGG ACTGCTCGTA GTGTTTTTAG  6480

GACGCTCAAG TCAGAGGTGG CGAAACCCGA CAGGACTATA AAGATACCAG GCGTTTCCCC  6540
CTGCGAGTTC AGTCTCCACC GCTTTGGGCT GTCCTGATAT TTCTATGGTC CGCAAAGGGG  6540

CTGGAAGCTC CCTCGTGCGC TCTCCTGTTC CGACCCTGCC GCTTACCGGA TACCTGTCCG  6600
GACCTTCGAG GGAGCACGCG AGAGGACAAG GCTGGGACGG CGAATGGCCT ATGGACAGGC  6600

CCTTTCTCCC TTCGGGAAGC GTGGCGCTTT CTCATAGCTC ACGCTGTAGG TATCTCAGTT  6660
GGAAAGAGGG AAGCCCTTCG CACCGCGAAA GAGTATCGAG TGCGACATCC ATAGAGTCAA  6660

CGGTGTAGGT CGTTCGCTCC AAGCTGGGCT GTGTGCACGA ACCCCCCGTT CAGCCCGACC  6720
GCCACATCCA GCAAGCGAGG TTCGACCCGA CACACGTGCT TGGGGGGCAA GTCGGGCTGG  6720

GCTGCGCCTT ATCCGGTAAC TATCGTCTTG AGTCCAACCC GGTAAGACAC GACTTATCGC  6780
CGACGCGGAA TAGGCCATTG ATAGCAGAAC TCAGGTTGGG CCATTCTGTG CTGAATAGCG  6780

CACTGGCAGC AGCCACTGGT AACAGGATTA GCAGAGCGAG GTATGTAGGC GGTGCTACAG  6840
GTGACCGTCG TCGGTGACCA TTGTCCTAAT CGTCTCGCTC CATACATCCG CCACGATGTC  6840

AGTTCTTGAA GTGGTGGCCT AACTACGGCT ACACTAGAAG AACAGTATTT GGTATCTGCG  6900
TCAAGAACTT CACCACCGGA TTGATGCCGA TGTGATCTTC TTGTCATAAA CCATAGACGC  6900

CTCTGCTGAA GCCAGTTACC TTCGGAAAAA GAGTTGGTAG CTCTTGATCC GGCAAACAAA  6960
GAGACGACTT CGGTCAATGG AAGCCTTTTT CTCAACCATC GAGAACTAGG CCGTTTGTTT  6960

CCACCGCTGG TAGCGGTGGT TTTTTTGTTT GCAAGCAGCA GATTACGCGC AGAAAAAAAG  7020
GGTGGCGACC ATCGCCACCA AAAAAACAAA CGTTCGTCGT CTAATGCGCG TCTTTTTTTC  7020
```

FIG. 13J pICAST OMN

```
GATCTCAAGA AGATCCTTTG ATCTTTTCTA CGGGGTCTGA CGCTCAGTGG AACGAAAACT    7080
CTAGAGTTCT TCTAGGAAAC TAGAAAAGAT GCCCCAGACT GCGAGTCACC TTGCTTTTGA    7080

CACGTTAAGG GATTTTGGTC ATGAGATTAT CAAAAAGGAT CTTCACCTAG ATCCTTTTGC    7140
GTGCAATTCC CTAAAACCAG TACTCTAATA GTTTTTCCTA GAAGTGGATC TAGGAAAACG    7140

GGCCGCAAAT CAATCTAAAG TATATATGAG TAAACTTGGT CTGACAGTTA CCAATGCTTA    7200
CCGGCGTTTA GTTAGATTTC ATATATACTC ATTTGAACCA GACTGTCAAT GGTTACGAAT    7200

ATCAGTGAGG CACCTATCTC AGCGATCTGT CTATTTCGTT CATCCATAGT TGCCTGACTC    7260
TAGTCACTCC GTGGATAGAG TCGCTAGACA GATAAAGCAA GTAGGTATCA ACGGACTGAG    7260

CCCGTCGTGT AGATAACTAC GATACGGGAG GGCTTACCAT CTGGCCCCAG TGCTGCAATG    7320
GGGCAGCACA TCTATTGATG CTATGCCCTC CCGAATGGTA GACCGGGGTC ACGACGTTAC    7320

ATACCGCGAG ACCCACGCTC ACCGGCTCCA GATTTATCAG CAATAAACCA GCCAGCCGGA    7380
TATGGCGCTC TGGGTGCGAG TGGCCGAGGT CTAAATAGTC GTTATTTGGT CGGTCGGCCT    7380

AGGGCCGAGC GCAGAAGTGG TCCTGCAACT TTATCCGCCT CCATCCAGTC TATTAATTGT    7440
TCCCGGCTCG CGTCTTCACC AGGACGTTGA AATAGGCGGA GGTAGGTCAG ATAATTAACA    7440

TGCCGGGAAG CTAGAGTAAG TAGTTCGCCA GTTAATAGTT TGCGCAACGT TGTTGCCATT    7500
ACGGCCCTTC GATCTCATTC ATCAAGCGGT CAATTATCAA ACGCGTTGCA ACAACGGTAA    7500

GCTACAGGCA TCGTGGTGTC ACGCTCGTCG TTTGGTATGG CTTCATTCAG CTCCGGTTCC    7560
CGATGTCCGT AGCACCACAG TGCGAGCAGC AAACCATACC GAAGTAAGTC GAGGCCAAGG    7560

CAACGATCAA GGCGAGTTAC ATGATCCCCC ATGTTGTGCA AAAAAGCGGT TAGCTCCTTC    7620
GTTGCTAGTT CCGCTCAATG TACTAGGGGG TACAACACGT TTTTTCGCCA ATCGAGGAAG    7620

GGTCCTCCGA TCGTTGTCAG AAGTAAGTTG GCCGCAGTGT TATCACTCAT GGTTATGGCA    7680
CCAGGAGGCT AGCAACAGTC TTCATTCAAC CGGCGTCACA ATAGTGAGTA CCAATACCGT    7680

GCACTGCATA ATTCTCTTAC TGTCATGCCA TCCGTAAGAT GCTTTTCTGT GACTGGTGAG    7740
CGTGACGTAT TAAGAGAATG ACAGTACGGT AGGCATTCTA CGAAAAGACA CTGACCACTC    7740

TACTCAACCA AGTCATTCTG AGAATAGTGT ATGCGGCGAC CGAGTTGCTC TTGCCCGGCG    7800
ATGAGTTGGT TCAGTAAGAC TCTTATCACA TACGCCGCTG GCTCAACGAG AACGGGCCGC    7800
```

FIG.13K pICAST OMN

```
TCAATACGGG ATAATACCGC GCCACATAGC AGAACTTTAA AAGTGCTCAT CATTGGAAAA    7860
AGTTATGCCC TATTATGGCG CGGTGTATCG TCTTGAAATT TTCACGAGTA GTAACCTTTT    7860

CGTTCTTCGG GGCGAAAACT CTCAAGGATC TTACCGCTGT TGAGATCCAG TTCGATGTAA    7920
GCAAGAAGCC CCGCTTTTGA GAGTTCCTAG AATGGCGACA ACTCTAGGTC AAGCTACATT    7920

CCCACTCGTG CACCCAACTG ATCTTCAGCA TCTTTTACTT TCACCAGCGT TTCTGGGTGA    7980
GGGTGAGCAC GTGGGTTGAC TAGAAGTCGT AGAAAATGAA AGTGGTCGCA AAGACCCACT    7980

GCAAAAACAG GAAGGCAAAA TGCCGCAAAA AAGGGAATAA GGGCGACACG GAAATGTTGA    8040
CGTTTTTGTC CTTCCGTTTT ACGGCGTTTT TTCCCTTATT CCCGCTGTGC CTTTACAACT    8040

ATACTCATAC TCTTCCTTTT TCAATATTAT TGAAGCATTT ATCAGGGTTA TTGTCTCATG    8100
TATGAGTATG AGAAGGAAAA AGTTATAATA ACTTCGTAAA TAGTCCCAAT AACAGAGTAC    8100

AGCGGATACA TATTTGAATG TATTTAGAAA AATAAACAAA TAGGGGTTCC GCGCACATTT    8160
TCGCCTATGT ATAAACTTAC ATAAATCTTT TTATTTGTTT ATCCCCAAGG CGCGTGTAAA    8160

RECEPTOR FUNCTION ASSAY FOR G-PROTEIN COUPLED RECEPTORS AND ORPHAN RECEPTORS BY REPORTER ENZYME MUTANT COMPLEMENTATION

This application claims the benefit from Provisional Application Ser. No. 60/180,669, filed Feb. 7, 2000. The entirety of that provisional application is incorporated herein by reference.

BACKGROUND OF THE INVENTION

1. Field of the Invention

This invention relates to methods of detecting G-protein-coupled receptor (GPCR) activity, and provides methods of assaying GPCR activity and methods for screening for GPCR ligands, G-protein-coupled receptor kinase (GRK) activity, and compounds that interact with components of the GPCR regulatory process.

The actions of many extracellular signals are mediated by the interaction of G-protein-coupled receptors (GPCRs) and guanine nucleotide-binding regulatory proteins (G-proteins). G-protein-mediated signaling systems have been identified in many divergent organisms, such as mammals and yeast. The GPCRs represent a large super family of proteins which have divergent amino acid sequences, but share common structural features, in particular, the presence of seven transmembrane helical domains. GPCRs respond to, among other extracellular signals, neurotransmitters, hormones, odorants and light. Individual GPCR types activate a particular signal transduction pathway; at least ten different signal transduction pathways are known to be activated via GPCRs. For example, the beta 2-adrenergic receptor (β2AR) is a prototype mammalian GPCR. In response to agonist binding, β2AR receptors activate a G-protein (Gs) which in turn stimulates adenylate cyclase activity and results in increased cyclic adenosine monophosphate (cAMP) production in the cell.

The signaling pathway and final cellular response that result from GPCR stimulation depends on the specific class of G-protein with which the particular receptor is coupled (Hamm, "The many faces of G-Protein Signaling." J. Biol. Chem., 273:669–672 (1998)). For instance, coupling to the Gs class of G-proteins stimulates cAMP production and activation of Protein Kinase A and C pathways, whereas coupling to the Gi class of G-proteins down regulates cAMP. Other second messenger systems as calcium, phospholipase C, and phosphatidylinositol 3 may also be utilized. As a consequence, GPCR signaling events have predominantly been measured via quantification of these second messenger products.

A common feature of GPCR physiology is desensitization and recycling of the receptor through the processes of receptor phosphorylation, endocytosis and dephosphorylation (Ferguson, et al., "G-protein-coupled receptor regulation: role of G-protein-coupled receptor kinases and arrestins." Can. J. Physiol. Pharmacol., 74:1095–1110 (1996)). Ligand-occupied GPCRs can be phosphorylated by two families of serine/threonine kinases, the G-protein-coupled receptor kinases (GRKs) and the second messenger-dependent protein kinases such as protein kinase A and protein kinase C. Phosphorylation by either class of kinases serves to down-regulate the receptor by uncoupling it from its corresponding G-protein. GRK-phosphorylation also serves to down-regulate the receptor by recruitment of a class of proteins known as the airestins that bind the cytoplasmic domain of the receptor and promote clustering of the receptor into endocytic vescicles. Once the receptor is endocytosed, it will either be degraded in lysosomes or dephosphorylated and recycled back to the plasma membrane as fully-functional receptor.

Binding of an arrestin protein to an activated receptor has been documented as a common phenomenon for a variety of GPCRs ranging from rhodopsin to β2AR to the neurotensin receptor (Barak, et al., "A β-arrestin/Green Fluorescent fusion protein biosensor for detecting G-Protein-Coupled Receptor Activation," J. Biol. Chem., 272:27497–500 (1997)). Consequently, monitoring arrestin interaction with a specific GPCR can be utilized as a generic tool for measuring GPCR activation. Similarly, a single G-protein and GRK also partner with a variety of receptors (Hamm, et al. (1998) and Pitcher et al., "G-Protein-Coupled Receptor Kinases," Annu. Rev. Biochem., 67:653–92 (1998)), such that these protein/protein interactions may also be monitored to determine receptor activity.

The present invention involves the use of a proprietary technology (ICAST™, Intercistronic Complementation Analysis Screening Technology) for monitoring protein/protein interactions in GPCR signaling. The method involves using two inactive β-galactosidase mutants, each of which is fused with one of two interacting protein pairs, such as a GPCR and an arrestin. The formation of an active β-galactosidase complex is driven by interaction of the target proteins. In this system, β-galactosidase activity acts as a read out of GPCR activity. FIG. 23 is a schematic depicting the method of the present invention. FIG. 23 shows two inactive mutants that become active when they interact. In addition, this technology could be used to monitor GPCR-mediated signaling pathways via other downstream signaling components such as G-proteins, GRKs or c-Src.

Many therapeutic drugs in use today target GPCRs, as they regulate vital physiological responses, including vasodilation, heart rate, bronchodilation, endocrine secretion and gut peristalsis. See, e.g., Lefkowitz et al., Annu. Rev. Biochem., 52:159 (1983). For instance, drugs targeting the highly studied GPCR, β2AR are used in the treatment of anaphylaxis, shock hypertension, asthma and other conditions. Some of these drugs mimic the ligand for this receptor. Other drugs act to antagonize the receptor in cases when disease arises from spontaneous activity of the receptor.

Efforts such as the Human Genome Project are identifying new GPCRs ("orphan" receptors) whose physiological roles and ligands are unknown. It is estimated that several thousand GPCRs exist in the human genome.

SUMMARY OF THE INVENTION

A first aspect of the present invention is a method that monitors GPCR function proximally at the site of receptor activation, thus providing more information for drug discovery purposes due to fewer competing mechanisms. Activation of the GPCR is measured by a read-out for interaction of the receptor with a regulatory component such as arrestin, G-protein, GRK or other kinases, the binding of which to the receptor is dependent upon agonist occupation of the receptor. Protein/protein interaction is detected by complementation of reporter proteins such as utilized by the ICAST™ technology.

A further aspect of the present invention is a method of assessing G-protein-coupled receptor (GPCR) pathway activity under test conditions by providing a test cell that expresses a GPCR, e.g., muscarinic, adrenergic, dopamine, angiotensin or endothelin, as a fusion protein to a mutant reporter protein and interacting, i.e., G-proteins, arrestin or GRK, as a fusion protein with a complementing reporter protein. When test cells are exposed to a known agonist to the target GPCR under test conditions, activation of the GPCR will be monitored by complementation of the reporter enzyme. Increased reporter enzyme activity reflects interaction of the GPCR with its interacting protein partner.

A further aspect of the present invention is a method of assessing GPCR pathway activity in the presence of a test kinase.

A further aspect of the present invention is a method of assessing GPCR pathway activity in the presence of a test G-protein.

A further aspect of the present invention is a method of assessing GPCR pathway activity upon exposure of the test cell to a test ligand.

A further aspect of the present invention is a method of assessing GPCR pathway activity upon co-expression in the test cell of a second receptor.

A further aspect of the present invention is a method for screening for a ligand or agonists to an orphan GPCR. The ligand or agonist could be contained in natural or synthetic libraries or mixtures or could be a physical stimulus. A test cell is provided that expresses the orphan GPCR as a fusion protein with one β-galactosidase mutant and, for example, an arrestin or mutant form of arrestin as a fusion protein with another β-galactosidase mutant. The interaction of the arrestin with the orphan GPCR upon receptor activation is measured by enzymatic activity of the complemented β-galactosidase. The test cell is exposed to a test compound, and an increase in β-galactosidase activity indicates the presence of a ligand or agonist.

A further aspect of the present invention is a method for screening a protein of interest, for example, an arrestin protein (or mutant form of the arrestin protein) for the ability to bind to a phosphorylated, or activated, GPCR. A cell is provided that expresses a GPCR and contains β-arrestin. The cell is exposed to a known GPCR agonist and then reporter enzyme activity is detected. Increased reporter enzyme activity indicates that the β-arrestin molecule can bind to phosphorylated, or activated, GPCR in the test cell.

A further aspect of the present invention is a method to screen for an agonist to a specific GPCR. The agonist could be contained in natural or synthetic libraries or could be a physical stimulus. A test cell is provided that expresses a GPCR as a fusion protein with one β-galactosidase mutant and, for example, an arrestin as a fusion protein with another β-galactosidase mutant. The interaction of arrestin with the GPCR upon receptor activation is measured by enzymatic activity of the complemented β-galactosidase. The test cell is exposed to a test compound, and an increase in β-galactosidase activity indicates the presence of an agonist. The test cell may express a known GPCR or a variety of known GPCRs, or may express an unknown GPCR or a variety of unknown GPCRs. The GPCR may be, for example, an odorant GPCR or a βAR GPCR.

A further aspect of the present invention is a method of screening a test compound for G-protein-coupled receptor (GPCR) antagonist activity. A test cell is provided that expresses a GPCR as a fusion protein with one β-galactosidase mutant and, for example, an arrestin as a fusion protein with another β-galactosidase mutant. The interaction of arrestin with the GPCR upon receptor activation is measured by enzymatic activity of the complemented β-galactosidase. The test cell is exposed to a test compound, and an increase in β-galactosidase activity indicates the presence of an agonist. The cell is exposed to a test compound and to a GPCR agonist, and reporter enzyme activity is detected. When exposure to the agonist occurs at the same time as or subsequent to exposure to the test compound, a decrease in β-galactosidase activity after exposure to the test compound indicates that the test compound has antagonist activity to the GPCR.

A further aspect of the present invention is a method of screening a sample solution for the presence of an agonist, antagonist or ligand to a G-protein-coupled receptor (GPCR). A test cell is provided that expresses a GPCR fusion and contains, for example, a β-arrestin protein fusion. The test cell is exposed to a sample solution, and reporter enzyme activity is assessed. Changed reporter enzyme activity after exposure to the sample solution indicates the sample solution contains an agonist, antagonist or ligand for a GPCR expressed in the cell.

A farther aspect of the present invention is a method of screening a cell for the presence of a G-protein-coupled receptor (GPCR).

A further aspect of the present invention is a method of screening a plurality of cells for those cells which contain a G-protein coupled receptor (GPCR).

A further aspect of the invention is a method for mapping GPCR-mediated signaling pathways. For instance, the system could be utilized to monitor interaction of c-src with β-arrestin-1 upon GPCR activation. Additionally, the system could be used to monitor protein/protein interactions involved in, cross-talk between GPCR signaling pathways and other pathways such as that of the receptor tyrosine kinases or Ras/Raf.

A further aspect of the invention is a method for monitoring homo- or hetero-dimerization of GPCRs upon agonist or antagonist stimulation.

A further aspect of the invention is a method of screening a cell for the presence of a G-protein-coupled receptor (GPCR) responsive to a GPCR agonist. A cell is provided that contains protein partners that interact downstream in the GPCR's pathway. The protein partners are expressed as fusion proteins to the mutant, complementing enzyme and are used to monitor activation of the GPCR. The cell is exposed to a GPCR agonist and then enzymatic activity of the reporter enzyme is detected. Increased reporter enzyme activity indicates that the cell contains a GPCR responsive to the agonist.

The invention is achieved by using ICAST™ protein/protein interaction screening to map signaling pathways. This technology is applicable to a variety of known and unknown GPCRs with diverse functions. They include, but are not limited to, the following sub-families of GPCRs:

(a) receptors that bind to amine-like ligands-Acetylcholine muscarinic receptor (M1 to M5), alpha and beta Adrenoceptors, Dopamine receptors (D1, D2, D3 and D4), Histamine receptors (H1 and H2), Octopamine receptor and Serotonin receptors (5HT1, 5HT2, 5HT4, 5HT5, 5HT6, 5HT7);

(b) receptors that bind to a peptide ligand-Angiotensin receptor, Bombesin receptor, Bradykinin receptor, C-C chemokine receptors (CCR1 to CCR8, and CCR10), C-X-C type Chemokine receptors (CXC-R5), Cholecystokinin type A receptor, CCK type receptors, Endothelin receptor, Neurotesin receptor, FMLP-related receptors, Somatostatin receptors (type 1 to type 5) and Opioid receptors (type D, K, M, X);

(c) receptors that bind to hormone proteins-Follic stimulating hormone receptor, Thyrotrophin receptor and Lutropin-chbriogonadotropic hormone receptor;

(d) receptors that bind to neurotransmitters-substance P receptor, Substance K receptor and neuropeptide Y receptor;

(e) Olfactory receptors-Olfactory type 1 to type 11, Gustatory and odorant receptors;

(f) Prostanoid receptors-Prostaglandin E2 (EP1 to EP4 subtypes), Pro stacyclin and Thromboxane;

(g) receptors that bind to metabotropic substances-Metabotropic glutamate group I to group III receptors;

(h) receptors that respond to physical stimuli, such as light, or to chemical stimuli, such as taste and smell; and (i) orphan GPCRs-the natural ligand to the receptor is undefined.

ICAST™ provides many benefits to the screening process, including the ability to monitor protein interactions in any sub-cellular compartment-membrane, cytosol and nucleus; the ability to achieve a more physiologically relevant model without requiring protein overexpression; and the ability to achieve a functional assay for receptor binding allowing high information content.

BRIEF DESCRIPTION OF THE DRAWINGS

FIG. 1. Cellular expression levels of β2 adrenergic receptor (β2AR) and β-arrestin-2 (βArr2) in C2 clones. Quantification of β-gal fusion protein was performed using antibodies against β-gal and purified β-gal protein in a titration curve by a standardized ELISA assay.

FIG. 3. Interaction of activated receptor β2AR and arrestin can be measured by β-galactosidase complementation.

FIG. 4. Agonist dose response for interaction of β2AR and arrestin can be measured by β-galactosidase complementation.

FIG. 5. Antagonist mediated inhibition of receptor activity can be measured by β-galactosidase complementation in cells co-expressing β2AR-βgalΔα and βArr-βgalΔω.

FIG. 8. Variety of mammalian cell lines can be used to generate stable cells for monitoring GPCR and arrestin interactions.

FIG. 9. Beta-gal complementation can be used to monitor β2 adrenergic receptor homo-dimerization.

FIGS. 10B–10P. Nucleotide sequence for pICAST ALC (SEQ. ID NO: 1).

FIGS. 11B–11L. Nucleotide sequence for pICAST ALN (SEQ. ID NO: 3).

FIGS. 12B–12L. Nucleotide sequence for pICAST OMC (SEQ. ID NO: 4).

FIGS. 13B–13L. Nucleotide sequence for pICAST OMN (SEQ. ID NO: 5).

DETAILED DESCRIPTION OF PREFERRED EMBODIMENTS

Figure 1A:
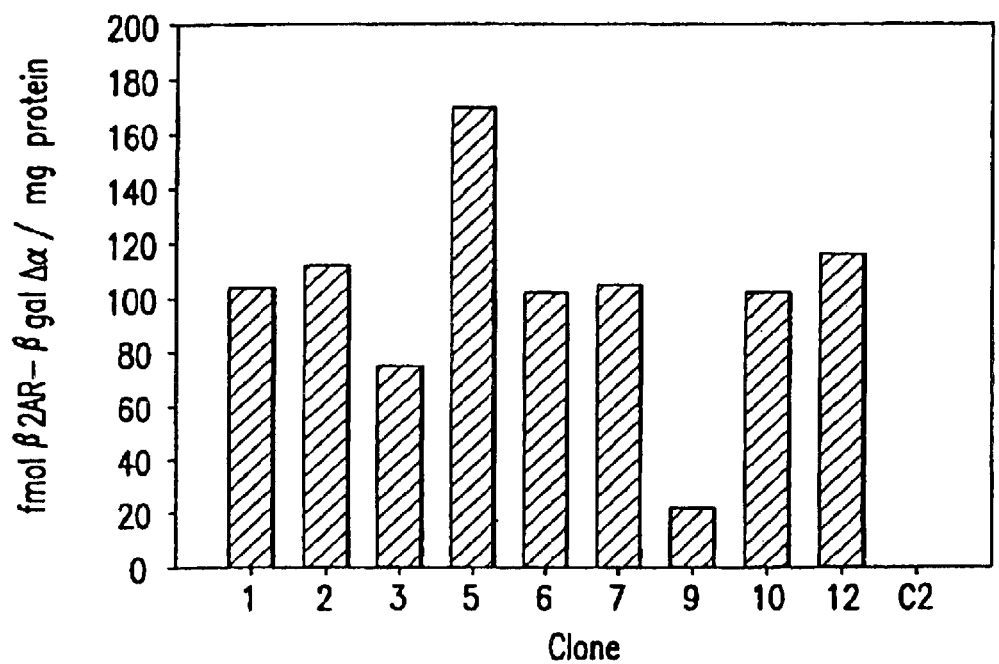
FIG. 1A shows expression levels of β2AR-βgalΔα clones (in expression vector pICAST ALC).

All literature and patents cited in this disclosure are incorporated herein by reference.

The present invention provides a method to interrogate GPCR function and pathways. The G-protein-coupled superfamily continues to expand rapidly as new receptors are discovered through automated sequencing of cDNA libraries or genomic DNA. It is estimated that several thousand GPCRs may exist in the human genome. Only a portion have been cloned and even fewer have been associated with ligands. The means by which these, or newly discovered orphan receptors, will be associated with their cognate ligands and physiological functions represents a major challenge to biological and biomedical research. The identification of an orphan receptor generally requires an individualized assay and a guess as to its function. The interrogation of a GPCR's signaling behavior by introducing a replacement receptor eliminates these prerequisites because it can be performed with and without prior knowledge of other signaling events. It is sensitive, rapid and easily performed and should be applicable to nearly all GPCRs because the majority of these receptors should desensitize by a common mechanism.

Various approaches have been used to monitor intracellular activity in response to a stimulant, e.g., enzyme-linked immunosorbent assay (ELISA); Fluorescense Imaging Plate Reader assay (FLIPR™, Molecular Devices Corp., Sunnyvale, Calif.); EVOscreen™, EVOTEC™, Evotec Biosystems Gmbh, Hamburg, Germany; and techniques developed by CELLOMICS™, Cellomics, Inc., Pittsburgh, Pa.

Germino, F. J., et al., "Screening for in vivo protein-protein interactions." Proc. Natl. Acad. Sci., 90(3): 933–7 (1993), discloses an in vivo approach for the isolation of proteins interacting with a protein of interest.

Phizicky, E. M., et al., "Protein-protein interactions: methods for detection and analysis." Microbiol. Rev., 59(1): 94–123 (1995), discloses a review of biochemical, molecular biological and genetic methods used to study protein-protein interactions.

Offermanns, et al., "Gα$_{15}$ and Gα$_{16}$ Couple a Wide Variety of Receptors to Phospholipase C." J. Biol. Chem., 270(25):15175–80 (1995), discloses that Gα$_{15}$ and Gα$_{16}$ can be activated by a wide variety of G-protein-coupled receptors. The selective coupling of an activated receptor to a distinct pattern of G-proteins is regarded as an important requirement to achieve accurate signal transduction. Id.

Barak et al., "A β-arrestin/Green Fluorescent Protein Biosensor for Detecting G Protein-coupled Receptor Activation." J. Biol. Chem., 272(44):27497–500 (1997) and U.S. Pat. No. 5,891,646, disclose the use of a β-arrestin/green fluorescent fusion protein (GFP) to monitor protein translocation upon stimulation of GPCR.

The present invention involves a method for monitoring protein-protein interactions in GPCR pathways as a complete assay using ICAST™ (Intercistronic Complementation Analysis Screening Technology as disclosed in pending U.S. patent application Ser. No. 053,614, filed Apr. 1, 1998, now U.S. Pat. No. 6,342,345 B1 the entire contents of which are incorporated herein by reference). This invention enables an array of assays, including GPCR binding assays, to be achieved directly within the cellular environment in a rapid, non-radioactive assay format amenable to high-throughput screening. Using existing technology, assays of this type are currently performed in a non-cellular environment and require the use of radioisotopes.

The present invention combined with Tropix ICAST™ and Advanced Discovery Sciences™ technologies, e.g., ultra high-throughput screening, provide highly sensitive cell-based methods for interrogating GPCR pathways which are amendable to high-throughput screening (HTS). These methods are an advancement over the invention disclosed in U.S. Pat. No. 5,891,646, which relies on microscopic imaging of GPCR components as fusion with Green-fluorescent-protein. Imaging techniques are limited by low-throughput, lack of thorough quantification and low signal to noise ratios. Unlike yeast-based-2-hybrid assays used to monitor protein/protein interactions in high-throughput assays, the present invention is applicable to a variety of cells including mammalian cells, plant cells, protozoa cells such as E. coli and cells of invertebrate origin such as yeast, slime mold (Dictyostelium) and insects; detects interactions at the site of the receptor target or downstream target proteins rather than in the nucleus; and does not rely on indirect read-outs such as transcriptional activation. The present invention provides assays with greater physiological relevance and fewer false positives.

Advanced Discovery Sciences™ is in the business of offering custom-developed screening assays optimized for individual assay requirements and validated for automation. These assays are designed by HTS experts to deliver superior assay performance. Advanced Discovery Sciences™ custom assay development service encompasses the design, development, optimization and transfer of high performance screening assays. Advanced Discovery Sciences™ works to design new assays or convert existing assays to ultra-sensitive luminescent assays ready for the rigors of HTS. Among some of the technologies developed by Advanced Discovery Sciences™ are the cAMP-Screen™ immunoassay system. This system provides ultrasensitive determination of cAMP levels in cell lysates. The cAMP-Screen™ assay utilizes the high-sensitivity chemiluminescent alkaline phosphatase (AP) substrate CSPD® with Sapphire-II™ luminescence enhancer.

Figure 1B:
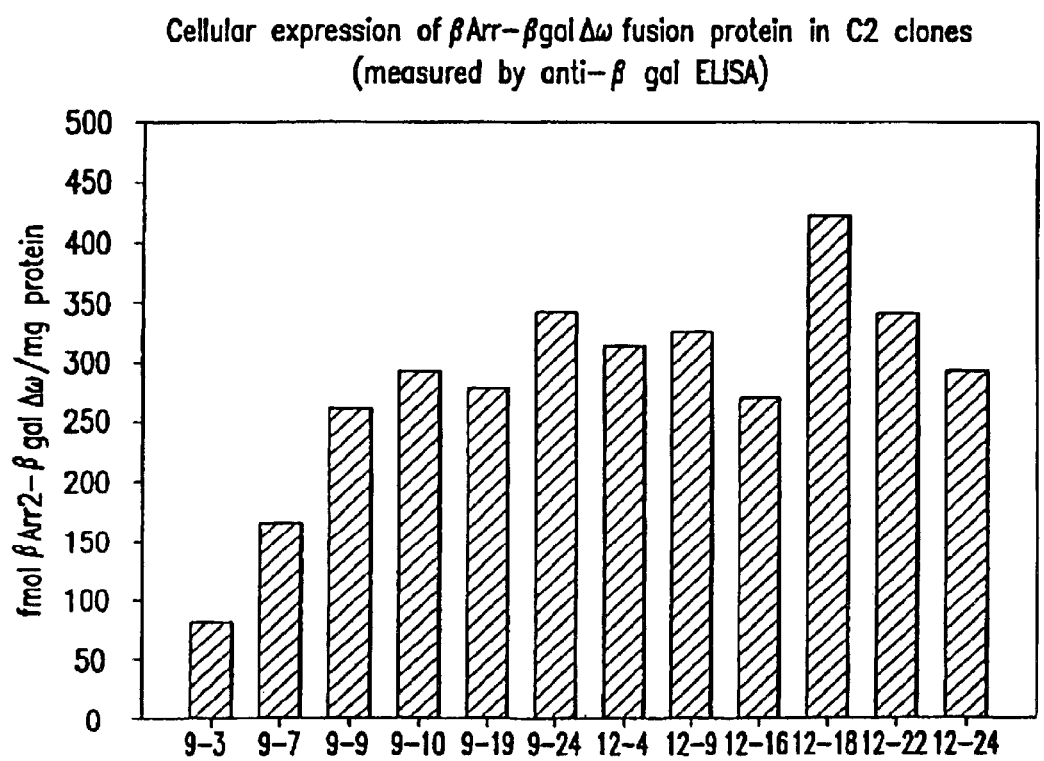
FIG. 1B shows expression levels of βArr2-βgalΔω in expression vector pICAST OMC4 for clones 9-3, -7, -9, -10, -19 and -24, or in expression vector pICAST OMN4 for clones 12-4, -9, -16, -18, -22 and -24.
Figure 2:
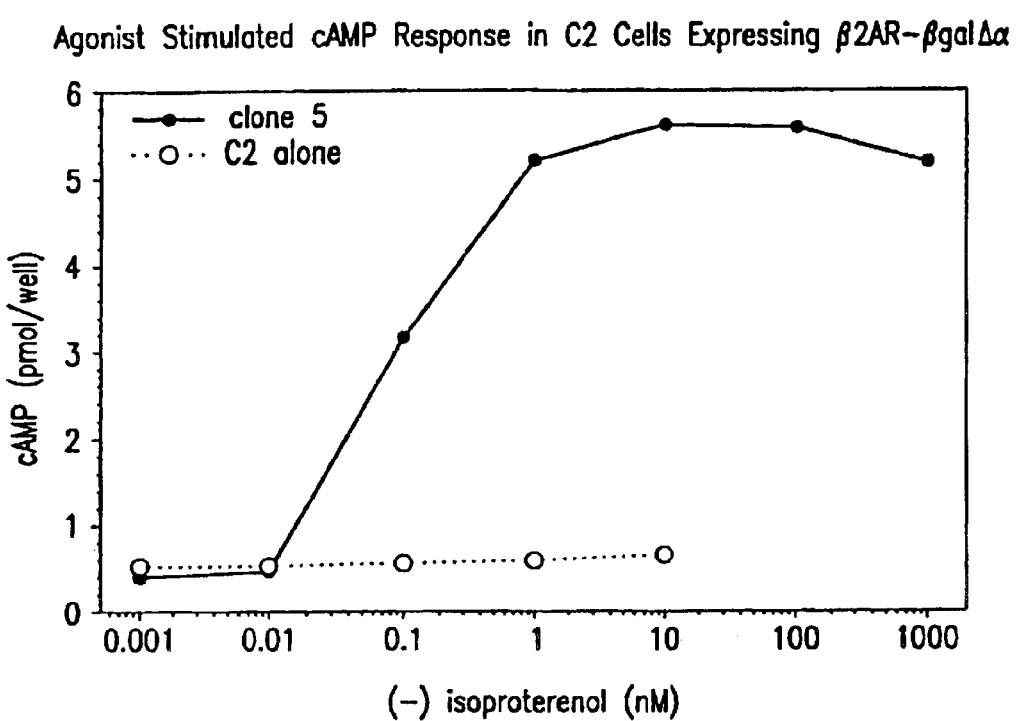
FIG. 2. Receptor β2AR activation was measured by agonist-stimulated cAMP production. C2 cells expressing pICAST ALC β2AR (clone 5) or parental cells were treated with increasing concentrations of (−)isoproterenol and 0.1 mM IBMX. The quantification of cAMP level was expressed as pmol/well.

GPCR activation can be measured through monitoring the binding of ligand-activated GPCR by an arrestin. In this assay system, a GPCR, e.g. β-adrenergic receptor (β2AR) and β-arrestin are co-expressed in the same cell as fusion proteins with β-gal mutants. As illustrated in FIG. 1, the β2AR is expressed as a fusion protein with Δα form of β-gal mutant (β2ADRΔα) and the β-arrestin as a fusion protein with the Δω mutant of β-gal (β-ArrΔω). The two fusion proteins exist inside of a resting (or un-stimulated) cell in separate compartments, i.e. membrane for GPCR and cytosol for arrestin, and they cannot form an active β-galactosidase enzyme. When such a cell is treated with an agonist or a ligand, the ligand-occupied and activated receptor will become a high affinity binding site for Arrestin. The interaction between an activated β2ADRΔα and β-ArrΔω drives the β-gal mutant complementation. The enzyme activity can be measured by using an enzyme substrate, which upon cleavage releases a product measurable by colorimetry, fluorescence, chemiluminescence (e.g. Tropix product GalScreen®).

Experiment Protocol

Figure 15:
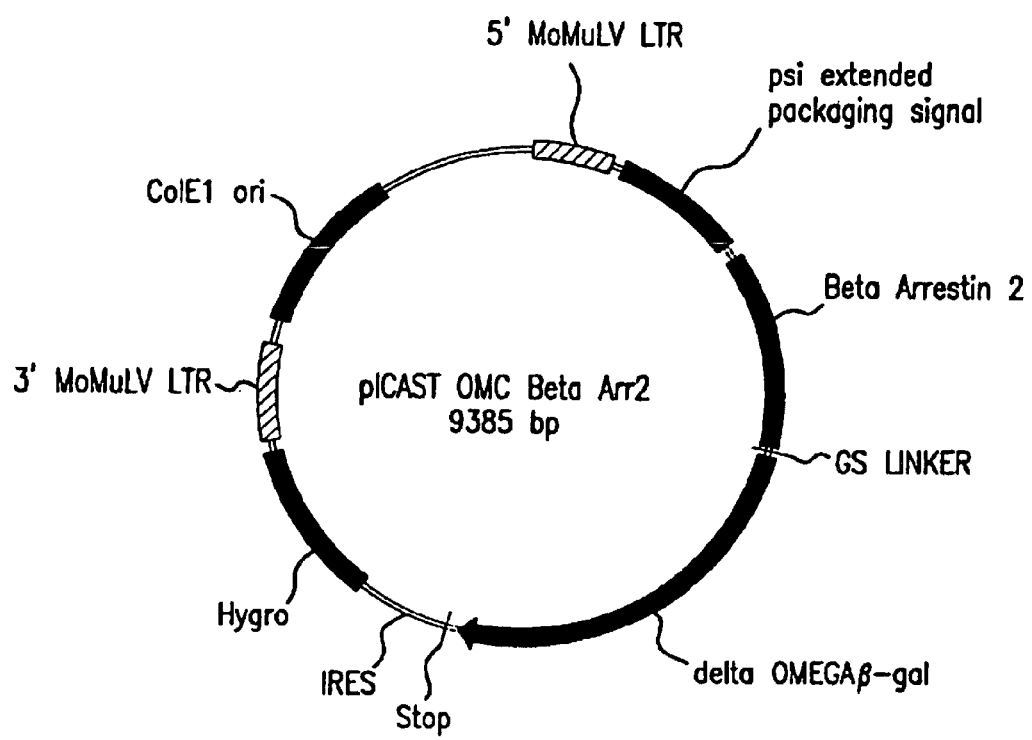
FIG. 15. pICAST OMC βArr2: Vector for expression of β-galΔω as a C-terminal fusion to β-arrestin-2. The coding sequence of human β-arrestin-2 (Genebank Accession Number: NM_0043 13) was cloned in frame to β-galΔω in a pICAST OMC vector.
Figure 16:
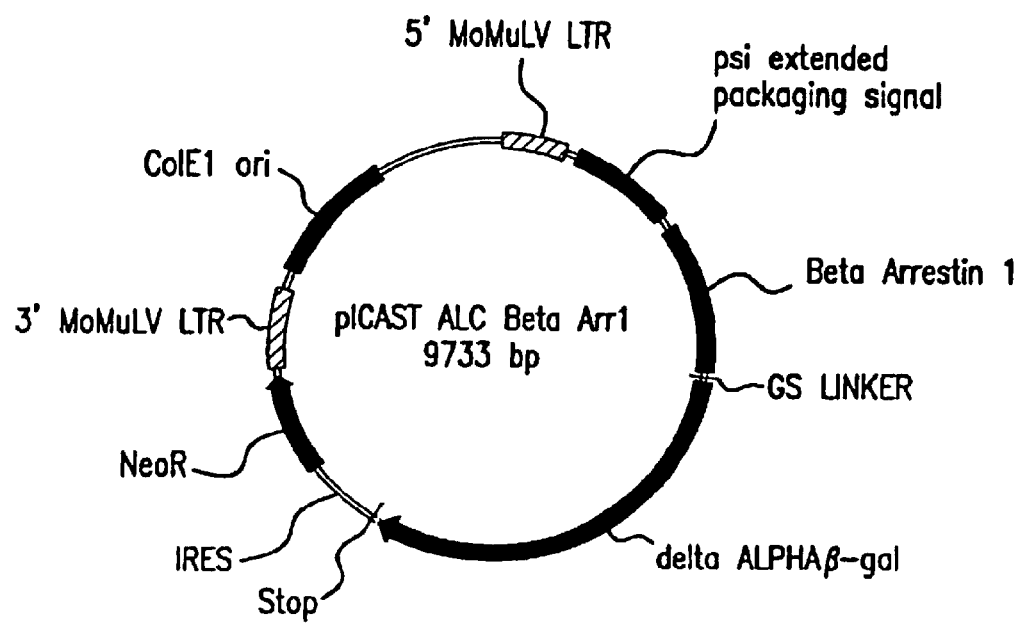
FIG. 16. pICAST ALC βArr1: Vector for expression of β-galΔα as a C-terminal fission to β-arrestin-1. The coding sequence of human β-arrestin-1 (Genebank Accession Number: NM_004041) was cloned in frame to β-galΔα in a pICAST ALC vector.
Figure 17:
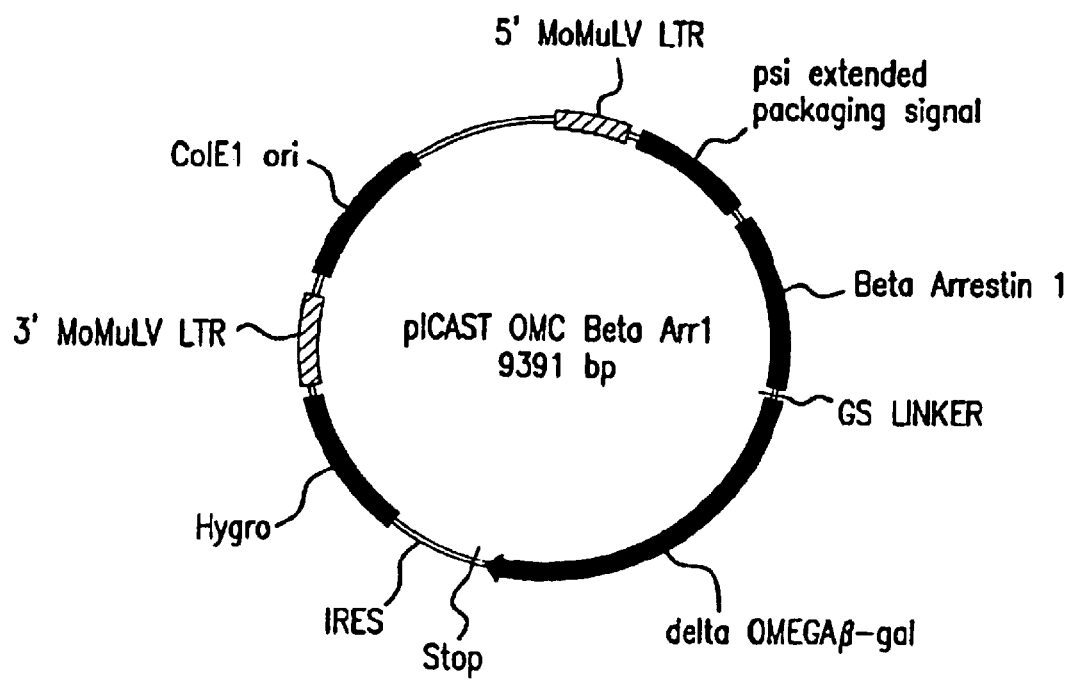
FIG. 17. pICAST OMC βArr1: Vector for expression of β-galΔω as a C-terminal fusion to β-arrestin-1. The coding sequence of human β-arrestin-1 (Genebank Accession Number: NM_004041) was cloned in frame to β-galΔω in a pICAST OMC vector.
Figure 18:
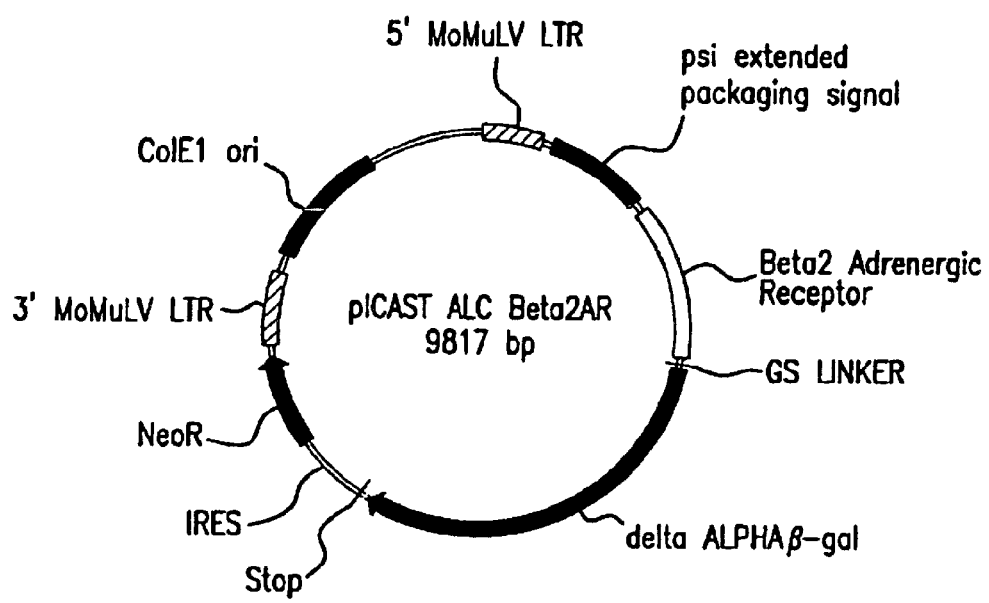
FIG. 18. pICAST ALC β2AR: Vector for expression of β-galΔα as a C-terminal fusion to β2 Adrenergic Receptor. The coding sequence of human β2 Adrenergic Receptor (Genebank Accession Number: NM_000024) was cloned in frame to β-galΔα in a pICAST ALC vector.
Figure 19:
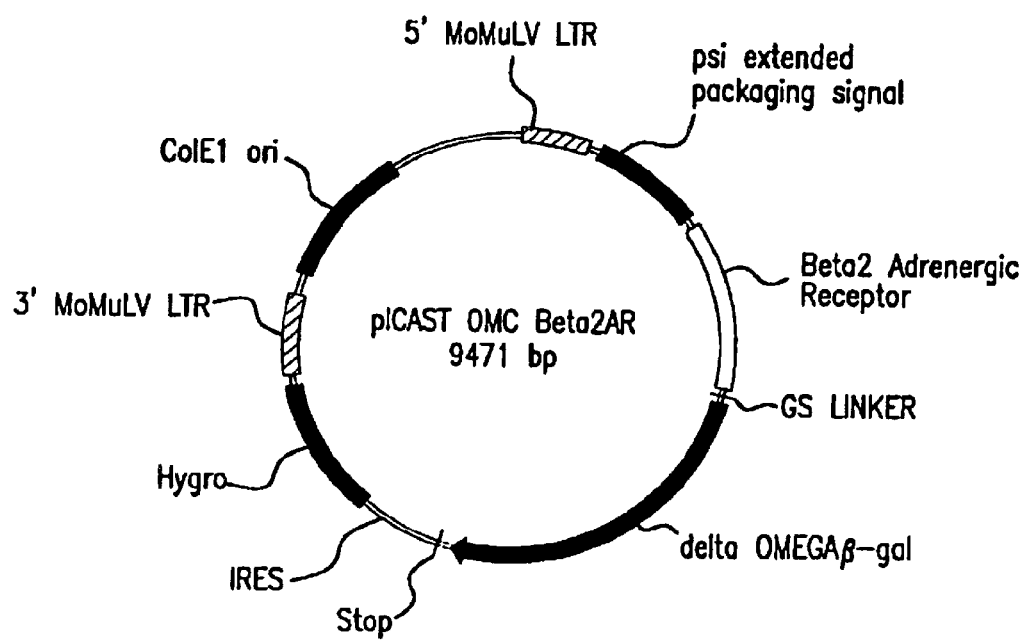
FIG. 19. pICAST OMC β2AR: Vector for expression of β-galΔω as a C-terminal fusion β2 Adrenergic Receptor. The coding sequence of human β2 Adrenergic Receptor (Genebank Accession Number: NM_000024) was cloned in frame to β-galΔω in a pICAST OMC vector.
Figure 20:
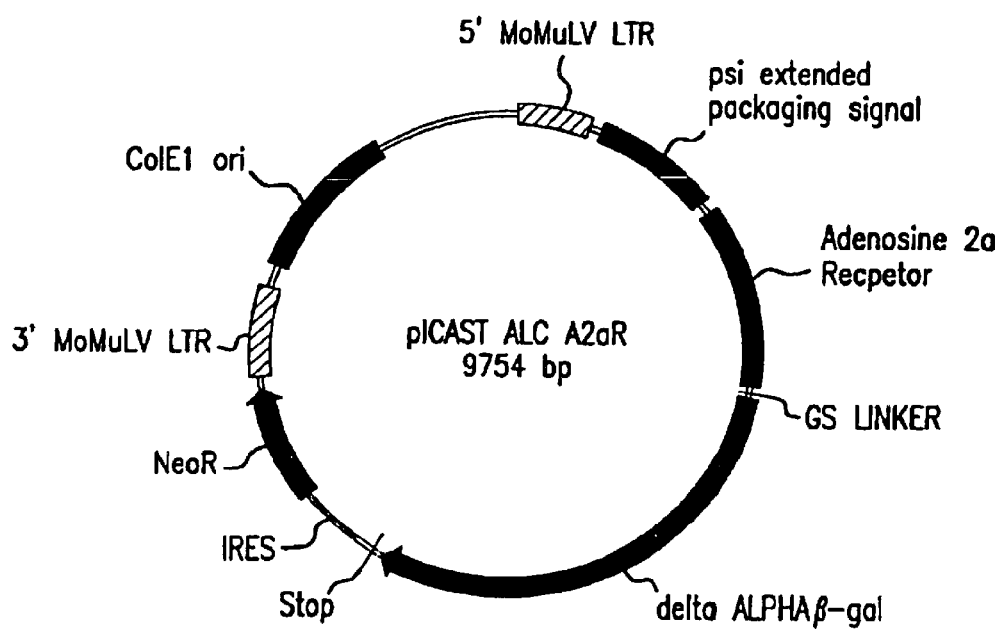
FIG. 20. pICAST ALC A2aR: Vector for expression of β-galΔα as a C-terminal fusion to Adenosine 2a Receptor. The coding sequence of human Adenosine 2a Receptor (Genebank Accession Number: NM_000675) was cloned in frame to β-galΔα in a pICAST ALC vector.
Figure 21:
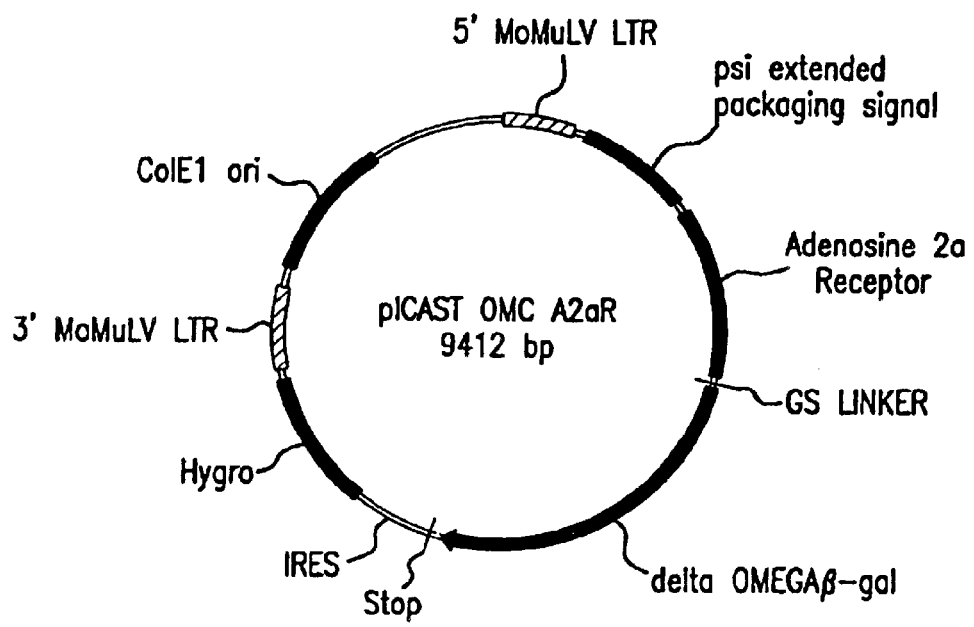
FIG. 21. pICAST OMC A2aR: Vector for expression of β-galΔω as a C-terminal fusion to Adenosine 2a Receptor. The coding sequence of human Adenosine 2a Receptor (Genebank Accession Number: NM_000675) was cloned in frame to β-galΔω in a pICAST OMC vector.
Figure 22:
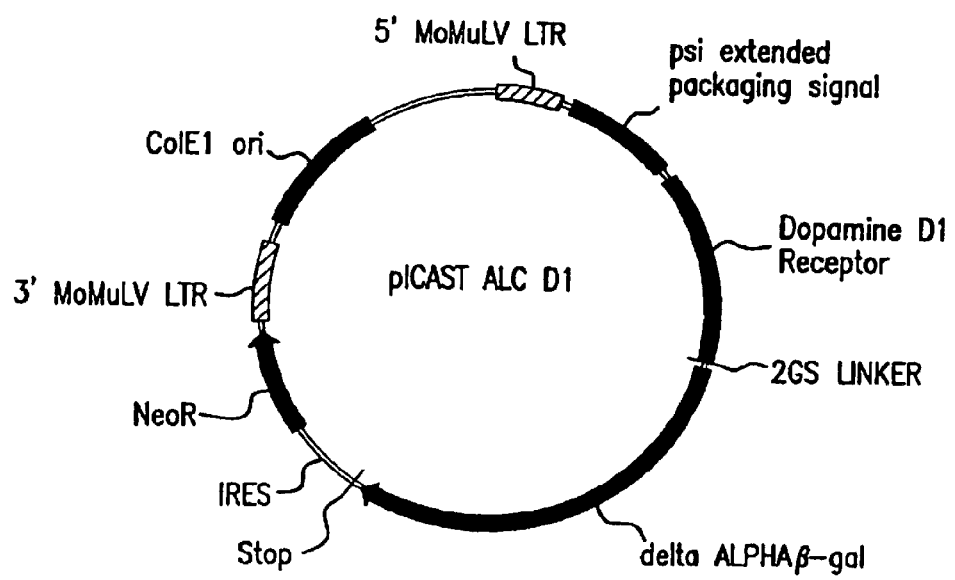
FIG. 22. pICAST ALC D1: Vector for expression of β-galΔα as a C-terminal fusion to Dopamine D1 Receptor. The coding sequence of human Dopamine D1 Receptor (Genebank Accession Number: X58987) was cloned in frame to β-galΔα in a pICAST ALC vector.
Figure 23:
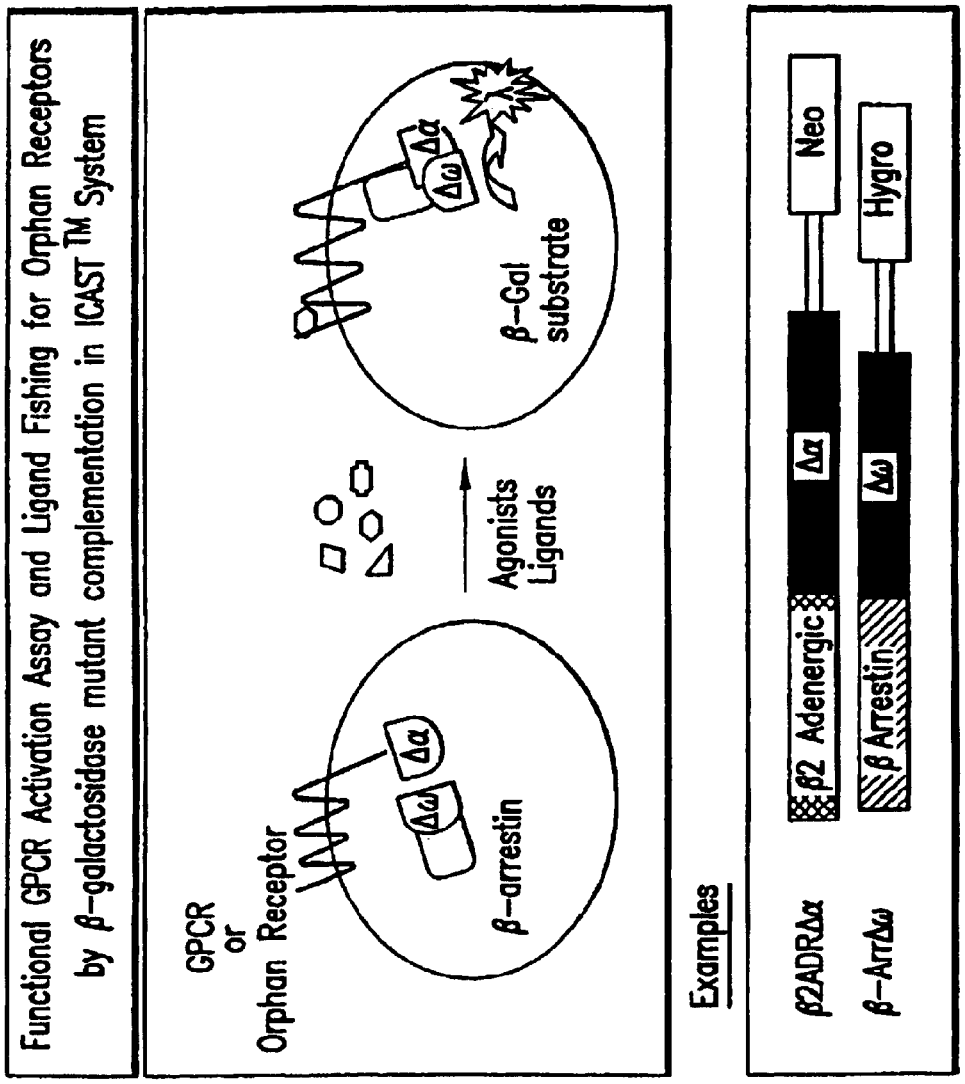
FIG. 23. A schematic depicting the method of the invention, which shows that two inactive mutants become active when they interact.

1. In the first step, the expression vectors for β2ADRΔα and βArr2Δω were engineered in selectable retroviral vectors pICAST ALC, as described in FIG. 18 and pICAST OMC, as in FIG. 15.

2. In the second step, the two expression constructs were transduced into either C2C12 myoblast cells, or other mammalian cell lines, such as COS-7, CHO, A431, HEK 293, and CHW. Following selection with antibiotic drugs, stable clones expressing both fusion proteins at appropriate levels were selected.

Figure 3A:
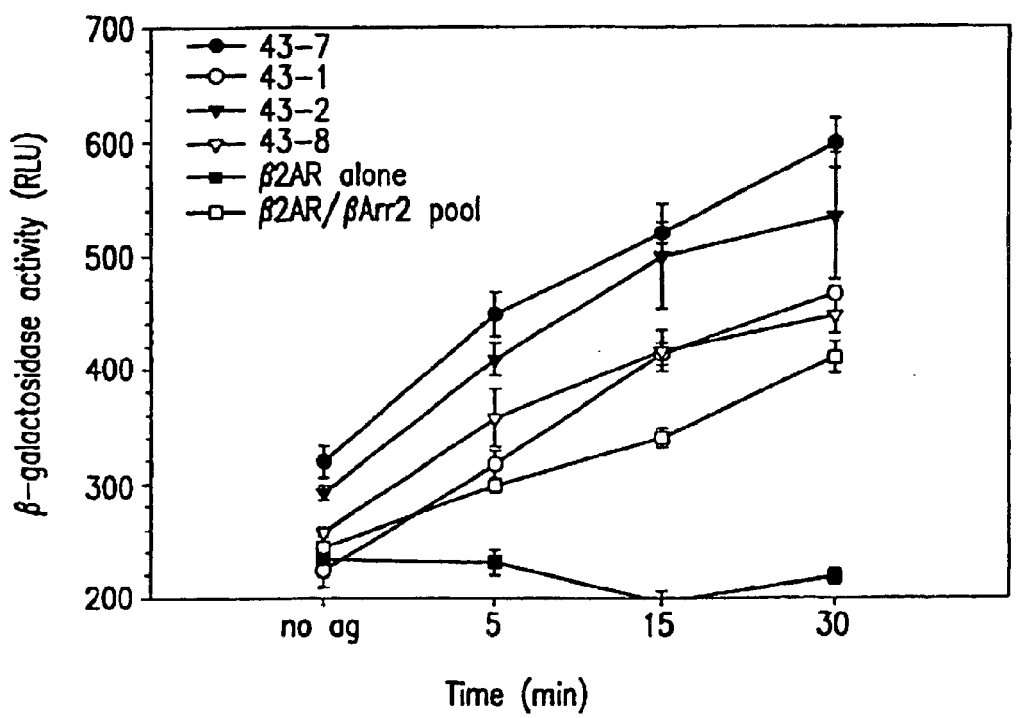
FIG. 3A shows a time course of β-galactosidase activity in response to agonist (−)isoproterenol stimulation in C2 expressing β2AR-βgalΔα (β2AR alone, in expression vector pICAST ALC), or C2 clones, and a pool of C2 co-expressing β2AR-βgalΔα and βArr2-βgalΔω (in expression vectors pICAST ALC and pICAST OMC).
Figure 3B:
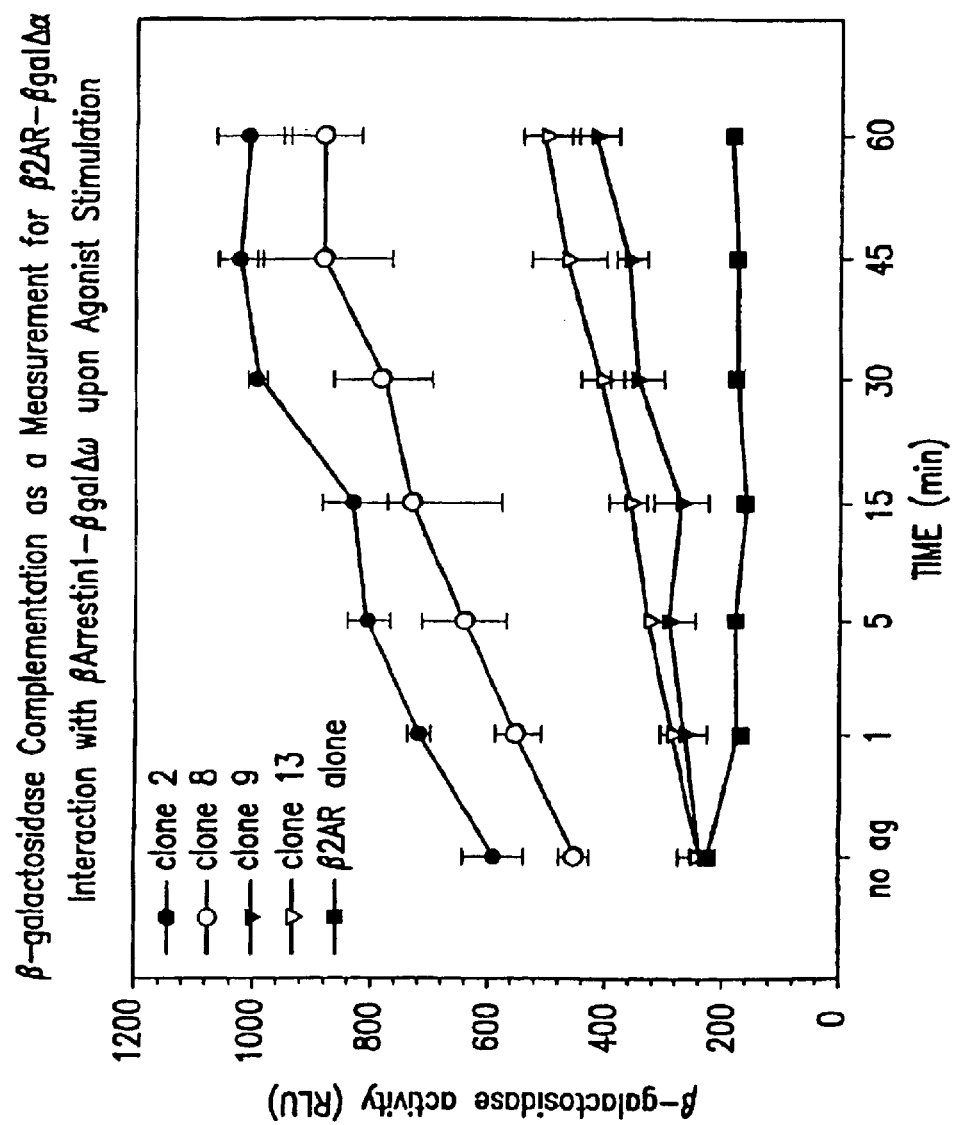
FIG. 3B shows a time course of β-galactosidase activity in response to agonist (−)isoproterenol stimulation in C2 cells expressing β2AR alone (in expression vector pICAST ALC) and C2 clones co-expressing β2AR and βArr1 (in expression vectors ICAST ALC and pICAST OMC).
Figure 4A:
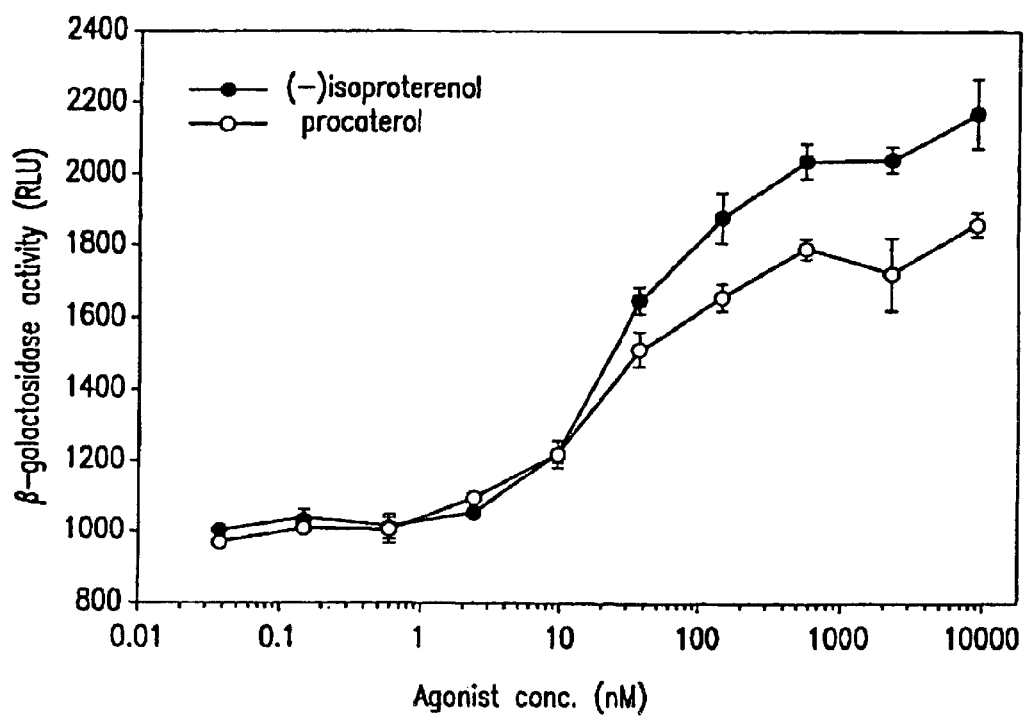
FIG. 4A shows a dose response to agonists (−)isoproterenol and procaterol in C2 cells co-expressing pICAST ALC β2AR and pICAST OMC βArr2 fusion constructs.
Figure 4B:
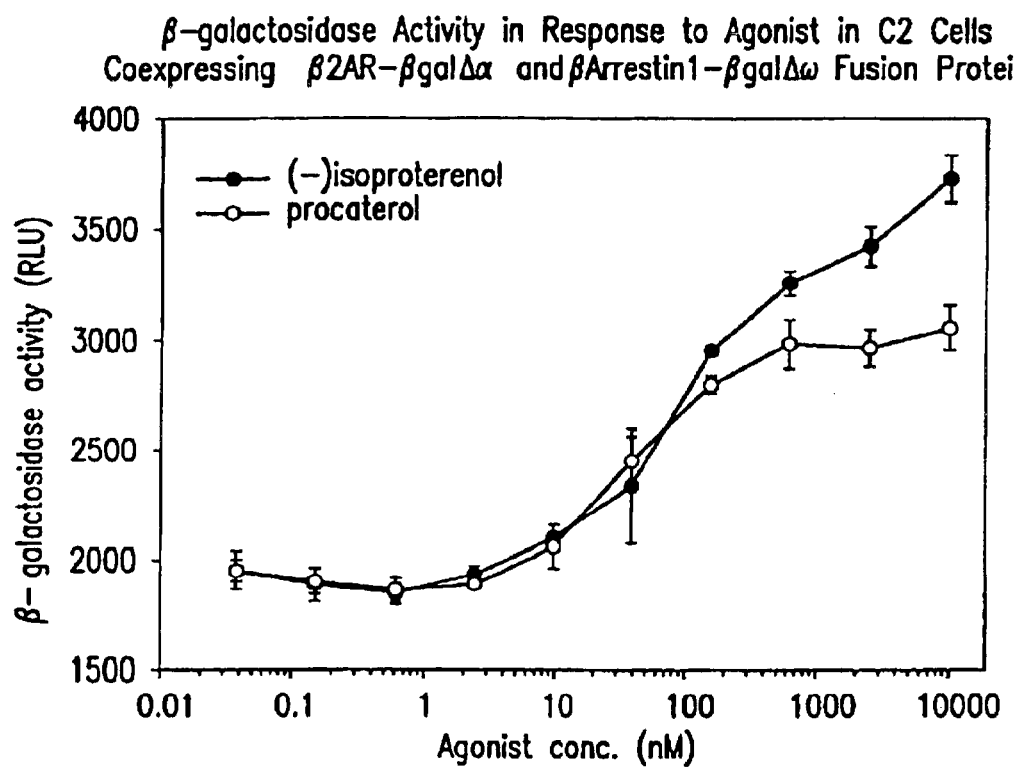
FIG. 4B shows a dose response to agonists (−)isoproterenol and procaterol in C2 cells co-expressing pICAST ALC β2AR and pICAST OMC βArr1 fusion constructs.
Figure 5A:
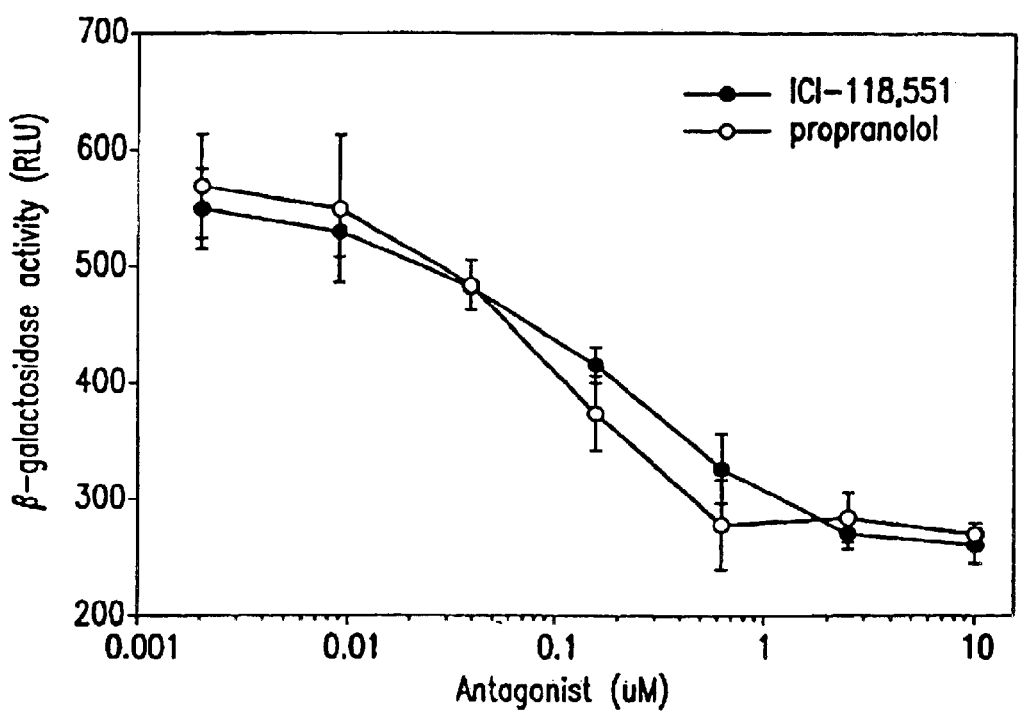
FIG. 5A shows specific inhibition with adrenergic antagonists ICI-118,551 and propranolol of β-galactosidase activity in C2 clones co-expressing pICAST ALC β2AR and pICAST OMC βArr2 fusion constructs after incubation with agonist (−)isoproterenol.
Figure 5B:
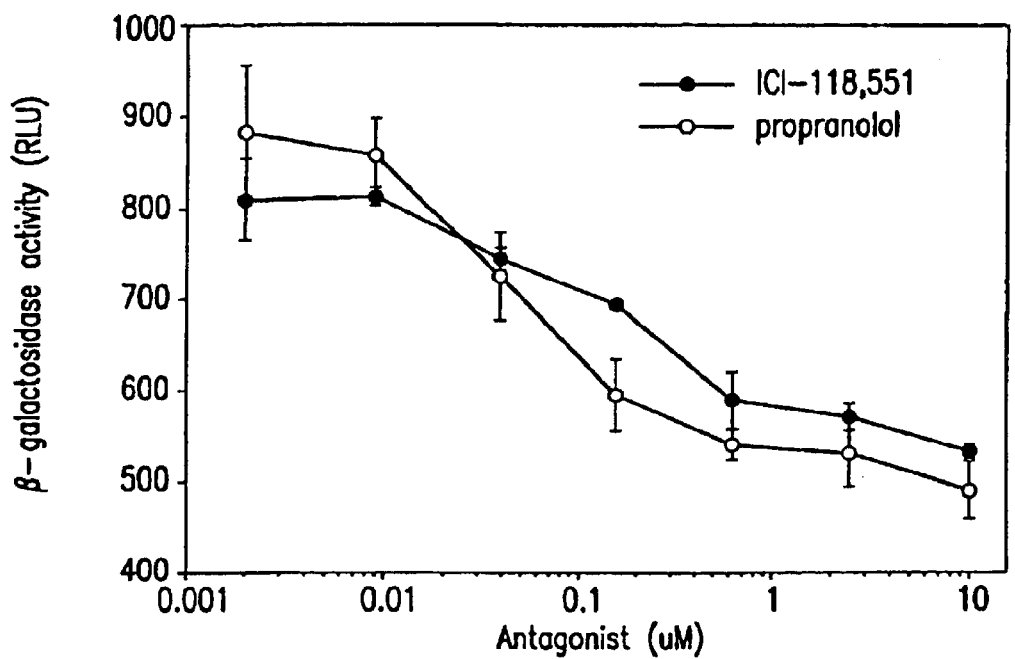
FIG. 5B shows specific inhibition of β-galactosidase activity with adrenergic antagonists ICI-118,551 and propranolol in C2 clones co-expressing pICAST ALC β2AR and pICAST OMC βArr1 fusion constructs in the presence of agonist (−)isoproterenol.
Figure 6:
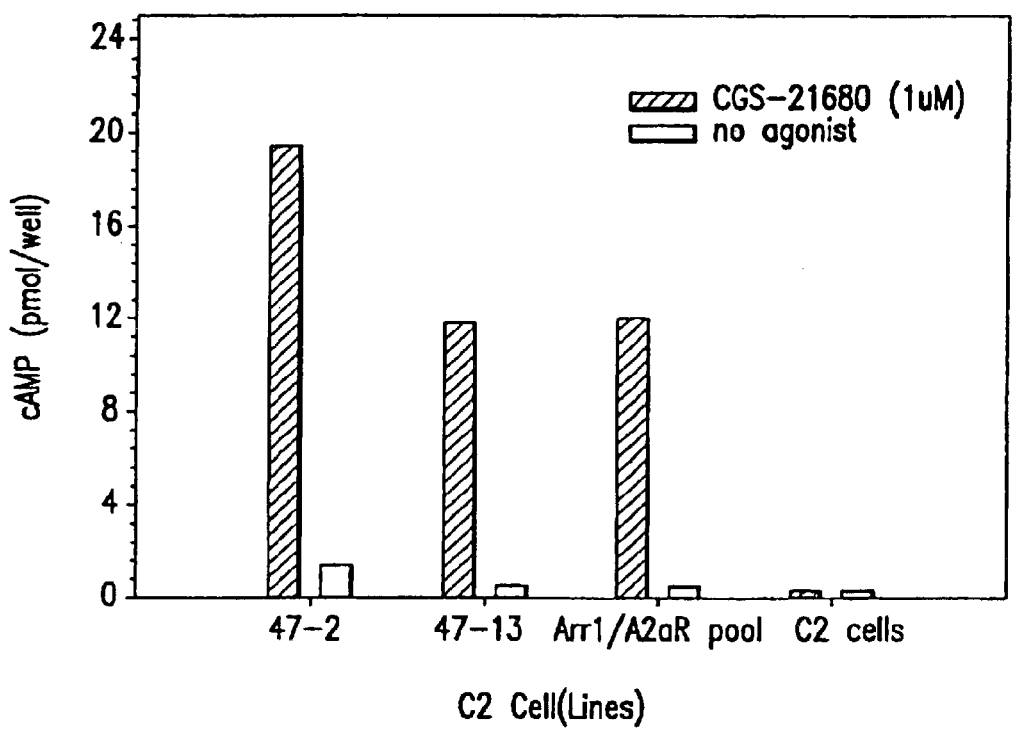
FIG. 6. C2 cells expressing adenosine receptor A2a show cAMP induction in response to agonist (CGC-21680) treatment. C2 parental cells and C2 cells co-expressing pICAST ALC A2aR and pICAST OMC βArr1 as a pool or as selected clones were measured for agonist-induced cAMP response (pmol/well).
Figure 7:
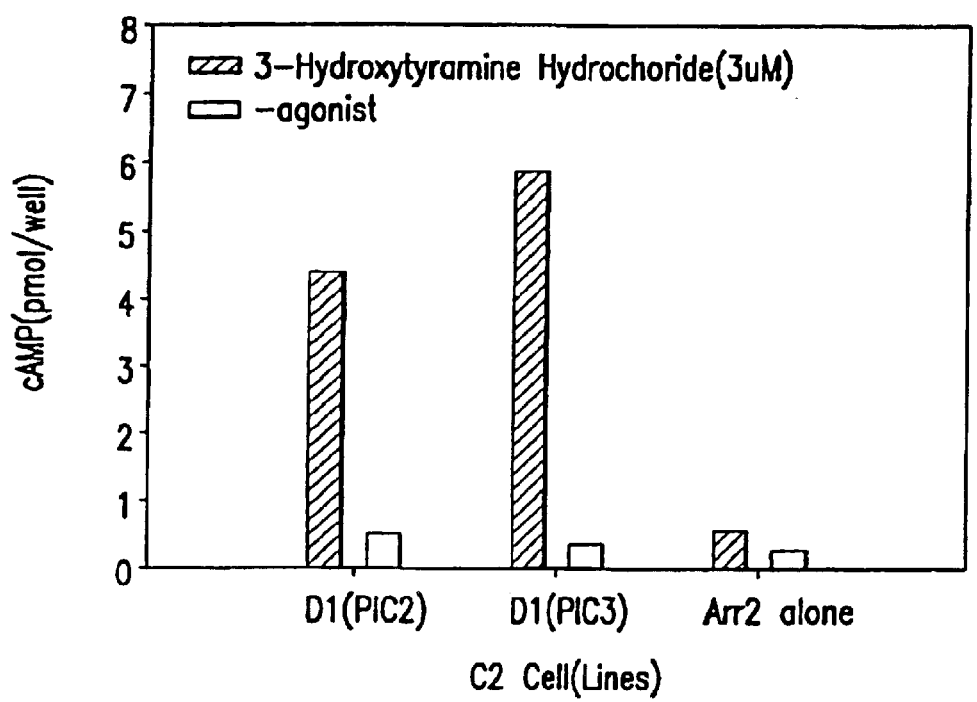
FIG. 7. Agonist stimulated cAMP response in C2 cells co-expressing Dopamine receptor D1 (D1-βgalΔα) and β-arrestin-2 (βArr2-βgalΔω). The clone expressing βArr2-βgalΔω (Arr2 alone) was used as a negative control in the assay. Cells expressing D1-βgalΔα in addition to βArr2-βgalΔω responded to treatment with agonist (3-hydroxytyramine hydrochloride at 3 μM). D1(PIC2) or D1(PIC3) designate D1 in expression vector pICAST ALC2 or pICAST ALC4, respectively.
Figure 8A:
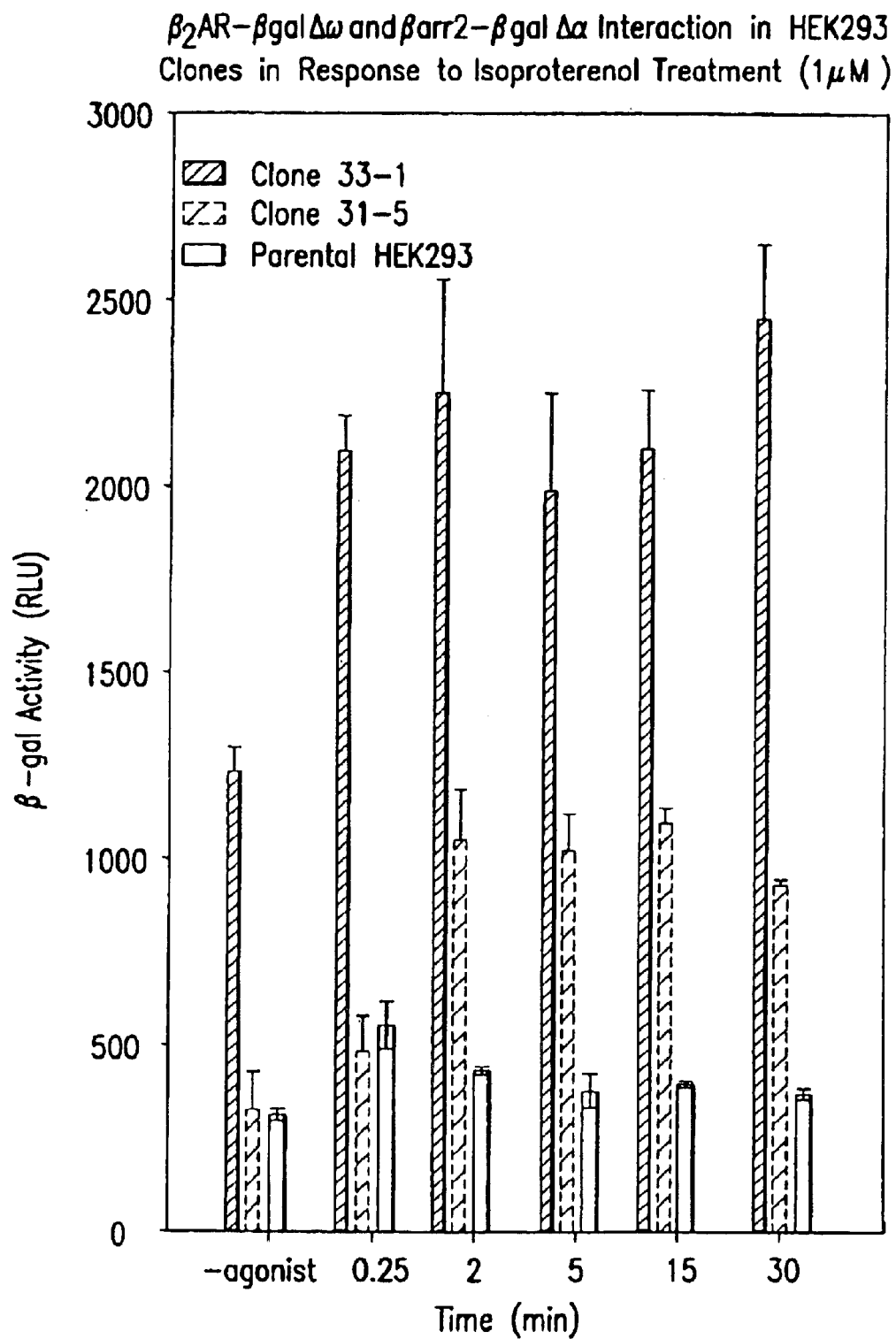
FIG. 8A, FIG. 8B and FIG. 8C show the examples of HEK293, CHO and CHW cell lines co-expressing adrenergic receptor β2AR and arrestin fusion proteins of β-galactosidase mutants. The β-galactosidase activity was used to monitor agonist-induced interaction of β2AR and arrestin proteins.
Figure 8B:
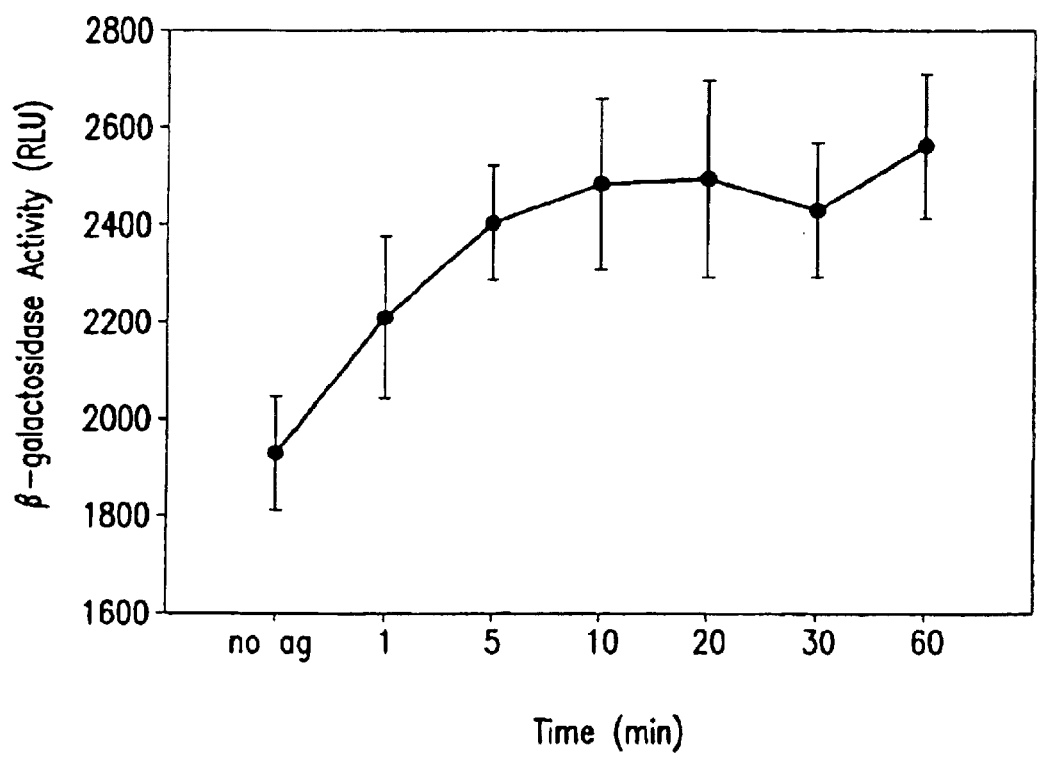
Figure 8C:
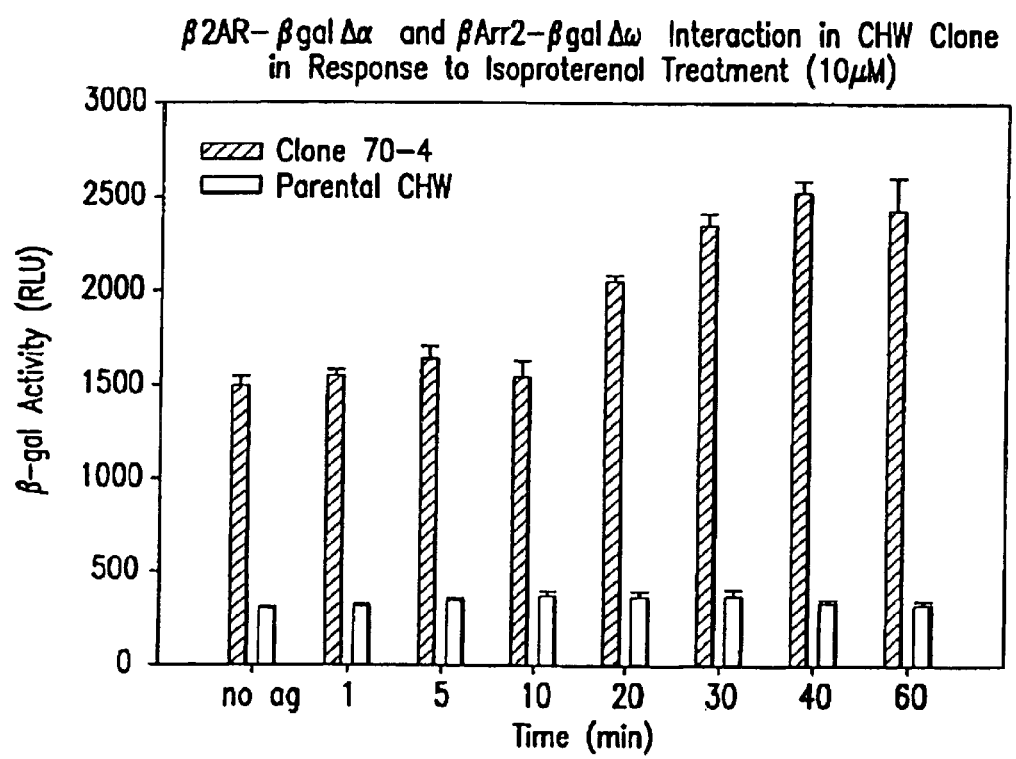
Figure 9A:
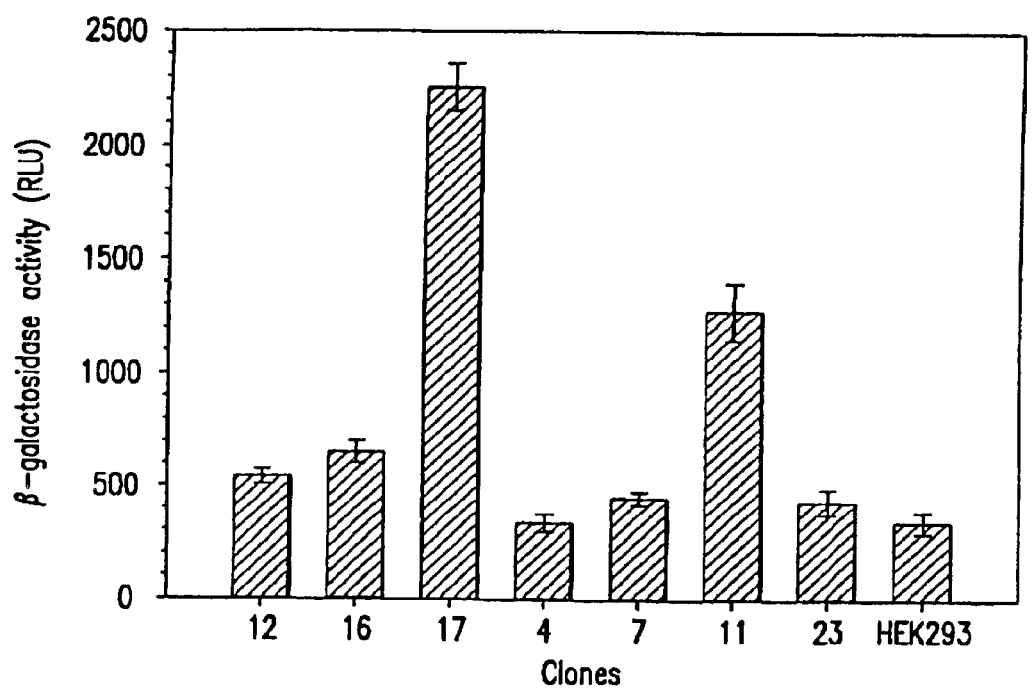
FIG. 9A shows β-galactosidase activity in HEK293 clones co-expressing pICAST ALC β2AR and pICAST OMC β2AR.
Figure 9B:
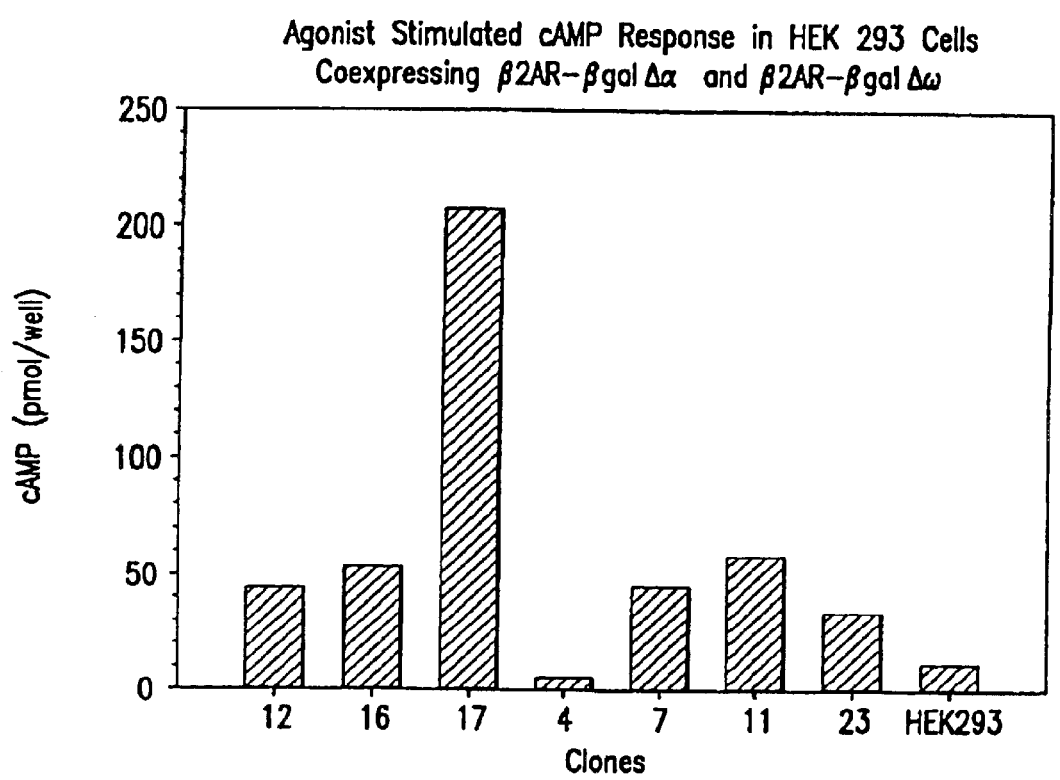
FIG. 9B shows a cAMP response to agonist (−)isoproterenol in HEK 293 clones co-expressing pICAST ALC β2AR and pICAST OMC β2AR. HEK293 parental cells were included in the assays as negative controls.
Figure 10A:
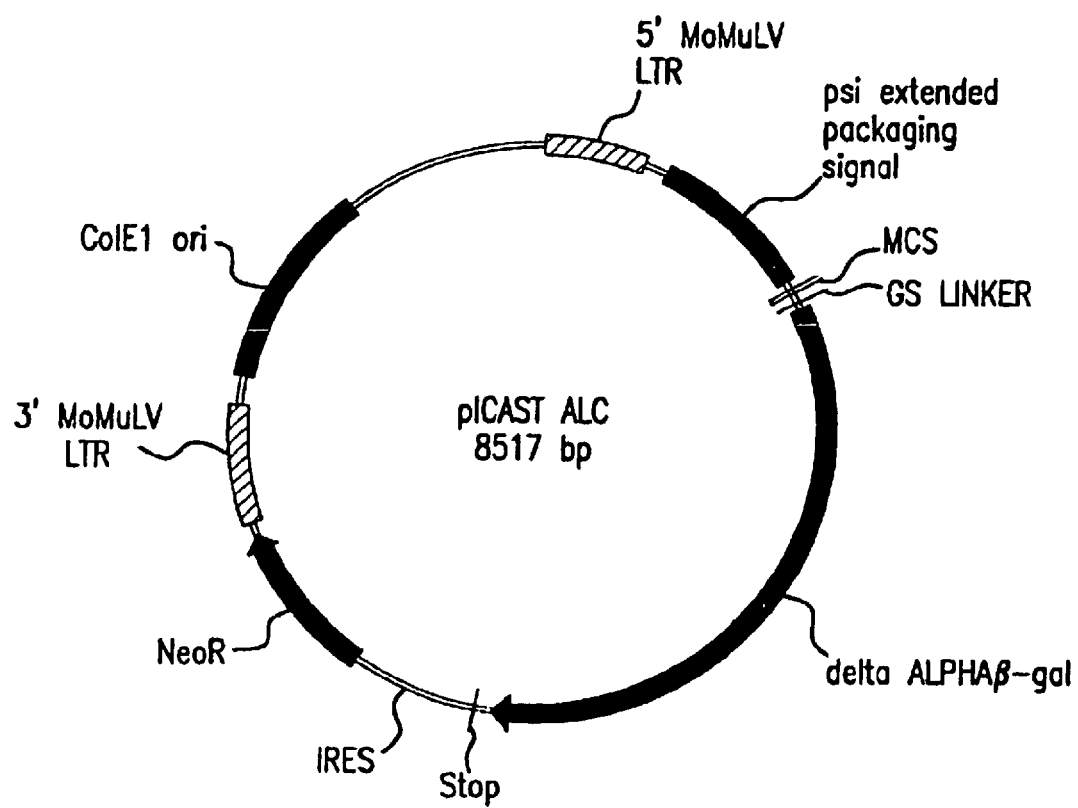
FIG. 10A. pICAST ALC: Vector for expression of β-galΔα as a C-terminal fusion to the target protein. This construct contains the following features: MCS, multiple cloning site for cloning the target protein in frame with the β-galΔα; GS Linker, (GGGGS)n (SEQ ID NO:6); NeoR, neomycin resistance gene; IRES, internal ribosome entry site; ColElori, origin of replication for growth in E. coli; 5'MoMuLV LTR and 3'MoMuLV LTR, viral promotor and polyadenylation signals from the Moloney Murine leukemia virus.
Figure 11A:
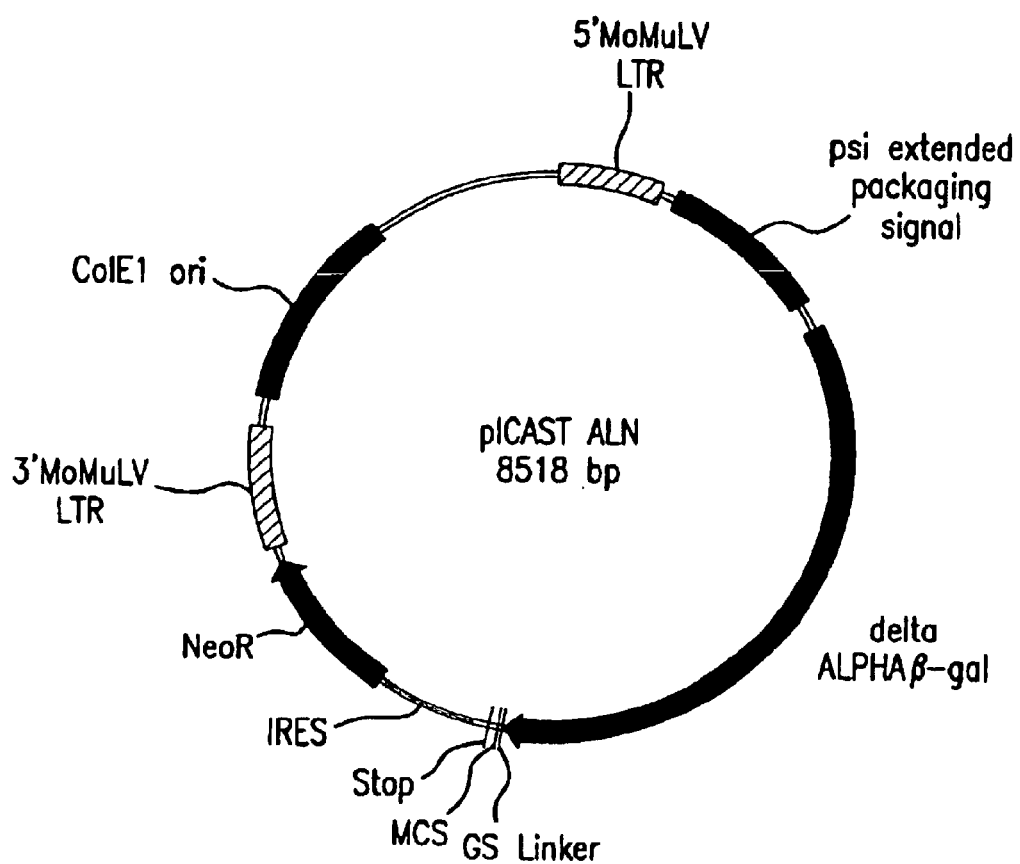
FIG. 11A. pICAST ALN: Vector for expression of β-galΔα as an N-terminal fusion to the target protein. This construct contains the following features: MCS, multiple cloning site for cloning the target protein in frame with the β-galΔα; GS Linker, (GGGGS)n (SEQ ID NO:6); NeoR, neomycin resistance gene; IRES, internal ribosome entry site; ColElori, origin of replication for growth in E. coli; 5'MoMuLV LTR and 3'MoMuLV LTR, viral promotor and polyadenylation signals from the Moloney Murine leukemia virus.
Figure 12A:
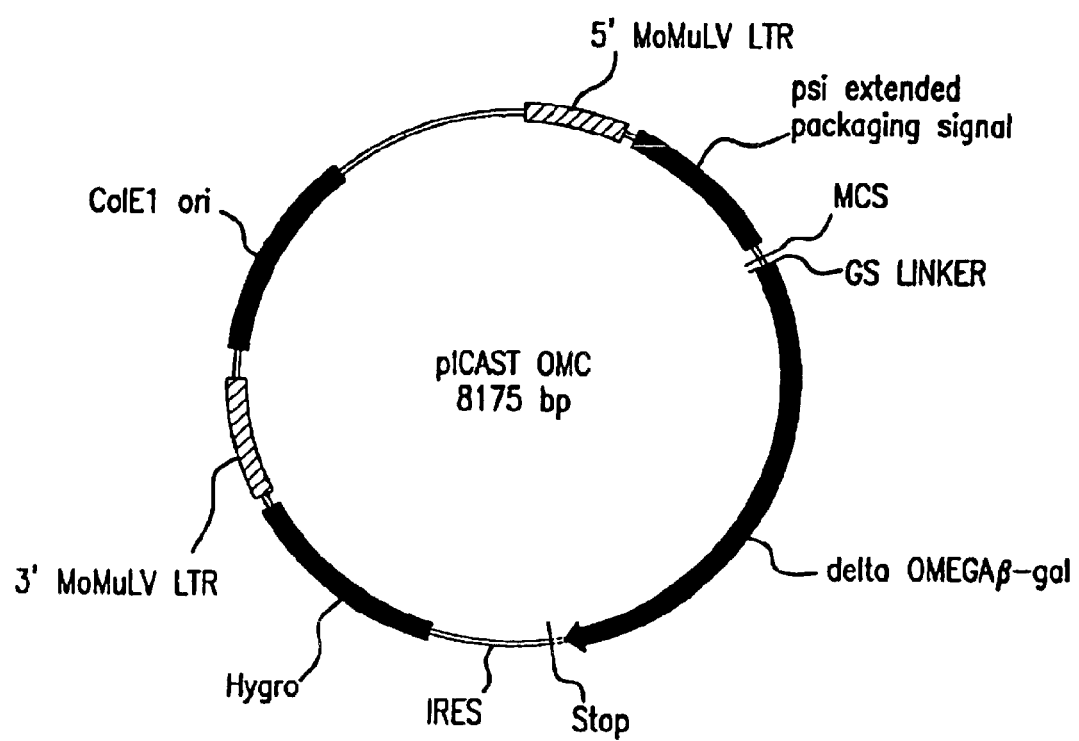
FIG. 12A. pICAST OMC: Vector for expression of β-galΔω as a C-terminal fusion to the target protein. This construct contains the following features: MCS, multiple cloning site for cloning the target protein in frame with the β-galΔω; GS Linker, (GGGGS)n (SEQ ID NO:6); Hygro, hygromycin resistance gene; IRES, internal ribosome entry site; ColE 1 ori, origin of replication for growth in *E. coli*; 5'MoMuLV LTR and 3'MoMuLV LTR, viral promotor and polyadenylation signals from the Moloney Murine leukemia virus.
Figure 13A:
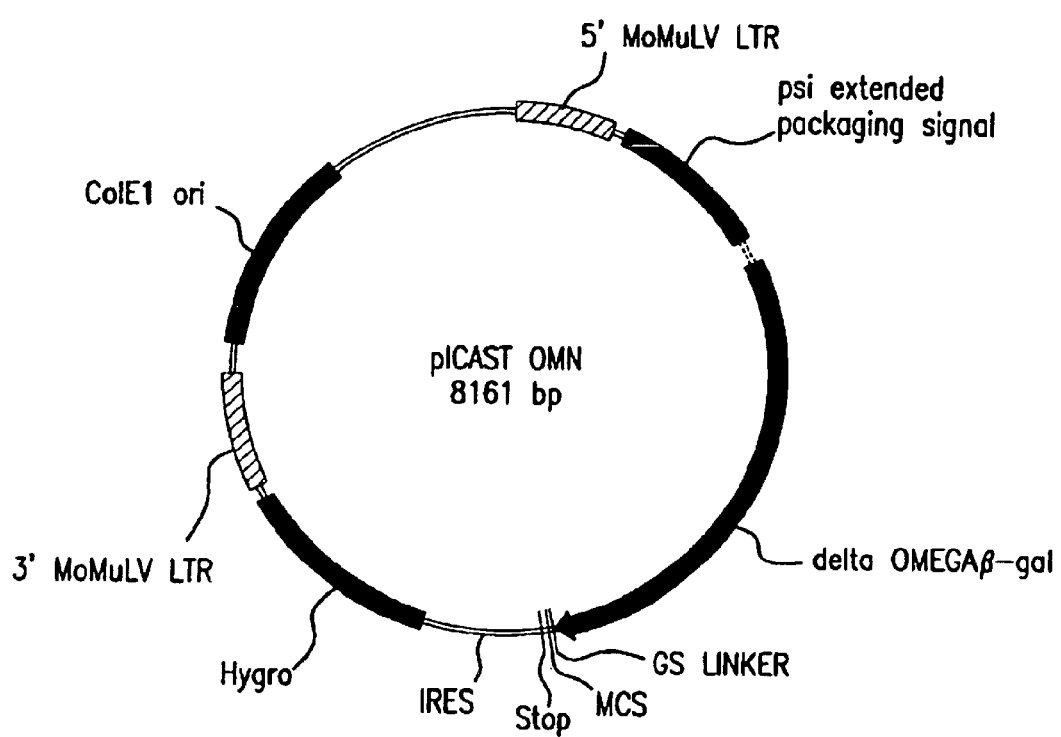
FIG. 13A. pICAST OMN: Vector for expression of β-galΔω as an N-terminal fusion to the target protein. This construct contains the following features: MCS, multiple cloning site for cloning the target protein in frame with the β-galΔω; GS Linker, (GGGGS)n (SEQ ID NO:6); Hygro, hygromycin resistance gene; IRES, internal ribosome entry site; ColE1ori, origin of replication for growth in *E. coli*; 5'MoMuLV LTR and 3'MoMuLV LTR, viral promotor and polyadenylation signals from the Moloney Murine leukemia virus.
Figure 14:
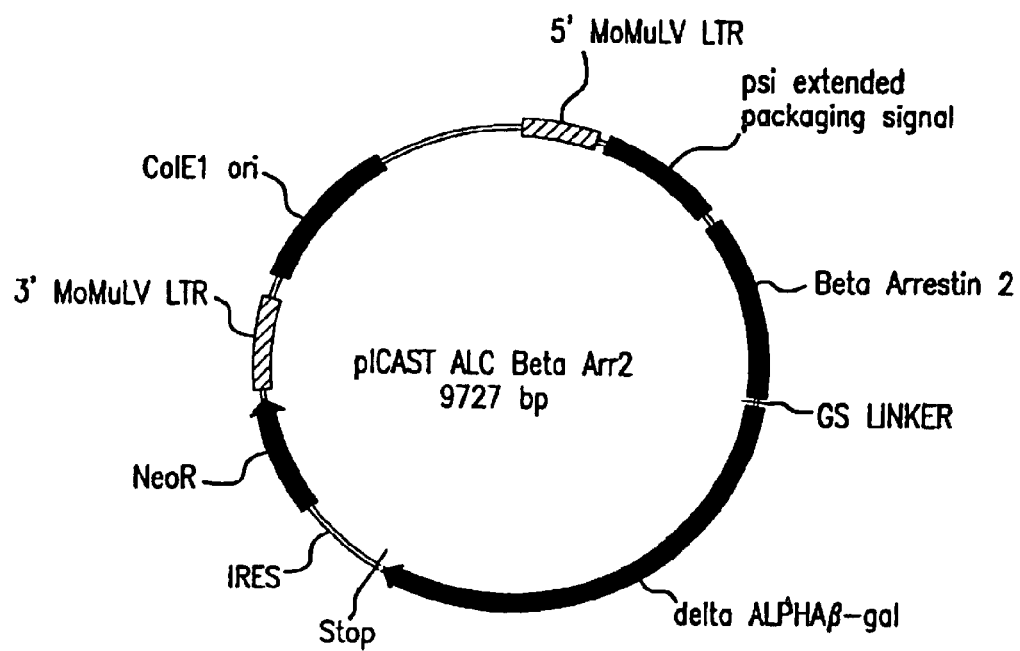
FIG. 14. pICAST ALC βArr2: Vector for expression of β-galΔα as a C-terminal fusion to β-arrestin-2. The coding sequence of human β-arrestin-2 (Genebank Accession Number: NM_004313) was cloned in frame to β-galΔα in a pICAST ALC vector.

3. In the last step, the cells expressing both β2ADRΔα and βArr2Δω were tested for response by agonist/ligand stimulated β-galactosidase activity. Triplicate samples of cells were plated at 10,000 cells in 100 microliter volume into a well of 96-well culture plate. Cells were cultured for 24 hours before assay. For an agonist assay (FIGS. 3 and 4), cells were treated with variable concentrations of agonist, for example, (−) isoproterenol, procaterol, dobutamine, terbutaline or L-phenylephrine for 60 min at 37° C. The induced β-galactosidase activity was measured by addition of Tropix GalScreen® substrate (Applied Biosystems) and luminescence measured in a TR717™ luminometer (Applied Biosystems). For antagonist assay (FIG. 5), cells were pre-incubated for 10 min in fresh medium without serum in the presence of ICI-118,551 or propranolol followed by addition of 10 micromolar (−) isoproterenol.

The assays of this invention, and their application and preparation have been described both generically, and by specific example. The examples are not intended as limiting. Other substituent identities, characteristics and assays will occur to those of ordinary skill in the art, without the exercise of inventive faculty. Such modifications remain within the scope of the invention, unless excluded by the express recitation of the claims advanced below.

SEQUENCE LISTING

```
<160> NUMBER OF SEQ ID NOS: 6

<210> SEQ ID NO 1
<211> LENGTH: 6700
<212> TYPE: DNA
<213> ORGANISM: Artificial Sequence
<220> FEATURE:
<223> OTHER INFORMATION: Nucleotide sequence for pICAST ALC
<220> FEATURE:
<221> NAME/KEY: CDS
<222> LOCATION: (1457)...(4486)

<400> SEQUENCE: 1
```

-continued

```
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca cccctcact  cggggcgcca gtcctccgat tgactgagtc     360
gcccgggtac ccgtgtatcc aataaaccct cttgcagttg catccgactt gtggtctcgc     420
tgttccttgg gagggtctcc tctgagtgat tgactacccg tcagcggggg tctttcattt     480
gggggctcgt ccgggatcgg gagaccctg  cccaggggacc accgaccac  caccgggagg    540 caagctggcc agcaacttat ctgtgtctgt ccgattgtct agtgtctatg actgattta     600 tgcgcctgcg tcggtactag ttagctaact agctctgtat ctggcggacc cgtggtggaa    660
ctgacgagtt ctgaacaccc ggccgcaacc ctggagacg  tcccagggac tttggggcc     720 gttttttgtgg cccgacctga ggaagggagt cgatgtggaa tccgaccccg tcaggatatg    780
tggttctggt aggagacgag aacctaaaac agttcccgcc tccgtctgaa ttttttgctt     840
cggtttggaa ccgaagccgc gcgtcttgtc tgctgcagca tcgttctgtg ttgtctctgt     900
ctgactgtgt ttctgtattt gtctgaaaat tagggccaga ctgttaccac tcccttaagt     960
ttgaccttag gtaactggaa agatgtcgag cggctcgctc acaaccagtc ggtagatgtc   1020
aagaagagac gttgggttac cttctgctct gcagaatggc caacctttaa cgtcggatgg   1080
ccgcgagacg gcaacctttaa ccgagaccctc atcacccagg ttaagatcaa ggtcttttca   1140
cctggcccgc atggacaccc agaccaggtc ccctacatcg tgacctggga agccttggct    1200
tttgaccccc ctccctgggt caagcccttt gtacacccta gcctccgcc  tcctcttcct   1260 ccatccgccc cgtctctccc ccttgaacct cctcgttcga cccgcctcg  atcctcctt    1320 tatccagccc tcactccttc tctaggcgcc ggccgctcta gcccattaat acgactcact   1380 ataggcgat  tcgaatcagg ccttggcgcg ccggatcctt aattaagcgc aattgggagg   1440
tggcggtagc ctcgag atg ggc gtg att acg gat tca ctg gcc gtc gtg gcc   1492
              Met Gly Val Ile Thr Asp Ser Leu Ala Val Val Ala
                1               5                  10 cgc acc gat cgc cct tcc caa cag tta cgc agc ctg aat ggc gaa tgg    1540
Arg Thr Asp Arg Pro Ser Gln Gln Leu Arg Ser Leu Asn Gly Glu Trp
         15                  20                  25 cgc ttt gcc tgg ttt ccg gca cca gaa gcg gtg ccg gaa agc tgg ctg    1588
Arg Phe Ala Trp Phe Pro Ala Pro Glu Ala Val Pro Glu Ser Trp Leu
    30                  35                  40 gag tgc gat ctt cct gag gcc gat act gtc gtc gtc ccc tca aac tgg    1636
Glu Cys Asp Leu Pro Glu Ala Asp Thr Val Val Val Pro Ser Asn Trp
 45                  50                  55                  60 cag atg cac ggt tac gat gcg ccc atc tac acc aac gtg acc tat ccc    1684
Gln Met His Gly Tyr Asp Ala Pro Ile Tyr Thr Asn Val Thr Tyr Pro
                 65                  70                  75 att acg gtc aat ccg ccg ttt gtt ccc acg gag aat ccg acg ggt tgt    1732
Ile Thr Val Asn Pro Pro Phe Val Pro Thr Glu Asn Pro Thr Gly Cys
             80                  85                  90 tac tcg ctc aca ttt aat gtt gat gaa agc tgg cta cag gaa ggc cag    1780
Tyr Ser Leu Thr Phe Asn Val Asp Glu Ser Trp Leu Gln Glu Gly Gln
         95                 100                 105 acg cga att att ttt gat ggc gtt aac tcg gcg ttt cat ctg tgg tgc    1828
Thr Arg Ile Ile Phe Asp Gly Val Asn Ser Ala Phe His Leu Trp Cys
```

```
              110                 115                 120
aac ggg cgc tgg gtc ggt tac ggc cag gac agt cgt ttg ccg tct gaa    1876
Asn Gly Arg Trp Val Gly Tyr Gly Gln Asp Ser Arg Leu Pro Ser Glu
125                 130                 135                 140 ttt gac ctg agc gca ttt tta cgc gcc gga gaa aac cgc ctc gcg gtg    1924
Phe Asp Leu Ser Ala Phe Leu Arg Ala Gly Glu Asn Arg Leu Ala Val
                145                 150                 155 atg gtg ctg cgc tgg agt gac ggc agt tat ctg gaa gat cag gat atg    1972
Met Val Leu Arg Trp Ser Asp Gly Ser Tyr Leu Glu Asp Gln Asp Met
                160                 165                 170 tgg cgg atg agc ggc att ttc cgt gac gtc tcg ttg ctg cat aaa ccg    2020
Trp Arg Met Ser Gly Ile Phe Arg Asp Val Ser Leu Leu His Lys Pro
            175                 180                 185 act aca caa atc agc gat ttc cat gtt gcc act cgc ttt aat gat gat    2068
Thr Thr Gln Ile Ser Asp Phe His Val Ala Thr Arg Phe Asn Asp Asp
        190                 195                 200 ttc agc cgc gct gta ctg gag gct gaa gtt cag atg tgc ggc gag ttg    2116
Phe Ser Arg Ala Val Leu Glu Ala Glu Val Gln Met Cys Gly Glu Leu
205                 210                 215                 220 cgt gac tac cta cgg gta aca gtt tct tta tgg cag ggt gaa acg cag    2164
Arg Asp Tyr Leu Arg Val Thr Val Ser Leu Trp Gln Gly Glu Thr Gln
                225                 230                 235 gtc gcc agc ggc acc gcg cct ttc ggc ggt gaa att atc gat gag cgt    2212
Val Ala Ser Gly Thr Ala Pro Phe Gly Gly Glu Ile Ile Asp Glu Arg
                240                 245                 250 ggt ggt tat gcc gat cgc gtc aca cta cgt ctg aac gtc gaa aac ccg    2260
Gly Gly Tyr Ala Asp Arg Val Thr Leu Arg Leu Asn Val Glu Asn Pro
            255                 260                 265 aaa ctg tgg agc gcc gaa atc ccg aat ctc tat cgt gcg gtg gtt gaa    2308
Lys Leu Trp Ser Ala Glu Ile Pro Asn Leu Tyr Arg Ala Val Val Glu
        270                 275                 280 ctg cac acc gcc gac ggc acg ctg att gaa gca gaa gcc tgc gat gtc    2356
Leu His Thr Ala Asp Gly Thr Leu Ile Glu Ala Glu Ala Cys Asp Val
285                 290                 295                 300 ggt ttc cgc gag gtg cgg att gaa aat ggt ctg ctg ctg ctg aac ggc    2404
Gly Phe Arg Glu Val Arg Ile Glu Asn Gly Leu Leu Leu Leu Asn Gly
                305                 310                 315 aag ccg ttg ctg att cga ggc gtt aac cgt cac gag cat cat cct ctg    2452
Lys Pro Leu Leu Ile Arg Gly Val Asn Arg His Glu His His Pro Leu
                320                 325                 330 cat ggt cag gtc atg gat gag cag acg atg gtg cag gat atc ctg ctg    2500
His Gly Gln Val Met Asp Glu Gln Thr Met Val Gln Asp Ile Leu Leu
            335                 340                 345 atg aag cag aac aac ttt aac gcc gtg cgc tgt tcg cat tat ccg aac    2548
Met Lys Gln Asn Asn Phe Asn Ala Val Arg Cys Ser His Tyr Pro Asn
350                 355                 360 cat ccg ctg tgg tac acg ctg tgc gac cgc tac ggc ctg tat gtg gtg    2596
His Pro Leu Trp Tyr Thr Leu Cys Asp Arg Tyr Gly Leu Tyr Val Val
365                 370                 375                 380 gat gaa gcc aat att gaa acc cac ggc atg gtg cca atg aat cgt ctg    2644
Asp Glu Ala Asn Ile Glu Thr His Gly Met Val Pro Met Asn Arg Leu
                385                 390                 395 acc gat gat ccg cgc tgg cta ccg gcg atg agc gaa cgc gta acg cga    2692
Thr Asp Asp Pro Arg Trp Leu Pro Ala Met Ser Glu Arg Val Thr Arg
                400                 405                 410 atg gtg cag cgc gat cgt aat cac ccg agt gtg atc atc tgg tcg ctg    2740
Met Val Gln Arg Asp Arg Asn His Pro Ser Val Ile Ile Trp Ser Leu
            415                 420                 425 ggg aat gaa tca ggc cac ggc gct aat cac gac gcg ctg tat cgc tgg    2788
```

-continued

```
            Gly Asn Glu Ser Gly His Gly Ala Asn His Asp Ala Leu Tyr Arg Trp
                430                 435                 440 atc aaa tct gtc gat cct tcc cgc ccg gtg cag tat gaa ggc ggc gga                  2836
Ile Lys Ser Val Asp Pro Ser Arg Pro Val Gln Tyr Glu Gly Gly Gly
445                 450                 455                 460 gcc gac acc acg gcc acc gat att att tgc ccg atg tac gcg cgc gtg                  2884
Ala Asp Thr Thr Ala Thr Asp Ile Ile Cys Pro Met Tyr Ala Arg Val
                    465                 470                 475 gat gaa gac cag ccc ttc ccg gct gtg ccg aaa tgg tcc atc aaa aaa                  2932
Asp Glu Asp Gln Pro Phe Pro Ala Val Pro Lys Trp Ser Ile Lys Lys
                480                 485                 490 tgg ctt tcg cta cct gga gag acg cgc ccg ctg atc ctt tgc gaa tac                  2980
Trp Leu Ser Leu Pro Gly Glu Thr Arg Pro Leu Ile Leu Cys Glu Tyr
            495                 500                 505 gcc cac gcg atg ggt aac agt ctt ggc ggt ttc gct aaa tac tgg cag                  3028
Ala His Ala Met Gly Asn Ser Leu Gly Gly Phe Ala Lys Tyr Trp Gln
        510                 515                 520 gcg ttt cgt cag tat ccc cgt tta cag ggc ggc ttc gtc tgg gac tgg                  3076
Ala Phe Arg Gln Tyr Pro Arg Leu Gln Gly Gly Phe Val Trp Asp Trp
525                 530                 535                 540 gtg gat cag tcg ctg att aaa tat gat gaa aac ggc aac ccg tgg tcg                  3124
Val Asp Gln Ser Leu Ile Lys Tyr Asp Glu Asn Gly Asn Pro Trp Ser
                    545                 550                 555 gct tac ggc ggt gat ttt ggc gat acg ccg aac gat cgc cag ttc tgt                  3172
Ala Tyr Gly Gly Asp Phe Gly Asp Thr Pro Asn Asp Arg Gln Phe Cys
                560                 565                 570 atg aac ggt ctg gtc ttt gcc gac cgc acg ccg cat cca gcg ctg acg                  3220
Met Asn Gly Leu Val Phe Ala Asp Arg Thr Pro His Pro Ala Leu Thr
            575                 580                 585 gaa gca aaa cac cag cag cag ttt ttc cag ttc cgt tta tcc ggg caa                  3268
Glu Ala Lys His Gln Gln Gln Phe Phe Gln Phe Arg Leu Ser Gly Gln
        590                 595                 600 acc atc gaa gtg acc agc gaa tac ctg ttc cgt cat agc gat aac gag                  3316
Thr Ile Glu Val Thr Ser Glu Tyr Leu Phe Arg His Ser Asp Asn Glu
605                 610                 615                 620 ctc ctg cac tgg atg gtg gcg ctg gat ggt aag ccg ctg gca agc ggt                  3364
Leu Leu His Trp Met Val Ala Leu Asp Gly Lys Pro Leu Ala Ser Gly
                    625                 630                 635 gaa gtg cct ctg gat gtc gct cca caa ggt aaa cag ttg att gaa ctg                  3412
Glu Val Pro Leu Asp Val Ala Pro Gln Gly Lys Gln Leu Ile Glu Leu
                640                 645                 650 cct gaa cta ccg cag ccg gag agc gcc ggg caa ctc tgg ctc aca gta                  3460
Pro Glu Leu Pro Gln Pro Glu Ser Ala Gly Gln Leu Trp Leu Thr Val
            655                 660                 665 cgc gta gtg caa ccg aac gcg acc gca tgg tca gaa gcc ggg cac atc                  3508
Arg Val Val Gln Pro Asn Ala Thr Ala Trp Ser Glu Ala Gly His Ile
        670                 675                 680 agc gcc tgg cag cag tgg cgt ctg gcg gaa aac ctc agt gtg acg ctc                  3556
Ser Ala Trp Gln Gln Trp Arg Leu Ala Glu Asn Leu Ser Val Thr Leu
685                 690                 695                 700 ccc gcc gcg tcc cac gcc atc ccg cat ctg acc acc agc gaa atg gat                  3604
Pro Ala Ala Ser His Ala Ile Pro His Leu Thr Thr Ser Glu Met Asp
                    705                 710                 715 ttt tgc atc gag ctg ggt aat aag cgt tgg caa ttt aac cgc cag tca                  3652
Phe Cys Ile Glu Leu Gly Asn Lys Arg Trp Gln Phe Asn Arg Gln Ser
                720                 725                 730 ggc ttt ctt tca cag atg tgg att ggc gat aaa aaa caa ctg ctg acg                  3700
Gly Phe Leu Ser Gln Met Trp Ile Gly Asp Lys Lys Gln Leu Leu Thr
            735                 740                 745
```

```
                                               -continued ccg ctg cgc gat cag ttc acc cgt gca ccg ctg gat aac gac att ggc     3748
Pro Leu Arg Asp Gln Phe Thr Arg Ala Pro Leu Asp Asn Asp Ile Gly
    750                 755                 760 gta agt gaa gcg acc cgc att gac cct aac gcc tgg gtc gaa cgc tgg     3796
Val Ser Glu Ala Thr Arg Ile Asp Pro Asn Ala Trp Val Glu Arg Trp
765                 770                 775                 780 aag gcg gcg ggc cat tac cag gcc gaa gca gcg ttg ttg cag tgc acg     3844
Lys Ala Ala Gly His Tyr Gln Ala Glu Ala Ala Leu Leu Gln Cys Thr
                785                 790                 795 gca gat aca ctt gct gat gcg gtg ctg att acg acc gct cac gcg tgg     3892
Ala Asp Thr Leu Ala Asp Ala Val Leu Ile Thr Thr Ala His Ala Trp
    800                 805                 810 cag cat cag ggg aaa acc tta ttt atc agc cgg aaa acc tac cgg att     3940
Gln His Gln Gly Lys Thr Leu Phe Ile Ser Arg Lys Thr Tyr Arg Ile
815                 820                 825 gat ggt agt ggt caa atg gcg att acc gtt gat gtt gaa gtg gcg agc     3988
Asp Gly Ser Gly Gln Met Ala Ile Thr Val Asp Val Glu Val Ala Ser
    830                 835                 840 gat aca ccg cat ccg gcg cgg att ggc ctg aac tgc cag ctg gcg cag     4036
Asp Thr Pro His Pro Ala Arg Ile Gly Leu Asn Cys Gln Leu Ala Gln
845                 850                 855                 860 gta gca gag cgg gta aac tgg ctc gga tta ggg ccg caa gaa aac tat     4084
Val Ala Glu Arg Val Asn Trp Leu Gly Leu Gly Pro Gln Glu Asn Tyr
                865                 870                 875 ccc gac cgc ctt act gcc gcc tgt ttt gac cgc tgg gat ctg cca ttg     4132
Pro Asp Arg Leu Thr Ala Ala Cys Phe Asp Arg Trp Asp Leu Pro Leu
    880                 885                 890 tca gac atg tat acc ccg tac gtc ttc ccg agc gaa aac ggt ctg cgc     4180
Ser Asp Met Tyr Thr Pro Tyr Val Phe Pro Ser Glu Asn Gly Leu Arg
895                 900                 905 tgc ggg acg cgc gaa ttg aat tat ggc cca cac cag tgg cgc ggc gac     4228
Cys Gly Thr Arg Glu Leu Asn Tyr Gly Pro His Gln Trp Arg Gly Asp
                910                 915                 920 ttc cag ttc aac atc agc cgc tac agt caa cag caa ctg atg gaa acc     4276
Phe Gln Phe Asn Ile Ser Arg Tyr Ser Gln Gln Gln Leu Met Glu Thr
925                 930                 935                 940 agc cat cgc cat ctg ctg cac gcg gaa gaa ggc aca tgg ctg aat atc     4324
Ser His Arg His Leu Leu His Ala Glu Glu Gly Thr Trp Leu Asn Ile
                945                 950                 955 gac ggt ttc cat atg ggg att ggt ggc gac gac tcc tgg agc ccg tca     4372
Asp Gly Phe His Met Gly Ile Gly Gly Asp Asp Ser Trp Ser Pro Ser
    960                 965                 970 gta tcg gcg gaa ttc cag ctg agc gcc ggt cgc tac cat tac cag ttg     4420
Val Ser Ala Glu Phe Gln Leu Ser Ala Gly Arg Tyr His Tyr Gln Leu
975                 980                 985 gtc tgg tgt caa aaa aga tct gac tat aaa gat gag gac ctc gac cat     4468
Val Trp Cys Gln Lys Arg Ser Asp Tyr Lys Asp Glu Asp Leu Asp His
                990                 995                 1000 cat cat cat cat cac cgg taataatagg tagataagtg actgattaga            4516
His His His His His Arg
1005                1010 tgcattgatc cctcgaccaa ttccggttat tttccaccat attgccgtct tttggcaatg   4576
tgagggcccg gaaacctggc cctgtcttct tgacgagcat tcctagggt ctttcccctc   4636 tcgccaaagg aatgcaaggt ctgttgaatg tcgtgaagga agcagttcct ctggaagctt   4696
cttgaagaca aacaacgtct gtagcgaccc tttgcaggca gcggaacccc ccacctggcg   4756
acaggtgcct ctgcggccaa aagccacgtg tataagatac acctgcaaag gcggcacaac   4816
cccagtgcca cgttgtgagt tggatagttg tggaaagagt caaatggctc tcctcaagcg   4876
```

```
tattcaacaa gggctgaag gatgcccaga aggtacccca ttgtatggga tctgatctgg    4936
ggcctcggtg cacatgcttt acatgtgttt agtcgaggtt aaaaaacgtc taggccccc    4996 gaaccacggg gacgtggttt tcctttgaaa acacgatga taataccatg attgaacaag    5056
atggattgca cgcaggttct ccggccgctt gggtggagag gctattcgcc tatgactggg    5116
cacaacagac aatcggctgc tctgatgccg ccgtgttccg gctgtcagcg caggggcgcc    5176
cggttctttt tgtcaagacc gacctgtccg gtgccctgaa tgaactgcag gacgaggcag    5236
cgcggctatc gtggctggcc acgacgggcg ttccttgccg agctgtgctc gacgttgtca    5296
ctgaagcggg aagggactgg ctgctattgg gcgaagtgcc ggggcaggat ctcctgtcat    5356
ctcaccttgc tcctgccgag aaagtatcca tcatggctga tgcaatgcgg cggctgcata    5416
cgcttgatcc ggctacctgc ccattcgacc accaagcgaa acatcgcatc gagcgagcac    5476
gtactcggat ggaagccggt cttgtcgatc aggatgatct ggacgaagag catcaggggc    5536
tcgcgccagc cgaactgttc gccaggctca aggcgcgcat gcccgacggc gaggatctcg    5596
tcgtgaccca tggcgatgcc tgcttgccga atatcatggt ggaaaatggc cgcttttctg    5656
gattcatcga ctgtggccgg ctgggtgtgg cggaccgcta tcaggacata gcgttggcta    5716
cccgtgatat tgctgaagag cttggcggcg aatgggctga ccgcttcctc gtgctttacg    5776
gtatcgccgc tcccgattcg cagcgcatcg ccttctatcg ccttcttgac gagttcttct    5836
gagcgggact ctgggttcg catcgataaa ataaaagatt ttatttagtc tccagaaaaa    5896 gggggggaatg aaagacccca cctgtaggtt tggcaagcta gcttaagtaa cgccatttg    5956 caaggcatgg aaaatacat aactgagaat agagaagttc agatcaaggt caggaacaga    6016
tggaacagct gaatatgggc caaacaggat atctgtggta agcagttcct gccccggctc    6076
agggccaaga acagatggaa cagctgaata tgggccaaac aggatatctg tggtaagcag    6136
ttcctgcccc ggctcaggc caagaacaga tggtccccag atgcggtcca gccctcagca    6196
gtttctagag aaccatcaga tgtttccagg gtgccccaag gacctgaaat gaccctgtgc    6256
cttatttgaa ctaaccaatc agttcgcttc tcgcttctgt tcgcgcgctt ctgctccccg    6316
agctcaataa aagagcccac aacccctcac tcggggcgcc agtcctccga ttgactgagt    6376
cgcccgggta cccgtgtatc caataaaccc tcttgcagtt gcatccgact tgtggtctcg    6436
ctgttccttg ggagggtctc ctctgagtga ttgactaccc gtcagcgggg gtctttcatt    6496
catgcagcat gtatcaaaat taatttggtt ttttttctta agtatttaca ttaaatggcc    6556
atagttgcat taatgaatcg gccaacgcgc ggggagaggc ggtttgcgta ttggcgctct    6616
tccgcttcct cgctcactga ctcgctgcgc tcggtcgttc ggctgcggcg agcggtatca    6676
gctcactcaa aggcggtaat acgg                                         6700
```

```
<210> SEQ ID NO 2
<211> LENGTH: 1010
<212> TYPE: PRT
<213> ORGANISM: Artificial Sequence
<220> FEATURE:
<223> OTHER INFORMATION: Amino acid sequence for pICAST ALC

<400> SEQUENCE: 2

Met Gly Val Ile Thr Asp Ser Leu Ala Val Val Ala Arg Thr Asp Arg
  1               5                  10                  15

Pro Ser Gln Gln Leu Arg Ser Leu Asn Gly Glu Trp Arg Phe Ala Trp
             20                  25                  30
```

-continued

```
Phe Pro Ala Pro Glu Ala Val Pro Glu Ser Trp Leu Glu Cys Asp Leu
        35                  40                  45
Pro Glu Ala Asp Thr Val Val Pro Ser Asn Trp Gln Met His Gly
 50                  55                  60
Tyr Asp Ala Pro Ile Tyr Thr Asn Val Thr Tyr Pro Ile Thr Val Asn
 65                  70                  75                  80
Pro Pro Phe Val Pro Thr Glu Asn Pro Thr Gly Cys Tyr Ser Leu Thr
                 85                  90                  95
Phe Asn Val Asp Glu Ser Trp Leu Gln Glu Gly Gln Thr Arg Ile Ile
                100                 105                 110
Phe Asp Gly Val Asn Ser Ala Phe His Leu Trp Cys Asn Gly Arg Trp
                115                 120                 125
Val Gly Tyr Gly Gln Asp Ser Arg Leu Pro Ser Glu Phe Asp Leu Ser
        130                 135                 140
Ala Phe Leu Arg Ala Gly Glu Asn Arg Leu Ala Val Met Val Leu Arg
145                 150                 155                 160
Trp Ser Asp Gly Ser Tyr Leu Glu Asp Gln Asp Met Trp Arg Met Ser
                165                 170                 175
Gly Ile Phe Arg Asp Val Ser Leu Leu His Lys Pro Thr Thr Gln Ile
                180                 185                 190
Ser Asp Phe His Val Ala Thr Arg Phe Asn Asp Asp Phe Ser Arg Ala
        195                 200                 205
Val Leu Glu Ala Glu Val Gln Met Cys Gly Glu Leu Arg Asp Tyr Leu
        210                 215                 220
Arg Val Thr Val Ser Leu Trp Gln Gly Glu Thr Gln Val Ala Ser Gly
225                 230                 235                 240
Thr Ala Pro Phe Gly Gly Glu Ile Ile Asp Glu Arg Gly Gly Tyr Ala
                245                 250                 255
Asp Arg Val Thr Leu Arg Leu Asn Val Glu Asn Pro Lys Leu Trp Ser
                260                 265                 270
Ala Glu Ile Pro Asn Leu Tyr Arg Ala Val Val Glu Leu His Thr Ala
        275                 280                 285
Asp Gly Thr Leu Ile Glu Ala Glu Ala Cys Asp Val Gly Phe Arg Glu
        290                 295                 300
Val Arg Ile Glu Asn Gly Leu Leu Leu Leu Asn Gly Lys Pro Leu Leu
305                 310                 315                 320
Ile Arg Gly Val Asn Arg His Glu His His Pro Leu His Gly Gln Val
                325                 330                 335
Met Asp Glu Gln Thr Met Val Gln Asp Ile Leu Leu Met Lys Gln Asn
                340                 345                 350
Asn Phe Asn Ala Val Arg Cys Ser His Tyr Pro Asn His Pro Leu Trp
        355                 360                 365
Tyr Thr Leu Cys Asp Arg Tyr Gly Leu Tyr Val Val Asp Glu Ala Asn
        370                 375                 380
Ile Glu Thr His Gly Met Val Pro Met Asn Arg Leu Thr Asp Asp Pro
385                 390                 395                 400
Arg Trp Leu Pro Ala Met Ser Glu Arg Val Thr Arg Met Val Gln Arg
                405                 410                 415
Asp Arg Asn His Pro Ser Val Ile Ile Trp Ser Leu Gly Asn Glu Ser
                420                 425                 430
Gly His Gly Ala Asn His Asp Ala Leu Tyr Arg Trp Ile Lys Ser Val
        435                 440                 445
Asp Pro Ser Arg Pro Val Gln Tyr Glu Gly Gly Gly Ala Asp Thr Thr
```

-continued

```
            450                 455                 460
Ala Thr Asp Ile Ile Cys Pro Met Tyr Ala Arg Val Asp Glu Asp Gln
465                 470                 475                 480

Pro Phe Pro Ala Val Pro Lys Trp Ser Ile Lys Lys Trp Leu Ser Leu
                485                 490                 495

Pro Gly Glu Thr Arg Pro Leu Ile Leu Cys Glu Tyr Ala His Ala Met
                500                 505                 510

Gly Asn Ser Leu Gly Gly Phe Ala Lys Tyr Trp Gln Ala Phe Arg Gln
                515                 520                 525

Tyr Pro Arg Leu Gln Gly Phe Val Trp Asp Trp Val Asp Gln Ser
530                 535                 540

Leu Ile Lys Tyr Asp Glu Asn Gly Asn Pro Trp Ser Ala Tyr Gly Gly
545                 550                 555                 560

Asp Phe Gly Asp Thr Pro Asn Asp Arg Gln Phe Cys Met Asn Gly Leu
                565                 570                 575

Val Phe Ala Asp Arg Thr Pro His Pro Ala Leu Thr Glu Ala Lys His
                580                 585                 590

Gln Gln Gln Phe Phe Gln Phe Arg Leu Ser Gly Gln Thr Ile Glu Val
                595                 600                 605

Thr Ser Glu Tyr Leu Phe Arg His Ser Asp Asn Glu Leu Leu His Trp
                610                 615                 620

Met Val Ala Leu Asp Gly Lys Pro Leu Ala Ser Gly Glu Val Pro Leu
625                 630                 635                 640

Asp Val Ala Pro Gln Gly Lys Gln Leu Ile Glu Leu Pro Glu Leu Pro
                645                 650                 655

Gln Pro Glu Ser Ala Gly Gln Leu Trp Leu Thr Val Arg Val Val Gln
                660                 665                 670

Pro Asn Ala Thr Ala Trp Ser Glu Ala Gly His Ile Ser Ala Trp Gln
                675                 680                 685

Gln Trp Arg Leu Ala Glu Asn Leu Ser Val Thr Leu Pro Ala Ala Ser
                690                 695                 700

His Ala Ile Pro His Leu Thr Thr Ser Glu Met Asp Phe Cys Ile Glu
705                 710                 715                 720

Leu Gly Asn Lys Arg Trp Gln Phe Asn Arg Gln Ser Gly Phe Leu Ser
                725                 730                 735

Gln Met Trp Ile Gly Asp Lys Lys Gln Leu Leu Thr Pro Leu Arg Asp
                740                 745                 750

Gln Phe Thr Arg Ala Pro Leu Asp Asn Asp Ile Gly Val Ser Glu Ala
                755                 760                 765

Thr Arg Ile Asp Pro Asn Ala Trp Val Glu Arg Trp Lys Ala Ala Gly
770                 775                 780

His Tyr Gln Ala Glu Ala Ala Leu Leu Gln Cys Thr Ala Asp Thr Leu
785                 790                 795                 800

Ala Asp Ala Val Leu Ile Thr Thr Ala His Ala Trp Gln His Gln Gly
                805                 810                 815

Lys Thr Leu Phe Ile Ser Arg Lys Thr Tyr Arg Ile Asp Gly Ser Gly
                820                 825                 830

Gln Met Ala Ile Thr Val Asp Val Glu Val Ala Ser Asp Thr Pro His
                835                 840                 845

Pro Ala Arg Ile Gly Leu Asn Cys Gln Leu Ala Gln Val Ala Glu Arg
                850                 855                 860

Val Asn Trp Leu Gly Leu Gly Pro Gln Glu Asn Tyr Pro Asp Arg Leu
865                 870                 875                 880
```

```
Thr Ala Ala Cys Phe Asp Arg Trp Asp Leu Pro Leu Ser Asp Met Tyr
                885                 890                 895
Thr Pro Tyr Val Phe Pro Ser Glu Asn Gly Leu Arg Cys Gly Thr Arg
                900                 905                 910
Glu Leu Asn Tyr Gly Pro His Gln Trp Arg Gly Asp Phe Gln Phe Asn
                915                 920                 925
Ile Ser Arg Tyr Ser Gln Gln Leu Met Glu Thr Ser His Arg His
        930                 935                 940
Leu Leu His Ala Glu Glu Gly Thr Trp Leu Asn Ile Asp Gly Phe His
945                 950                 955                 960
Met Gly Ile Gly Gly Asp Asp Ser Trp Ser Pro Ser Val Ser Ala Glu
                965                 970                 975
Phe Gln Leu Ser Ala Gly Arg Tyr His Tyr Gln Leu Val Trp Cys Gln
                980                 985                 990
Lys Arg Ser Asp Tyr Lys Asp Glu Asp Leu Asp His His His His
                995                 1000                1005
His Arg
    1010

<210> SEQ ID NO 3
<211> LENGTH: 8518
<212> TYPE: DNA
<213> ORGANISM: Artificial Sequence
<220> FEATURE:
<223> OTHER INFORMATION: Nucleotide sequence for pICAST ALN

<400> SEQUENCE: 3
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca cccctcact cggggcgcca gtcctccgat tgactgagtc      360
gcccgggtac ccgtgtatcc aataaaccct cttgcagttg catccgactt gtggtctcgc     420
tgttccttgg gagggtctcc tctgagtgat tgactacccg tcagcggggg tctttcattt     480
ggggggctcgt ccgggatcgg gagacccctg cccaggacc accgaccac caccgggagg     540
caagctggcc agcaacttat ctgtgtctgt ccgattgtct agtgtctatg actgatttta     600
tgcgcctgcg tcggtactag ttagctaact agctctgtat ctggcggacc cgtggtggaa     660
ctgacgagtt ctgaacaccc ggccgcaacc ctggagacg tcccagggac tttgggggcc      720
gttttttgtgg cccgacctga ggaagggagt cgatgtggaa tccgaccccg tcaggatatg     780
tggttctggt aggagacgag aacctaaaac agttcccgcc tccgtctgaa ttttttgcttt    840
cggtttggaa ccgaagccgc gcgtcttgtc tgctgcagca tcgttctgtg ttgtctctgt     900
ctgactgtgt ttctgtattt gtctgaaaat tagggccaga ctgttaccac tcccttaagt     960
ttgaccttag gtaactggaa agatgtcgag cggctcgctc acaaccagtc ggtagatgtc    1020
aagaagagac gttgggttac cttctgctct gcagaatggc caacctttaa cgtcggatgg    1080
ccgcgagacg gcacctttaa ccgagacctc atcacccagg ttaagatcaa ggtcttttca    1140
cctggcccgc atggacaccc agaccaggtc cctacatcg tgacctggga agccttggct     1200
tttgaccccc ctccctgggt caagcccttt gtacacccta gcctccgcc tcctcttcct     1260
```

-continued

```
ccatccgccc cgtctctccc ccttgaacct cctcgttcga ccccgcctcg atcctccctt      1320
tatccagccc tcactccttc tctaggcgcc ggccgctcta gcccattaat acgactcact      1380 ataggggcgat tcgaacacca tgcaccatca tcatcatcac gtcgactata aagatgagga    1440
cctcgagatg ggcgtgatta cggattcact ggccgtcgtg gcccgcaccg atcgcccttc     1500
ccaacagtta cgcagcctga atggcgaatg cgctttgcc tggtttccgg caccagaagc      1560
ggtgccggaa agctggctgg agtgcgatct tcctgaggcc gatactgtcg tcgtcccctc    1620
aaactggcag atgcacggtt acgatgcgcc catctacacc aacgtgacct atcccattac     1680
ggtcaatccg ccgtttgttc ccacggagaa tccgacgggt tgttactcgc tcacatttaa    1740
tgttgatgaa agctggctac aggaaggcca gacgcgaatt atttttgatg gcgttaactc     1800
ggcgtttcat ctgtggtgca acgggcgctg gtcggttac ggccaggaca gtcgtttgcc     1860
gtctgaattt gacctgagcg cattttacg cgccggagaa aaccgcctcg cggtgatggt      1920
gctgcgctgg agtgacggca gttatctgga agatcaggat atgtggcgga tgagcggcat   1980
tttccgtgac gtctcgttgc tgcataaacc gactacacaa atcagcgatt tccatgttgc   2040
cactcgcttt aatgatgatt tcagccgcgc tgtactggag gctgaagttc agatgtgcgg   2100
cgagttgcgt gactacctac gggtaacagt ttctttatgg cagggtgaaa cgcaggtcgc    2160
cagcggcacc gcgccttcg gcggtgaaat tatcgatgag cgtggtggtt atgccgatcg    2220
cgtcacacta cgtctgaacg tcgaaaaccc gaaactgtgg agcgccgaaa tcccgaatct    2280
ctatcgtgcg gtggttgaac tgcacaccgc cgacggcacg ctgattgaag cagaagcctg   2340
cgatgtcggt ttccgcgagg tgcggattga aaatggtctg ctgctgctga acggcaagcc   2400
gttgctgatt cgaggcgtta accgtcacga gcatcatcct ctgcatggtc aggtcatgga    2460
tgagcagacg atggtgcagg atatcctgct gatgaagcag aacaacttta acgccgtgcg   2520
ctgttcgcat tatccgaacc atccgctgtg gtacacgctg tgcgaccgct acggcctgta    2580
tgtggtggat gaagccaata ttgaaaccca cggcatggtg ccaatgaatc gtctgaccga    2640
tgatccgcgc tggctaccgg cgatgagcga acgcgtaacg cgaatggtgc agcgcgatcg   2700
taatcacccg agtgtgatca tctggtcgct ggggaatgaa tcaggccacg gcctaatca    2760 cgacgcgctg tatcgctgga tcaaatctgt cgatccttcc cgcccggtgc agtatgaagg    2820
cggcggagcc gacaccacgg ccaccgatat tatttgcccg atgtacgcgc gcgtggatga   2880
agaccagccc ttcccggctg tgccgaaatg gtccatcaaa aaatggcttt cgctacctgg   2940
agagacgcgc ccgctgatcc tttgcgaata cgcccacgcg atgggtaaca gtcttggcgg   3000
tttcgctaaa tactgcgagg cgtttcgtca gtatccccgt ttacagggcg gcttcgtctg    3060
ggactgggtg gatcagtcgc tgattaaata tgatgaaaac ggcaacccgt ggtcggctta    3120
cggcggtgat tttggcgata cgccgaacga tcgccagttc tgtatgaacg gtctggtctt    3180
tgccgaccgc acgccgcatc cagcgctgac ggaagcaaaa caccagcagc agtttttcca     3240
gttccgttta tccgggcaaa ccatcgaagt gaccagcgaa tacctgttcc gtcatagcga    3300
taacgagctc ctgcactgga tggtggcgct ggatggtaag ccgctggcaa gcggtgaagt    3360
gcctctggat gtcgctccac aaggtaaaca gttgattgaa ctgcctgaac taccgcagcc    3420
ggagagcgcc gggcaactct ggctcacagt acgcgtagtg caaccgaacg cgaccgcatg    3480
gtcagaagcc gggcacatca gcgcctggca gcagtggcgt ctggcggaaa acctcagtgt    3540
gacgctcccc gccgcgtccc acgccatccc gcatctgacc accagcgaaa tggattttg     3600
```

```
catcgagctg ggtaataagc gttggcaatt taaccgccag tcaggctttc tttcacagat   3660
gtggattggc gataaaaaac aactgctgac gccgctgcgc gatcagttca cccgtgcacc   3720
gctggataac gacattggcg taagtgaagc gacccgcatt gaccctaacg cctgggtcga   3780
acgctggaag gcggcgggcc attaccaggc cgaagcagcg ttgttgcagt gcacggcaga   3840
tacacttgct gatgcggtgc tgattacgac cgctcacgcg tggcagcatc aggggaaaac   3900
cttatttatc agccggaaaa cctaccggat tgatggtagt ggtcaaatgg cgattaccgt   3960
tgatgttgaa gtggcgagcg ataccgcca tccggcgcgg attggcctga actgccagct   4020
ggcgcaggta gcagagcggg taaactggct cggattaggg ccgcaagaaa actatcccga   4080
ccgccttact gccgcctgtt ttgaccgctg ggatctgcca ttgtcagaca tgtataccc   4140 gtacgtcttc ccgagcgaaa acggtctgcg ctgcgggacg cgcgaattga attatggccc   4200
acaccagtgg cgcggcgact tccagttcaa catcagccgc tacagtcaac agcaactgat   4260
ggaaaccagc catcgccatc tgctgcacgc ggaagaaggc acatggctga atatcgacgg   4320
tttccatatg gggattggtg gcgacgactc ctggagcccg tcagtatcgg cggaattcca   4380
gctgagcgcc ggtcgctacc attaccagtt ggtctggtgt caaaaaagat ctggaggtgg   4440
tggcagcagg ccttggcgcg ccggatcctt aattaacaat tgaccggtaa taataggtag   4500
ataagtgact gattagatgc attgatccct cgaccaattc cggttatttt ccaccatatt   4560
gccgtctttt ggcaatgtga gggcccggaa acctggccct gtcttcttga cgagcattcc   4620 tagggggtctt tcccctctcg ccaaaggaat gcaaggtctg ttgaatgtcg tgaaggaagc   4680
agttcctctg gaagcttctt gaagacaaac aacgtctgta gcgaccctt gcaggcagcg   4740 gaaccccca cctggcgaca ggtgcctctg cggccaaaag ccacgtgtat aagatacacc   4800
tgcaaaggcg gcacaacccc agtgccacgt tgtgagttgg atagttgtgg aaagagtcaa   4860
atggctctcc tcaagcgtat tcaacaaggg gctgaaggat gcccagaagg tacccccattg   4920 tatgggatct gatctggggc ctcggtgcac atgctttaca tgtgtttagt cgaggttaaa   4980
aaacgtctag gccccccgaa ccacggggac gtggttttcc tttgaaaaac acgatgataa   5040
taccatgatt gaacaagatg gattgcacgc aggttctccg gccgcttggg tggagaggct   5100
attcggctat gactgggcac aacagacaat cggctgctct gatgccgccg tgttccggct   5160
gtcagcgcag gggcgcccgg ttcttttttgt caagaccgac ctgtccggtg ccctgaatga   5220
actgcaggac gaggcagcgc ggctatcgtg gctggccacg acgggcgttc cttgcgcagc   5280
tgtgctcgac gttgtcactg aagcgggaag ggactggctg ctattgggcg aagtgccggg   5340
gcaggatctc ctgtcatctc accttgctcc tgccgagaaa gtatccatca tggctgatgc   5400
aatgcggcgg ctgcatacgc ttgatccggc tacctgccca ttcgaccacc aagcgaaaca   5460
tcgcatcgag cgagcacgta ctcggatgga agccggtctt gtcgatcagg atgatctgga   5520
cgaagagcat caggggctcg cgccagccga actgttcgcc aggctcaagg cgcgcatgcc   5580
cgacggcgag gatctcgtcg tgacccatgg cgatgcctgc ttgccgaata tcatggtgga   5640
aaatggccgc ttttctggat tcatcgactg tggccggctg ggtgtggcgg accgctatca   5700
ggacatagcg ttggctaccc gtgatattgc tgaagagctt ggcggcgaat gggctgaccg   5760
cttcctcgtg ctttacggta tcgccgctcc cgattcgcag cgcatcgcct tctatcgcct   5820
tcttgacgag ttcttctgag cgggactctg gggttcgcat cgataaaata aaagatttta   5880
tttagtctcc agaaaagggg gggaatgaaa gaccccacct gtaggtttgg caagctagct   5940
taagtaacgc cattttgcaa ggcatggaaa atacataac tgagaataga aagttcaga   6000
```

```
tcaaggtcag gaacagatgg aacagctgaa tatgggccaa acaggatatc tgtggtaagc      6060
agttcctgcc ccggctcagg gccaagaaca gatggaacag ctgaatatgg gccaaacagg      6120
atatctgtgg taagcagttc ctgccccggc tcagggccaa gaacagatgg tccccagatg      6180
cggtccagcc ctcagcagtt tctagagaac catcagatgt tccagggtg ccccaaggac       6240 ctgaaatgac cctgtgcctt atttgaacta accaatcagt tcgcttctcg cttctgttcg      6300
cgcgcttctg ctccccgagc tcaataaaag agcccacaac ccctcactcg gggcgccagt      6360
cctccgattg actgagtcgc ccgggtaccc gtgtatccaa taaaccctct tgcagttgca      6420
tccgacttgt ggtctcgctg ttccttggga gggtctcctc tgagtgattg actacccgtc      6480
agcgggggtc tttcattcat gcagcatgta tcaaaattaa tttggttttt ttcttaagt       6540 atttacatta aatggccata gttgcattaa tgaatcggcc aacgcgcggg gagaggcggt      6600
ttgcgtattg gcgctcttcc gcttcctcgc tcactgactc gctgcgctcg gtcgttcggc      6660
tgcggcgagc ggtatcagct cactcaaagg cggtaatacg ttatccaca gaatcagggg      6720 ataacgcagg aaagaacatg tgagcaaaag gccagcaaaa ggccaggaac cgtaaaaagg      6780
ccgcgttgct ggcgtttttc cataggctcc gcccccctga cgagcatcac aaaaatcgac      6840
gctcaagtca gaggtggcga aacccgacag gactataaag ataccaggcg tttccccctg      6900
gaagctccct cgtgcgctct cctgttccga ccctgccgct taccggatac ctgtccgcct      6960
ttctcccttc gggaagcgtg gcgctttctc atagctcacg ctgtaggtat ctcagttcgg      7020
tgtaggtcgt tcgctccaag ctgggctgtg tgcacgaacc ccccgttcag cccgaccgct      7080
gcgccttatc cggtaactat cgtcttgagt ccaacccggt aagacacgac ttatcgccac      7140
tggcagcagc cactggtaac aggattagca gagcgaggta tgtaggcggt gctacagagt      7200
tcttgaagtg gtggcctaac tacggctaca ctagaagaac agtatttggt atctgcgctc      7260
tgctgaagcc agttaccttc ggaaaaagag ttggtagctc ttgatccggc aaacaaacca      7320
ccgctggtag cggtggtttt tttgtttgca agcagcagat tacgcgcaga aaaaaaggat      7380
ctcaagaaga tcctttgatc ttttctacgg ggtctgacgc tcagtggaac gaaaactcac      7440
gttaagggat tttggtcatg agattatcaa aaaggatctt cacctagatc cttttgcggc      7500
cgcaaatcaa tctaaagtat atatgagtaa acttggtctg acagttacca atgcttaatc      7560
agtgaggcac ctatctcagc gatctgtcta tttcgttcat ccatagttgc ctgactcccc      7620
gtcgtgtaga taactacgat acgggagggc ttaccatctg gccccagtgc tgcaatgata      7680
ccgcgagacc cacgctcacc ggctccagat ttatcagcaa taaaccagcc agccggaagg      7740
gccgagcgca gaagtggtcc tgcaacttta tccgcctcca tccagtctat taattgttgc      7800
cgggaagcta gagtaagtag ttcgccagtt aatagtttgc gcaacgttgt tgccattgct      7860
acaggcatcg tggtgtcacg ctcgtcgttt ggtatggctt cattcagctc cggttcccaa      7920
cgatcaaggc gagttacatg atccccatg ttgtgcaaaa aagcggttag ctccttcggt       7980
cctccgatcg ttgtcagaag taagttggcc gcagtgttat cactcatggt tatggcagca      8040
ctgcataatt ctcttactgt catgccatcc gtaagatgct tttctgtgac tggtgagtac      8100
tcaaccaagt cattctgaga atagtgtatg cggcgaccga gttgctcttg cccggcgtca      8160
atacgggata ataccgcgcc acatagcaga actttaaaag tgctcatcat ggaaaacgt       8220 tcttcggggc gaaaactctc aaggatctta ccgctgttga gatccagttc gatgtaaccc      8280
actcgtgcac ccaactgatc ttcagcatct tttactttca ccagcgtttc tgggtgagca      8340
```

-continued

```
aaaacaggaa ggcaaaatgc cgcaaaaaag ggaataaggg cgacacgaaa atgttgaata     8400
ctcatactct tcctttttca atattattga agcatttatc agggttattg tctcatgagc     8460
ggatacatat ttgaatgtat ttagaaaaat aaacaaatag gggttccgcg cacatttc      8518

<210> SEQ ID NO 4
<211> LENGTH: 8175
<212> TYPE: DNA
<213> ORGANISM: Artificial Sequence
<220> FEATURE:
<223> OTHER INFORMATION: Nucleotide sequence for pICAST OMC

<400> SEQUENCE: 4
ctgcagcctg aatatgggcc aaacaggata tctgtggtaa gcagttcctg ccccggctca       60
gggccaagaa cagatggaac agctgaatat gggccaaaca ggatatctgt ggtaagcagt      120
tcctgccccg gctcagggcc aagaacagat ggtccccaga tgcggtccag ccctcagcag      180
tttctagaga accatcagat gtttccaggg tgccccaagg acctgaaatg accctgtgcc      240
ttatttgaac taaccaatca gttcgcttct cgcttctgtt cgcgcgcttc tgctccccga      300
gctcaataaa agagcccaca acccctcact cggggcgcca gtcctccgat tgactgagtc      360
gcccgggtac ccgtgtatcc aataaaccct cttgcagttg catccgactt gtggtctcgc      420
tgttccttgg gagggtctcc tctgagtgat tgactacccg tcagcggggg tctttcattt      480
gggggctcgt ccgggatcgg agaccctg cccagggacc accgacccac caccgggagg       540
caagctggcc agcaacttat ctgtgtctgt ccgattgtct agtgtctatg actgatttta      600
tgcgcctgcg tcggtactag ttagctaact agctctgtat ctggcggacc cgtggtggaa      660
ctgacgagtt ctgaacaccc ggccgcaacc ctgggagacg tcccaggac tttgggggcc       720 gtttttgtgg cccgacctga ggaagggagt cgatgtggaa tccgaccccg tcaggatatg      780
tggttctggt aggagacgag aacctaaaac agttcccgcc tccgtctgaa ttttttgcttt     840 cggtttggaa ccgaagccgc gcgtcttgtc tgctgcagca tcgttctgtg ttgtctctgt      900
ctgactgtgt ttctgtattt gtctgaaaat tagggccaga ctgttaccac tcccttaagt      960
ttgaccttag gtaactggaa agatgtcgag cggctcgctc acaaccagtc ggtagatgtc     1020
aagaagagac gttgggttac cttctgctct gcagaatggc caacctttaa cgtcggatgg     1080
ccgcgagacg gcacctttaa ccgagacctc atcacccagg ttaagatcaa ggtcttttca     1140
cctggcccgc atggacaccc agaccaggtc cctacatcg tgacctggga agccttggct      1200
tttgaccccc ctccctgggt caagcccttt gtacacccta gcctccgcc tcctcttcct      1260 ccatccgccc cgtctctccc ccttgaacct cctcgttcga cccgcctcg atcctccctt      1320 tatccagccc tcactccttc tctaggcgcc ggccgctcta gccattaat acgactcact      1380 ataggggcgat tcgaatcagg ccttggcgcg ccggatcctt aattaagcgc aattgggagg    1440
tggcggtagc ctcgagatgg gcgtgattac ggattcactg gccgtcgttt tacaacgtcg     1500
tgactgggaa aaccctggcg ttacccaact taatcgcctt gcagcacatc cccctttcgc     1560
cagctggcgt aatagcgaag aggcccgcac cgatcgccct tcccaacagt tacgcagcct     1620
gaatggcgaa tggcgctttg cctggtttcc ggcaccagaa gcggtgccgg aaagctggct    1680
ggagtgcgat cttcctgagg ccgatactgt cgtcgtcccc tcaaactggc agatgcacgg    1740
ttacgatgcg cccatctaca ccaacgtgac ctatcccatt acggtcaatc cgccgtttgt    1800
tcccacggag aatccgacgg gttgttactc gctcacattt aatgttgatg aaagctggct    1860
acaggaaggc cagacgcgaa ttatttttga tggcgttaac tcggcgtttc atctgtggtg    1920
```

-continued

```
caacgggcgc tgggtcggtt acggccagga cagtcgtttg ccgtctgaat ttgacctgag    1980
cgcattttta cgcgccggag aaaaccgcct cgcggtgatg gtgctgcgct ggagtgacgg    2040
cagttatctg gaagatcagg atatgtggcg gatgagcggc attttccgtg acgtctcgtt    2100
gctgcataaa ccgactacac aaatcagcga tttccatgtt gccactcgct taatgatga    2160
tttcagccgc gctgtactgg aggctgaagt tcagatgtgc ggcgagttgc gtgactacct    2220
acgggtaaca gtttctttat ggcagggtga aacgcaggtc gccagcggca ccgcgccttt    2280
cggcggtgaa attatcgatg agcgtggtgg ttatgccgat cgcgtcacac tacgtctgaa    2340
cgtcgaaaac ccgaaactgt ggagcgccga atcccgaat ctctatcgtg cggtggttga    2400
actgcacacc gccgacggca cgctgattga agcagaagcc tgcgatgtcg gtttccgcga    2460
ggtgcggatt gaaaatggtc tgctgctgct gaacggcaag ccgttgctga ttcgaggcgt    2520
taaccgtcac gagcatcatc ctctgcatgg tcaggtcatg gatgagcaga cgatggtgca    2580
ggatatcctg ctgatgaagc agaacaactt taacgccgtg cgctgttcgc attatccgaa    2640
ccatccgctg tggtacacgc tgtgcgaccg ctacggcctg tatgtggtgg atgaagccaa    2700
tattgaaacc cacggcatgg tgccaatgaa tcgtctgacc gatgatccgc gctggctacc    2760
ggcgatgagc gaacgcgtaa cgcgaatggt gcagcgcgat cgtaatcacc cgagtgtgat    2820
catctggtcg ctggggaatg aatcaggcca cggcgctaat cacgacgcgc tgtatcgctg    2880
gatcaaatct gtcgatcctt cccgcccggt gcagtatgaa ggcggcggag ccgacaccac    2940
ggccaccgat attatttgcc cgatgtacgc gcgcgtggaa gagaccagc ccttcccggc    3000
tgtgccgaaa tggtccatca aaaaatggct ttcgctacct ggagagacgc gcccgctgat    3060
cctttgcgaa tacgcccacg cgatgggtaa cagtcttggc ggtttcgcta aatactggca    3120
ggcgtttcgt cagtatcccc gtttacaggg cggcttcgtc tgggactggg tggatcagtc    3180
gctgattaaa tatgatgaaa acggcaaccc gtggtcggct tacggcggtg attttggcga    3240
tacgccgaac gatcgccagt tctgtatgaa cggtctggtc tttgccgacc gcacgccgca    3300
tccagcgctg acggaagcaa acaccagca gcagttttc cagttccgtt tatccgggca    3360
aaccatcgaa gtgaccagcg aatacctgtt ccgtcatagc gataacgagc tcctgcactg    3420
gatggtggcg ctgatggta agccgctggc aagcggtgaa gtgcctctgg atgtcgctcc    3480
acaaggtaaa cagttgattg aactgcctga actaccgcag ccggagagcg ccgggcaact    3540
ctggctcaca gtacgcgtag tgcaaccgaa cgcgaccgca tggtcagaag ccgggcacat    3600
cagcgcctgg cagcagtggc gtctggcgga aaacctcagt gtgacgctcc ccgccgcgtc    3660
ccacgccatc ccgcatctga ccaccagcga aatggatttt tgcatcgagc tgggtaataa    3720
gcgttggcaa tttaaccgcc agtcaggctt tctttcacag atgtggattg cgataaaaa    3780
acaactgctg acgccgctgc gcgatcagtt caccgtgtc gatagatctg aacagaaact    3840
catttccgaa gaagacctag tcgaccatca tcatcatcat caccggtaat aataggtaga    3900
taagtgactg attagatgca tttcgactag atccctcgac caattccggt tattttccac    3960
catattgccg tcttttggca atgtgagggc ccggaaacct ggccctgtct tcttgacgag    4020
cattcctagg ggtctttccc ctctcgccaa aggaatgcaa ggtctgttga atgtcgtgaa    4080
ggaagcagtt cctctggaag cttcttgaag acaaacaacg tctgtagcga ccctttgcag    4140
gcagcggaac cccccacctg cgacaggtg cctctgcggc caaaagccac gtgtataaga    4200
tacacctgca aaggcggcac aaccccagtg ccacgttgtg agttggatag ttgtggaaag    4260
```

-continued

```
agtcaaatgg ctctcctcaa gcgtattcaa caaggggctg aaggatgccc agaaggtacc      4320
ccattgtatg ggatctgatc tggggcctcg gtgcacatgc tttacatgtg tttagtcgag      4380
gttaaaaaac gtctaggccc cccgaaccac ggggacgtgg ttttcctttg aaaaacacga      4440
tgataatacc atgaaaaagc ctgaactcac cgcgacgtct gtcgagaagt ttctgatcga      4500
aaagttcgac agcgtctccg acctgatgca gctctcggag ggcgaagaat ctcgtgcttt      4560
cagcttcgat gtaggagggc gtggatatgt cctgcgggta aatagctgcg ccgatggttt      4620
ctacaaagat cgttatgttt atcggcactt tgcatcggcc gcgctcccga ttccggaagt      4680
gcttgacatt ggggaattta gcgagagcct gacctattgc atctcccgcc gtgcacaggg      4740
tgtcacgttg caagacctgc ctgaaaccga actgcccgct gttctgcagc cggtcgcgga      4800
ggccatggat gcgatcgctg cggccgatct tagccagacg agcgggttcg cccattcgg       4860 accgcaagga atcggtcaat acactacatg gcgtgatttc atatgcgcga ttgctgatcc      4920
ccatgtgtat cactggcaaa ctgtgatgga cgacaccgtc agtgcgtccg tcgcgcaggc      4980
tctcgatgag ctgatgcttt gggccgagga ctgccccgaa gtccggcacc tcgtgcacgc      5040
ggatttcggc tccaacaatg tcctgacgga caatggccgc ataacagcgg tcattgactg      5100
gagcgaggcg atgttcgggg attcccaata cgaggtcgcc aacatcttct tctggaggcc      5160
gtggttggct tgtatggagc agcagacgcg ctacttcgag cggaggcatc cggagcttgc      5220
aggatcgccg cggctccggg cgtatatgct ccgcattggt cttgaccaac tctatcagag      5280
cttggttgac ggcaatttcg atgatgcagc ttgggcgcag gtcgatgcg acgcaatcgt       5340 ccgatccgga gccgggactg tcgggcgtac acaaatcgcc cgcagaagcg cggccgtctg      5400
gaccgatggc tgtgtagaag tactcgccga tagtggaaac cgacgcccca gcactcgtcc      5460
gagggcaaag gaatagagta gatgccgacc gggatctatc gataaaataa agatttat       5520 ttagtctcca gaaaagggg ggaatgaaag accccacctg taggtttggc aagctagctt       5580
aagtaacgcc attttgcaag gcatggaaaa atacataact gagaatagag aagttcagat      5640
caaggtcagg aacagatgga acagctgaat atgggccaaa caggatatct gtggtaagca      5700
gttcctgccc cggctcaggg ccaagaacag atggaacagc tgaatatggg ccaaacagga      5760
tatctgtggt aagcagttcc tgccccggct cagggcaag aacagatggt ccccagatgc       5820
ggtccagccc tcagcagttt ctagagaacc atcagatgtt tccagggtgc cccaaggacc      5880
tgaaatgacc ctgtgcctta tttgaactaa ccaatcagtt cgcttctcgc ttctgttcgc      5940
gcgcttctgc tccccgagct caataaaaga gcccacaacc cctcactcgg ggcgccagtc      6000
ctccgattga ctgagtcgcc cgggtacccg tgtatccaat aaaccctctt gcagttgcat      6060
ccgacttgtg gtctcgctgt tccttgggag ggtctcctct gagtgattga ctacccgtca      6120 gcggggtct ttcattcatg cagcatgtat caaaattaat ttggtttttt tcttaagta       6180 tttacattaa atggccatag ttgcattaat gaatcggcca acgcgcgggg agaggcggtt      6240
tgcgtattgg cgctcttccg cttcctcgct cactgactcg ctgcgctcgg tcgttcggct      6300
gcggcgagcg gtatcagctc actcaaaggc ggtaatacgg ttatccacag aatcaggga       6360 taacgcagga agaacatgt gagcaaaagg ccagcaaaag gccaggaacc gtaaaaaggc       6420
cgcgttgctg gcgtttttcc ataggctccg ccccctgac gagcatcaca aaaatcgacg       6480
ctcaagtcag aggtggcgaa acccgacagg actataaaga taccaggcgt ttccccctgg      6540
aagctccctc gtgcgctctc ctgttccgac cctgccgctt accggatacc tgtccgcctt      6600
tctcccttcg ggaagcgtgg cgctttctca tagctcacgc tgtaggtatc tcagttcggt      6660
```

```
gtaggtcgtt cgctccaagc tgggctgtgt gcacgaaccc cccgttcagc ccgaccgctg    6720
cgccttatcc ggtaactatc gtcttgagtc caacccggta agacacgact tatcgccact    6780
ggcagcagcc actggtaaca ggattagcag agcgaggtat gtaggcggtg ctacagagtt    6840
cttgaagtgg tggcctaact acggctacac tagaagaaca gtatttggta tctgcgctct    6900
gctgaagcca gttaccttcg gaaaaagagt tggtagctct tgatccggca acaaaccac     6960 cgctggtagc ggtggttttt tgtttgcaa  gcagcagatt acgcgcagaa aaaaggatc     7020 tcaagaagat cctttgatct tttctacggg gtctgacgct cagtggaacg aaaactcacg    7080
ttaagggatt ttggtcatga gattatcaaa aaggatcttc acctagatcc ttttaaatta    7140
aaaatgaagt ttgcggccgc aaatcaatct aaagtatata tgagtaaact tggtctgaca    7200
gttaccaatg cttaatcagt gaggcaccta tctcagcgat ctgtctattt cgttcatcca    7260
tagttgcctg actccccgtc gtgtagataa ctacgatacg ggagggctta ccatctggcc    7320
ccagtgctgc aatgataccg cgagacccac gctcaccggc tccagattta tcagcaataa    7380
accagccagc cggaagggcc gagcgcagaa gtggtcctgc aactttatcc gcctccatcc    7440
agtctattaa ttgttgccgg gaagctagag taagtagttc gccagttaat agtttgcgca    7500
acgttgttgc cattgctaca ggcatcgtgg tgtcacgctc gtcgtttggt atggcttcat    7560
tcagctccgg ttcccaacga tcaaggcgag ttacatgatc ccccatgttg tgcaaaaaag    7620
cggttagctc cttcggtcct ccgatcgttg tcagaagtaa gttggccgca gtgttatcac    7680
tcatggttat ggcagcactg cataattctc ttactgtcat gccatccgta agatgctttt    7740
ctgtgactgg tgagtactca accaagtcat tctgagaata gtgtatgcgg cgaccgagtt    7800
gctcttgccc ggcgtcaata cgggataata ccgcgccaca tagcagaact ttaaaagtgc    7860
tcatcattgg aaaacgttct cggggcgaaa actctcaag  gatcttaccg ctgttgagat    7920
ccagttcgat gtaacccact cgtgcaccca actgatcttc agcatctttt actttcacca    7980
gcgtttctgg gtgagcaaaa acaggaaggc aaaatgccgc aaaaaaggga taagggcga    8040 cacggaaatg ttgaatactc atactcttcc ttttcaata  ttattgaagc atttatcagg    8100
gttattgtct catgagcgga tacatatttg aatgtattta gaaaaataaa caaataggg    8160 ttccgcgcac atttc                                                    8175
```

<210> SEQ ID NO 5
<211> LENGTH: 8175
<212> TYPE: DNA
<213> ORGANISM: Artificial Sequence
<220> FEATURE:
<223> OTHER INFORMATION: Nucleotide sequence for pICAST OMN

<400> SEQUENCE: 5

```
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag    180
tttctagaga accatcagat gtttccaggg tgccccaagg acctgaaatg accctgtgcc    240
ttatttgaac taaccaatca gttcgcttct cgcttctgtt cgcgcgcttc tgctccccga    300
gctcaataaa agagcccaca acccctcact cggggcgcca gtcctccgat tgactgagtc    360
gcccgggtac ccgtgtatcc aataaaccct cttgcagttg catccgactt gtggtctcgc    420
tgttccttgg gagggtctcc tctgagtgat tgactacccg tcagcggggg tctttcattt    480
```

-continued

```
gggggctcgt ccgggatcgg gagacccctg cccagggacc accgacccac caccgggagg    540
caagctggcc agcaacttat ctgtgtctgt ccgattgtct agtgtctatg actgatttta    600
tgcgcctgcg tcggtactag ttagctaact agctctgtat ctggcggacc cgtggtggaa    660
ctgacgagtt ctgaacaccc ggccgcaacc ctgggagacg tcccagggac tttggggcc     720 gttttttgtgg cccgacctga ggaagggagt cgatgtggaa tccgaccccg tcaggatatg    780
tggttctggt aggagacgag aacctaaaac agttcccgcc tccgtctgaa tttttgcttt    840
cggtttggaa ccgaagccgc gcgtcttgtc tgctgcagca tcgttctgtg ttgtctctgt    900
ctgactgtgt ttctgtatttt gtctgaaaat tagggccaga ctgttaccac tcccttaagt    960
ttgaccttag gtaactggaa agatgtcgag cggctcgctc acaaccagtc ggtagatgtc   1020
aagaagagac gttgggttac cttctgctct gcagaatggc caacctttaa cgtcggatgg   1080
ccgcgagacg gcacctttaa ccgagacctc atcacccagg ttaagatcaa ggtcttttca   1140
cctggcccga atggacaccc agaccaggtc ccctacatcg tgacctggga agccttggct   1200 tttgacccccc ctccctgggt caagcccttt gtacacccta agcctccgcc tcctcttcct   1260
ccatccgccc cgtctctccc ccttgaacct cctcgttcga cccgcctcg atcctccctt    1320 tatccagccc tcactccttc tctaggcgcc ggccgctcta gcccattaat acgactcact   1380 ataggggcgat tcgaatcagg ccttggcgcg ccggatcctt aattaagcgc aattgggagg   1440
tggcggtagc ctcgagatgg gcgtgattac ggattcactg gccgtcgttt tacaacgtcg   1500
tgactgggaa aaccctggcg ttacccaact taatcgcctt gcagcacatc ccccttttcgc   1560 cagctggcgt aatagcgaag aggcccgcac cgatcgccct tcccaacagt tacgcagcct   1620
gaatggcgaa tggcgctttg cctggttttcc ggcaccagaa gcggtgccgg aaagctggct   1680
ggagtgcgat cttcctgagg ccgatactgt cgtcgtcccc tcaaactggc agatgcacgg   1740
ttacgatgcg cccatctaca ccaacgtgac ctatcccatt acggtcaatc cgccgttttgt   1800 tcccacggag aatccgacgg gttgttactc gctcacattt aatgttgatg aaagctggct   1860
acaggaaggc cagacgcgaa ttatttttga tggcgttaac tcggcgtttc atctgtggtg   1920
caacgggcgc tgggtcggtt acggccagga cagtcgtttg ccgtctgaat tgacctgag   1980 cgcattttta cgcgccggag aaaaccgcct cgcggtgatg gtgctgcgct ggagtgacgg   2040
cagttatctg gaagatcagg atatgtggcg gatgagcggc attttccgtg acgtctcgtt   2100
gctgcataaa ccgactacac aaatcagcga tttccatgtt gccactcgct ttaatgatga   2160
tttcagccgc gctgtactgg aggctgaagt tcagatgtgc ggcgagttgc gtgactacct   2220
acgggtaaca gtttctttat ggcagggtga acgcaggtc gccagcggca ccgcgccttt   2280
cggcggtgaa attatcgatg agcgtggtgg ttatgccgat cgcgtcacac tacgtctgaa   2340
cgtcgaaaac ccgaaactgt ggagcgccga atcccgaat ctctatcgtg cggtggttga   2400
actgcacacc gccgacggca cgctgattga agcagaagcc tgcgatgtcg gtttccgcga   2460
ggtgcggatt gaaaatggtc tgctgctgct gaacggcaag ccgttgctga ttcgaggcgt   2520
taaccgtcac gagcatcatc ctctgcatgg tcaggtcatg gatgagcaga cgatggtgca   2580
ggatatcctg ctgatgaagc agaacaactt taacgccgtg cgctgttcgc attatccgaa   2640
ccatccgctg tggtacacgc tgtgcgaccg ctacggcctg tatgtggtgg atgaagccaa   2700
tattgaaacc cacggcatgg tgccaatgaa tcgtctgacc gatgatccgc gctggctacc   2760
ggcgatgagc gaacgcgtaa cgcgaatggt gcagcgcgat cgtaatcacc cgagtgtgat   2820
catctggtcg ctggggaatg aatcaggcca cggcgctaat cacgacgcgc tgtatcgctg   2880
```

```
gatcaaatct gtcgatcctt cccgcccggt gcagtatgaa ggcggcggag ccgacaccac   2940
ggccaccgat attatttgcc cgatgtacgc gcgcgtggat gaagaccagc ccttcccggc   3000
tgtgccgaaa tggtccatca aaaaatggct ttcgctacct ggagagacgc gcccgctgat   3060
cctttgcgaa tacgcccacg cgatgggtaa cagtcttggc ggtttcgcta aatactggca   3120
ggcgtttcgt cagtatcccc gtttacaggg cggcttcgtc tgggactggg tggatcagtc   3180
gctgattaaa tatgatgaaa acggcaaccc gtggtcggct tacggcggtg attttggcga   3240
tacgccgaac gatcgccagt tctgtatgaa cggtctggtc tttgccgacc gcacgccgca   3300
tccagcgctg acggaagcaa acaccagca gcagttttc cagttccgtt tatccgggca    3360
aaccatcgaa gtgaccagcg aatacctgtt ccgtcatagc gataacgagc tcctgcactg   3420
gatggtggcg ctggatggta agccgctggc aagcggtgaa gtgcctctgg atgtcgctcc   3480
acaaggtaaa cagttgattg aactgcctga actaccgcag ccggagagcg ccgggcaact   3540
ctggctcaca gtacgcgtag tgcaaccgaa cgcgaccgca tggtcagaag ccgggcacat   3600
cagcgcctgg cagcagtggc gtctggcgga aaacctcagt gtgacgctcc ccgccgcgtc   3660
ccacgccatc ccgcatctga ccaccagcga aatggatttt tgcatcgagc tgggtaataa   3720
gcgttggcaa tttaaccgcc agtcaggctt tctttcacag atgtggattg cgataaaaa    3780 acaactgctg acgccgctgc gcgatcagtt caccgtgtc gatagatctg aacagaaact    3840
catttccgaa gaagacctag tcgaccatca tcatcatcat caccggtaat aataggtaga   3900
taagtgactg attagatgca tttcgactag atccctcgac caattccggt tattttccac   3960
catattgccg tcttttggca atgtgagggc ccggaaacct ggccctgtct tcttgacgag   4020
cattcctagg ggtcttttccc ctctcgccaa aggaatgcaa ggtctgttga atgtcgtgaa   4080
ggaagcagtt cctctggaag cttcttgaag acaaacaacg tctgtagcga cccttttgcag  4140 gcagcggaac cccccacctg cgacaggtg cctctgcggc caaaagccac gtgtataaga    4200
tacacctgca aggcggcac aaccccagtg ccacgttgtg agttggatag ttgtggaaag    4260
agtcaaatgg ctctcctcaa gcgtattcaa caaggggctg aaggatgccc agaaggtacc   4320
ccattgtatg ggatctgatc tggggcctcg gtgcacatgc tttacatgtg tttagtcgag   4380
gttaaaaaac gtctaggccc cccgaaccac ggggacgtgg ttttcctttg aaaaacacga   4440
tgataatacc atgaaaaagc ctgaactcac cgcgacgtct gtcgagaagt ttctgatcga   4500
aaagttcgac agcgtctccg acctgatgca gctctcggag ggcgaagaat ctcgtgcttt   4560
cagcttcgat gtaggagggc gtggatatgt cctgcgggta aatagctgcg ccgatggttt   4620
ctacaaagat cgttatgttt atcggcactt tgcatcggcc gcgctcccga ttccggaagt   4680
gcttgacatt ggggaattta gcgagagcct gacctattgc atctcccgcc gtgcacaggg   4740
tgtcacgttg caagacctgc ctgaaaccga actgcccgct gttctgcagc cggtcgcgga   4800
ggccatggat gcgatcgctg cggccgatct tagccagacg agcgggttcg cccattcgg    4860 accgcaagga atcggtcaat acactacatg gcgtgatttc atatgcgcga ttgctgatcc   4920
ccatgtgtat cactggcaaa ctgtgatgga cgacaccgtc agtgcgtccg tcgcgcaggc   4980
tctcgatgag ctgatgcttt gggccgagga ctgccccgaa gtccggcacc tcgtgcacgc   5040
ggatttcggc tccaacaatg tcctgacgga caatggccgc ataacagcgg tcattgactg   5100
gagcgaggcg atgttcgggg attcccaata cgaggtcgcc aacatcttct tctggaggcc   5160
gtggttggct tgtatggagc agcagacgcg ctacttcgag cggaggcatc cggagcttgc   5220
```

```
aggatcgccg cggctccggg cgtatatgct ccgcattggt cttgaccaac tctatcagag    5280
cttggttgac ggcaatttcg atgatgcagc ttgggcgcag ggtcgatgcg acgcaatcgt    5340
ccgatccgga gccgggactg tcgggcgtac acaaatcgcc cgcagaagcg cggccgtctg    5400
gaccgatggc tgtgtagaag tactcgccga tagtggaaac cgacgcccca gcactcgtcc    5460
gagggcaaag gaatagagta gatgccgacc gggatctatc gataaaataa aagattttat    5520
ttagtctcca gaaaaggggg ggaatgaaag accccacctg taggtttggc aagctagctt    5580
aagtaacgcc attttgcaag gcatggaaaa atacataact gagaatagag aagttcagat    5640
caaggtcagg aacagatgga acagctgaat atgggccaaa caggatatct gtggtaagca    5700
gttcctgccc cggctcaggg ccaagaacag atggaacagc tgaatatggg ccaaacagga    5760
tatctgtggt aagcagttcc tgccccggct caggccaag aacagatggt ccccagatgc    5820
ggtccagccc tcagcagttt ctagagaacc atcagatgtt tccagggtgc cccaaggacc    5880
tgaaatgacc ctgtgcctta tttgaactaa ccaatcagtt cgcttctcgc ttctgttcgc    5940
gcgcttctgc tccccgagct caataaaaga gcccacaacc cctcactcgg ggcgccagtc    6000
ctccgattga ctgagtcgcc cgggtacccg tgtatccaat aaaccctctt gcagttgcat    6060
ccgacttgtg gtctcgctgt tccttgggag ggtctcctct gagtgattga ctacccgtca    6120
gcggggtct ttcattcatg cagcatgtat caaaattaat ttggttttt tcttaagta     6180
tttacattaa atggccatag ttgcattaat gaatcggcca acgcgcgggg agaggcggtt    6240
tgcgtattgg cgctcttccg cttcctcgct cactgactcg ctgcgctcgg tcgttcggct    6300
gcggcgagcg gtatcagctc actcaaaggc ggtaatacgg ttatccacag aatcagggga    6360
taacgcagga agaacatgt gagcaaaagg ccagcaaaag gccaggaacc gtaaaaaggc    6420
cgcgttgctg gcgttttttcc ataggctccg ccccctgac gagcatcaca aaaatcgacg    6480
ctcaagtcag aggtggcgaa acccgacagg actataaaga taccaggcgt ttccccctgg    6540
aagctccctc gtgcgctctc ctgttccgac cctgccgctt accggatacc tgtccgcctt    6600
tctcccttcg ggaagcgtgg cgctttctca tagctcacgc tgtaggtatc tcagttcggt    6660
gtaggtcgtt cgctccaagc tgggctgtgt gcacgaaccc cccgttcagc ccgaccgctg    6720
cgccttatcc ggtaactatc gtcttgagtc caacccggta agacacgact tatcgccact    6780
ggcagcagcc actggtaaca ggattagcag agcgaggtat gtaggcggtg ctacagagtt    6840
cttgaagtgg tggcctaact acggctacac tagaagaaca gtatttggta tctgcgctct    6900
gctgaagcca gttaccttcg gaaaaagagt tggtagctct tgatccggca acaaaccac     6960
cgctggtagc ggtggttttt tgtttgcaa gcagcagatt acgcgcagaa aaaaggatc     7020
tcaagaagat cctttgatct tttctacggg gtctgacgct cagtggaacg aaaactcacg    7080
ttaagggatt ttggtcatga gattatcaaa aaggatcttc acctagatcc ttttaaatta    7140
aaaatgaagt ttgcggccgc aaatcaatct aaagtatata tgagtaaact tggtctgaca    7200
gttaccaatg cttaatcagt gaggcaccta tctcagcgat ctgtctattt cgttcatcca    7260
tagttgcctg actccccgtc gtgtagataa ctacgatacg ggagggctta ccatctggcc    7320
ccagtgctgc aatgataccg cgagacccac gctcaccggc tccagattta tcagcaataa    7380
accagccagc cggaagggcc gagcgcagaa gtggtcctgc aactttatcc gcctccatcc    7440
agtctattaa ttgttgccgg gaagctagag taagtagttc gccagttaat agtttgcgca    7500
acgttgttgc cattgctaca ggcatcgtgg tgtcacgctc gtcgtttggt atggcttcat    7560
tcagctccgg ttcccaacga tcaaggcgag ttacatgatc ccccatgttg tgcaaaaaag    7620
```

```
cggttagctc cttcggtcct ccgatcgttg tcagaagtaa gttggccgca gtgttatcac    7680
tcatggttat ggcagcactg cataattctc ttactgtcat gccatccgta agatgctttt    7740
ctgtgactgg tgagtactca accaagtcat tctgagaata gtgtatgcgg cgaccgagtt    7800
gctcttgccc ggcgtcaata cgggataata ccgcgccaca tagcagaact ttaaaagtgc    7860
tcatcattgg aaaacgttct tcggggcgaa aactctcaag gatcttaccg ctgttgagat    7920
ccagttcgat gtaacccact cgtgcaccca actgatcttc agcatctttt actttcacca    7980
gcgtttctgg gtgagcaaaa acaggaaggc aaaatgccgc aaaaaaggga ataagggcga    8040
cacggaaatg ttgaatactc atactcttcc tttttcaata ttattgaagc atttatcagg  8100
gttattgtct catgagcgga tacatatttg aatgtattta gaaaaataaa caaatagggg  8160
ttccgcgcac atttc                                                   8175
```

<210> SEQ ID NO 6
<211> LENGTH: 5
<212> TYPE: PRT
<213> ORGANISM: Artificial Sequence
<220> FEATURE:
<223> OTHER INFORMATION: GS Linker

<400> SEQUENCE: 6

Gly Gly Gly Gly Ser
 1               5

What is claimed is:

1. A method of assessing the effect of a test condition on G-protein-coupled receptor (GPCR) pathway activity, comprising:
   a) providing a cell that expresses a GPCR as a fusion protein to a first mutant form of a reporter enzyme and an interacting protein partner as a fusion protein to a second mutant form of the reporter enzyme;
   b) exposing the cell to a ligand for said GPCR under said test condition; and
   c) detecting enzymatic activity of the reporter enzyme;
   wherein increased reporter enzyme activity in the cell compared to that which occurs in the absence of said test condition indicates increased GPCR interaction with its interacting protein partner compared to that which occurs in the absence of said test condition, and decreased reporter enzyme activity in the cell compared to that which occurs in the absence of said test condition indicates decreased GPCR interaction with its interacting protein partner compared to that which occurs in the absence of said test condition;
   wherein the protein partner is an arrestin and wherein the GPCR and the first mutant form of reporter enzyme are linked together by a polypeptide linker represented by the formula -(GGGGS)$_n$-(SEQ ID NO:6).

2. A method according to claim 1, wherein the test condition is the presence in the cell of a kinase.

3. A method according to claim 1, wherein the test condition is the presence in the cell of a G-protein.

4. A method according to claim 1, wherein the test condition is the exposure of the cell to a compound selected from GPCR agonists and GPCR antagonists.

5. A method according to claim 1, wherein the test condition is co-expression in the cell of a second receptor.

6. A method according to claim 5, wherein the second receptor is a GPCR receptor.

7. A method according to claim 5, wherein homo-dimerization of GPCR is determined.

8. A method according to claim 5, wherein hetero-dimerization of GPCR is determined.

9. The method of claim 1, wherein n is 2 or more.

10. The method of claim 1, wherein n is 4.

11. The method of claim 1, wherein the second mutant form of the reporter enzyme is linked to the C-terminal of the arrestin protein.

12. A method for screening a β-arrestin protein for the ability to bind to activated GPCRs, comprising:
   a) providing a cell that:
      i) expresses at least one GPCR as a fusion protein to a first mutant form of a reporter enzyme; and
      ii) contains a conjugate comprising a test β-arrestin protein as a fusion protein with a second mutant form of the reporter enzyme;
   b) exposing the cell to a ligand for said at least one GPCR; and
   c) detecting enzymatic activity of the reporter enzyme;
   wherein an increase in enzymatic activity in the cell indicates β-arrestin protein binding to the activated GPCR;
   wherein the GPCR and the first mutant form of reporter enzyme are linked together by a polypeptide linker represented by the formula -(GGGGS)$_n$-(SEQ ID NO:6).

13. The method of claim 12, wherein n is 2 or more.

14. The method of claim 12, wherein n is 4.

15. The method of claim 12, wherein the second mutant form of the reporter enzyme is linked to the C-terminal of the arrestin protein.

16. The method of claim 12, wherein the β-arrestin protein is an unidentified β-arrestin, a β-arrestin fragment or a mutant form of a β-arrestin protein.

17. A method for screening a test compound for G-protein-coupled receptor (GPCR) agonist activity, comprising:
   a) providing a cell that expresses a GPCR as a fusion protein to a first mutant form of a reporter enzyme and an arrestin protein as a fusion protein to a second mutant form of the reporter enzyme;
   b) exposing the cell to a test compound; and
   c) detecting enzymatic activity of the reporter enzyme;
   wherein increased reporter enzyme activity after exposure of the cell to the test compound indicates GPCR agonist activity of the test compound;
   wherein the GPCR and the first mutant form of reporter enzyme are linked together by a polypeptide linker represented by the formula -(GGGGS)$_n$-(SEQ ID NO:6).

18. A method according to claim 17, wherein the cell expresses a GPCR whose function is known.

19. A method according to claim 17, wherein the cell expresses a GPCR whose function is unknown.

20. A method according to claim 17, wherein the cell expresses an odorant or taste GPCR.

21. A method according to claim 17, wherein the cell expresses a β-adrenergic receptor.

22. A method according to claim 17, wherein the cell is selected from the group consisting of mammalian cells, cells of invertebrate origin, plant cells and protozoa cells.

23. A method according to claim 17, wherein the cell endogenously expresses a GPCR.

24. A method according to claim 17, wherein the cell has been transformed to express a GPCR not endogenously expressed by such a cell.

25. The method of claim 17, wherein the cell endogenously expresses multiple G-protein-coupled receptors.

26. The method of claim 17, wherein n is 2 or more.

27. The method of claim 17, wherein n is 4.

28. The method of claim 17, wherein the second mutant form of the reporter enzyme is linked to the C-terminal of the arrestin protein.

29. A method of screening a test compound for G-protein-coupled receptor (GPCR) antagonist activity, comprising:
   a) providing a cell that expresses a GPCR as a fusion protein to a first mutant form of a reporter enzyme and an arrestin protein as a fusion protein to a second mutant form of the reporter enzyme;
   b) exposing the cell to said test compound;
   c) exposing the cell to an agonist for said GPCR; and
   d) detecting complementation of said reporter enzyme;
   where exposure to the agonist occurs at the same time as, or subsequent to, exposure to the test compound, and wherein decreased reporter enzyme activity after exposure of the cell to the test compound indicates that the test compound is an antagonist for said GPCR;
   wherein the GPCR and the first mutant form of reporter enzyme are linked together by a polypeptide linker represented by the formula -(GGGGS)$_n$-(SEQ ID NO:6).

30. The method of claim 29, wherein n is 2 or more.

31. The method of claim 29, wherein n is 4.

32. The method of claim 29, wherein the second mutant form of the reporter enzyme is linked to the C-terminal of the arrestin protein.

33. A method of screening a plurality of cells for those cells which contain a G-protein-coupled receptor (GPCR) responsive to a GPCR ligand, the method comprising:
   a) providing a plurality of cells that express the GPCR as a fusion protein to a first mutant form of reporter enzyme and a binding partner of the GPCR as a fusion protein to a second mutant form of the enzyme complementary to the first mutant form of the enzyme;
   b) exposing the cells to a GPCR ligand; and
   c) detecting enzymatic activity of the reporter enzyme;
   wherein an increase or decrease in enzymatic activity after exposure of the cell to the GPCR ligand indicates that the cell contains a GPCR responsive to the ligand;
   wherein the binding partner is an arrestin and;
   wherein the GPCR and the first mutant form of reporter enzyme are linked together by a polypeptide linker represented by the formula -(GGGGS)$_n$-(SEQ ID NO:6).

34. A method according to claim 33, wherein the plurality of cells are contained in a tissue.

35. A method according to claim 33, wherein the plurality of cells are contained in an organ.

36. A method according to claim 33, wherein step (b) comprises exposing the cells to a plurality of GPCR agonists or ligand libraries.

37. The method of claim 33, wherein enzyme activity is detected in a mixture of the plurality of cells.

38. The method of claim 33, further comprising isolating clones of individual cells, wherein enzyme activity is detected in the clones of individual cells.

39. The method of claim 33, wherein the binding partner is a cellular component that directly or indirectly modulates GPCR activation or inactivation.

40. The method of claim 33, wherein the plurality of cells express multiple GPCRs, each as a fusion protein to the first mutant form of reporter enzyme.

41. The method of claim 33, wherein the GPCR and the binding partner interact as a result of the ligand binding to the GPCR.

42. The method of claim 33, wherein n is 2 or more.

43. The method of claim 33, wherein n is 4.

44. The method of claim 33, wherein the second mutant form of the reporter enzyme is linked to the C-terminal of the arrestin protein.

45. A substrate having deposited thereon a plurality of cells, said cells expressing at least one GPCR as a fusion protein to a first mutant form of reporter enzyme and an arrestin protein as a fusion to a second mutant form of the reporter enzyme wherein the GPCR and the first mutant form of reporter enzyme are linked together by a polypeptide linker represented by the formula -(GGGGS)$_n$-(SEQ ID NO:6).

46. A substrate according to claim 45, wherein the substrate contains an enzyme-labile chemical group which, upon cleavage by the reporter enzyme, releases a product measurable by colorimetry, fluorescence or chemiluminescence.

47. A substrate according to claim 45, wherein the substrate is made of organic compounds or synthetic polymers, or from a material selected from glass, plastic, ceramic, semiconductor, silica, fiber optic, diamond, biocompatible monomer and biocompatible polymer materials.

* * * * *

UNITED STATES PATENT AND TRADEMARK OFFICE
CERTIFICATE OF CORRECTION

| | |
|---|---|
| PATENT NO. | : 6,893,827 B1 |
| APPLICATION NO. | : 09/654499 |
| DATED | : May 17, 2005 |
| INVENTOR(S) | : Michelle A. Palmer et al. |

It is certified that error appears in the above-identified patent and that said Letters Patent is hereby corrected as shown below:

Claim 1, Column 47, line 54, please replace "arc" with --are--.

Signed and Sealed this

Seventh Day of October, 2008

JON W. DUDAS
*Director of the United States Patent and Trademark Office*